United States Patent
Kadi et al.

(10) Patent No.: US 9,938,543 B2
(45) Date of Patent: *Apr. 10, 2018

(54) METHODS, REAGENTS AND CELLS FOR BIOSYNTHESIZING GLUTARATE METHYL ESTER

(71) Applicant: INVISTA North America S.á r.l., Wilmington, DE (US)

(72) Inventors: Nadia Fatma Kadi, Cleveland (GB); Mariusz Kamionka, Cleveland (GB); Alexander Brett Foster, Yarm (GB); Alex Van Eck Conradie, Cleveland (GB); Adriana Leonora Botes, East Cleveland (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/741,414

(22) Filed: Jun. 16, 2015

(65) Prior Publication Data

US 2015/0361460 A1   Dec. 17, 2015

Related U.S. Application Data

(60) Provisional application No. 62/012,722, filed on Jun. 16, 2014, provisional application No. 62/012,586, filed on Jun. 16, 2014.

(51) Int. Cl.

| | | |
|---|---|---|
| *C12P 7/62* | (2006.01) | |
| *C12N 9/02* | (2006.01) | |
| *C12N 9/18* | (2006.01) | |
| *C07C 69/42* | (2006.01) | |
| *C12P 13/00* | (2006.01) | |
| *C12P 7/42* | (2006.01) | |
| *C12P 7/44* | (2006.01) | |
| *C07C 229/08* | (2006.01) | |
| *C12N 9/10* | (2006.01) | |
| *C12N 9/16* | (2006.01) | |
| *C12N 15/52* | (2006.01) | |

(52) U.S. Cl.
CPC ............... *C12P 7/62* (2013.01); *C07C 69/42* (2013.01); *C07C 229/08* (2013.01); *C12N 9/0008* (2013.01); *C12N 9/1007* (2013.01); *C12N 9/1096* (2013.01); *C12N 9/16* (2013.01); *C12N 9/18* (2013.01); *C12N 15/52* (2013.01); *C12P 7/42* (2013.01); *C12P 7/44* (2013.01); *C12P 13/001* (2013.01); *C12Y 102/99006* (2013.01); *C12Y 201/01197* (2013.01); *C12Y 206/01018* (2013.01); *C12Y 206/01038* (2013.01); *C12Y 301/01085* (2013.01)

(58) Field of Classification Search
None
See application file for complete search history.

(56) References Cited

U.S. PATENT DOCUMENTS

| | | | |
|---|---|---|---|
| 8,703,455 B2 | 4/2014 | Marliere | |
| 8,741,612 B2 | 6/2014 | Campbell et al. | |
| 9,422,578 B2 | 8/2016 | Pearlman | .................. C12P 5/02 |
| 9,422,580 B2 | 8/2016 | Pearlman | ................ C12P 5/026 |
| 2011/0165644 A1 | 7/2011 | Marliere | |
| 2011/0300597 A1 | 12/2011 | Burk et al. | |
| 2012/0021478 A1 | 1/2012 | Osterhout et al. | |
| 2012/0122563 A1 | 5/2012 | Walker et al. | |
| 2012/0225466 A1 | 9/2012 | Burk et al. | |
| 2013/0189753 A1 | 7/2013 | Pearlman et al. | |
| 2013/0210104 A1 | 8/2013 | Pearlman et al. | |
| 2013/0309742 A1 | 11/2013 | Campbell et al. | |
| 2014/0065686 A1 | 3/2014 | Marliere | |
| 2014/0141482 A1 | 5/2014 | Pearlman et al. | |
| 2014/0186904 A1* | 7/2014 | Botes | ........................ C12P 7/42 |
| | | | 435/128 |
| 2014/0186913 A1 | 7/2014 | Botes et al. | |
| 2015/0037860 A1 | 2/2015 | Botes et al. | |
| 2015/0079654 A1 | 3/2015 | Botes et al. | |
| 2015/0291981 A1 | 10/2015 | Marliere et al. | .......... C12P 5/02 |

FOREIGN PATENT DOCUMENTS

| | | |
|---|---|---|
| EP | 2336340 | 6/2011 |
| EP | 2336341 | 6/2011 |
| EP | 12190039 | 10/2012 |
| WO | WO 2009/155382 | 12/2009 |
| WO | WO 2010001078 | 1/2010 |
| WO | WO 2010/099201 | 9/2010 |
| WO | WO 2011/011689 | 1/2011 |
| WO | WO 2011/076261 | 6/2011 |
| WO | WO 2011/076689 | 6/2011 |
| WO | WO 2011/076691 | 6/2011 |

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.*
Akatsuka et al., "The Serratia marcescens bioH gene encodes an esterase," GENE, Jan. 2003, 302:185-192.
Eriksen et al., "Protein Design for Pathway Engineering," Journal of Structural Biology, Apr. 2013, 185(2):234-242.
Invitation to pay additional fees and, where applicable, protest fee for PCT/US2015/036095, dated Sep. 18, 2015, 13 pages.

(Continued)

*Primary Examiner* — Christian Fronda
(74) *Attorney, Agent, or Firm* — Licata & Tyrrell P.C.; William J. Simmons

(57) ABSTRACT

This document describes biochemical pathways for producing 2,4-pentadienoyl-CoA by forming one or two terminal functional groups, comprised of carboxyl or hydroxyl group, in a C5 backbone substrate such as glutaryl-CoA, glutaryl-[acp] or glutarate methyl ester. 2,4-pentadienoyl-CoA can be enzymatically converted to 1,3-butadiene.

20 Claims, 18 Drawing Sheets

(56) References Cited

FOREIGN PATENT DOCUMENTS

| WO | WO 2011/079314 | 6/2011 |
|---|---|---|
| WO | WO 2011/140171 | 11/2011 |
| WO | WO 2012/018624 | 2/2012 |
| WO | WO 2012/052427 | 4/2012 |
| WO | WO 2012/174439 | 12/2012 |
| WO | WO 2013/007786 | 1/2013 |
| WO | WO 2013/020118 | 2/2013 |
| WO | WO 2013/028519 | 2/2013 |
| WO | WO 2013/040383 | 3/2013 |
| WO | WO 2013036812 | 3/2013 |
| WO | WO 2013/057194 | 4/2013 |
| WO | WO 2013/082542 | 6/2013 |
| WO | WO 2013/090915 | 6/2013 |
| WO | WO 2013/092567 | 6/2013 |
| WO | WO 2013/150100 | 10/2013 |
| WO | WO 2013/173437 | 11/2013 |
| WO | WO 2013/181647 | 12/2013 |
| WO | WO 2013/192183 | 12/2013 |
| WO | WO 2013188546 | 12/2013 |
| WO | WO 2014/001517 | 1/2014 |
| WO | WO 2014/033129 | 3/2014 |
| WO | WO 2014/064198 | 5/2014 |
| WO | WO 2014/085612 | 6/2014 |
| WO | WO 2014/015210 | 11/2014 |

OTHER PUBLICATIONS

Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.
Lin et al., "Biotin Sythesis Begins by Hijacking the Fatty Acid Synthetic Pathway," Nature Chem Biol., Sep. 2010, 6:682-688.
Uniprot Accession No. 032472, Jun. 11, 2014, 2 pages.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A6Q6, Jun. 11, 2014, 3 pages.
Uniprot Accession No. P0A953, Jun. 11, 2014, 4 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.
Uniprot Accession No. Q73Q47, May 14, 2014, 2 pages.
Uniprot Accession No. Q818X2, Jun. 11, 2014, 2 pages.
U.S. Final Office Action in U.S. Appl. No. 14/092,115, dated Oct. 27, 2015, 8 pages.
Westin et al., "The identification of a succinyl-CoA thioesterase suggests a novel pathway for succinate production in peroxisomes," J. Biol Chem, 2005, 280:38125-38132.
Barta et al., "Structural basis for nucleotide binding and reaction catalysis in mevalonate diphosphate decarboxylase," *Biochemistry*, 51(28):5611-5621, Epub Jul. 6, 2012.
Becker et al., "Metabolic flux engineering of L-lysine production in Corynebacterium glutamicum—over expression and modification of G6P dehydrogenase," *Journal of Biotechnology*, 132(2):99-109, Epub Jun. 6, 2007.
Brigham et al., "Engineering Ralstonia eutropha for Production of Isobutanol from CO2, H2, and O2," Advanced Biofuels and Bioproducts, Chapter 39, 1065-1090, 2012.
Brodkorb et al., "Linalool dehydratase-isomerase, a bifunctional enzyme in the anaerobic degradation of monoterpenes," *J Biol Chem.*, 285(40):30436-30442, Epub Jul. 27, 2010.
Buckel et al., "Glutaconate CoA-transferase from Acidaminococcus fermentans," *Eur J Biochem.*, 118(2):315-321, Aug. 1981.
Buckel et al., "2-Hydroxyacyl-CoA dehydratases, a novel family of molybdenum enzymes," J Inorganic Biochemistry, 2003, 96(1):53, 1 page.

Bugg et al., "The emerging role for bacteria in lignin degradation and bio-product formation," *Curr Opin Biotechnol.*, 22(3):394-400, Epub Nov. 9, 2010.
Chayabutra and Ju, "Degradation of n-hexadecane and its metabolites by Pseudomonas aeruginosa under microaerobic and anaerobic denitrifying conditions," *Appl Environ Microbiol.*, 66(2):493-498, Feb. 2000.
Chinese Office Action in Chinese Application No. 201280040122.2, dated Jul. 17, 2015, 7 pages.
Chung and Rhee, "Overexpression of the (R)-specific enoyl-CoA hydratase gene from Pseudomonas chlororaphis HS21 in Pseudomonas strains for the biosynthesis of polyhydroxyalkanoates of altered monomer composition," Biosci. Biotechnol. Biochem., 76(3): 613-616, 2012.
Daniel et al., "Biochemistry of coenzyme B12-dependent glycerol and diol dehydratases and organization of the encoding genes," 1999, FEMS Microbiology Reviews, 22: 553-566.
Dhe-Paganon et al., "Mechanism of mevalonate pyrophosphate decarboxylase: evidence for a carbocationic transition state," *Biochemistry*, 33(45):13355-13362, Nov. 15, 1994.
Eikmanns and Buckel, "Crystalline green 5-hydroxyvaleryl-CoA dehydratase from Clostridium aminovalericum," *Eur. J. Biochem.*, 197(3):661-668, May 8, 1991.
Ferrandez et al., "Genetic characterization and expression in heterologous hosts of the 3-(3-hydroxyphenyl)propionate catabolic pathway of Escherichia coli K-12," *J. Bacteriol.*, 179(8): 2573-2581, Apr. 1997.
Forster-Fromme et al., "Biochemical characterization of isovaleryl-CoA dehydrogenase (LiuA) of Pseudomonas aeruginosa and the importance of liu genes for a functional catabolic pathway of methyl-branched compounds," FEMS Microbiol Lett, 2008, 286(1):78-84.
Fukui et al., "Expression and characterization of (R)-specific enoyl coenzyme A hydratase involved in polyhydroxyalkanoate biosynthesis by Aeromonas caviae," J. Bacteriology, Feb. 1998, 180(3):667-673.
Gehret et al., "Terminal alkene formation by the thioesterase of curacin A biosynthesis: structure of a decarboxylating thioesterase," J. of Biological Chem., 2011, 186(16):14445-14454.
GENBANK accession No. AAD44196.1, Oct. 15, 1999, 1 page.
GENBANK accession No. AAG05403.1, Jan. 31, 2014, 2 pages.
GENBANK accession No. AAV40818.1, Feb. 4, 2005, 1 page.
GENBANK accession No. AAV40819.1, Feb. 4, 2005, 1 page.
GENBANK accession No. AAV40820.1, Feb. 4, 2005, 1 page.
GENBANK accession No. BAA21816.1, Aug. 19, 1997, 2 pages.
GENBANK accession No. BAA92740, Aug. 1, 2007, 2 pages.
GENBANK accession No. CAA32465.1, Jul. 26, 1995, 1 page.
GENBANK accession No. CAA32466.1, Jul. 26, 1995, 1 page.
GENBANK accession No. CAA42196.1, Oct. 16, 1995, 1 page.
GENBANK accession No. CAA99573.1, Nov. 14, 2006, 2 pages.
GENBANK accession No. E1XUJ2.1. Sep. 5, 2012, 2 pages.
GENBANK accession No. NP_746661, Jun. 27, 2013, 2 pages.
Gogerty and Bobik, "Formation of isobutene from 3-hydroxy-3-methylbutyrate by diphosphomevalonate decarboxylase," *Appl Environ Microbiol.*, 76(24):8004-8010, Epub Oct. 22, 2010.
Gu et al., "Polyketide Decarboxylative chain Termination Preceded by O-sulfonation in curacin A Biosynthesis," J. Am. Chemical Soc., Nov. 2009, 131(44):16033-16035.
Guan et al., "Cytochrome P450-dependent desaturation of lauric acid: isoform selectivity and mechanism of formation of 11-dodecenoic acid," *Chem Biol Interact.*, 110(1-2):103-121, Mar. 1998.
He and Spain, "A novel 2-aminomuconate deaminase in the nitrobenzene degradation pathway of Pseudomonas pseudoalcaligenes JS45," *J Bacteriol.*, 180(9):2502-2506, May 1998.
Hermann et al, "Industrial production of amino acids by coryneform bacteria," *J Biotechnol.*, 104(1-3):155-172, Sep. 2003.
International Preliminary Report on Patentability and Written Opinion for PCT/US2012/042757, dated Dec. 17, 2013, 7 pages.
International Preliminary Report on Patentability and Written Opinion for PCT/US2012/064407, dated May 13, 2014, 8 pages.

(56) References Cited

OTHER PUBLICATIONS

International Preliminary Report on Patentability and Written Opinion for PCT/US2012/067463, dated Jun. 3, 2014, 12 pages.
International Preliminary Report on Patentability in International Application No. PCT/US2013/045430, dated Dec. 16, 2014, 12 pages.
International Preliminary Report on Patentability and Written Opinion for PCT/US2013/072275, dated Jun. 2, 2015, 8 pages.
International Search Report in Application No. PCT/US2012/042757 dated Mar. 6, 2013, 5 pages.
International Search Report in Application No. PCT/US2012/064407, dated Feb. 7, 2013, 13 pages.
International Search Report in Application No. PCT/US2012/067463, dated Jun. 17, 2013, 19 pages.
International Search Report and Written Opinion in Application No. PCT/US2013/072275, dated Mar. 6, 2014, 12 pages.
International Search Report and Written Opinion in Application No. PCT/US2013/045430, dated Feb. 3, 2014, 20 pages.
International Search Report and Written Opinion in Application No. PCT/US2014/048606, dated Oct. 31, 2014, 19 pages.
International Search Report and Written Opinion in Application No. PCT/US2014/049807, dated Nov. 5, 2014, 56 pages.
Invitation to pay additional fees and, where applicable, protest fee for PCT/US2012/067463, dated Mar. 13, 2013, 17 pages.
Invitation to pay additional fees and, where applicable, protest fee for PCT/US2013/045430, dated Nov. 25, 2013, 6 pages.
Jang et al., "Bio-based production of C2-C6 platform chemicals," *Biotechnol Bioeng.*, 109(10):2437-2459, Epub Jul. 13, 2012.
Jaremko et al., "The initial metabolic conversion of levulinic acid in Cupriavidus necator," J Biotechnol, 2011, 155(3):293-298.
Jin et al., "The selective addition of water to C=C bonds; enzymes are the best chemists," Chem Commun., 2011, 47:2502-2510.
Kasai et al., "Uncovering the protocatechuate 2,3-cleavage pathway genes," *J Bacteriol.*, 191(21):6758-6768, Epub Aug. 28, 2009.
Kelada et al., "Delta-aminolevulinic acid dehydratase genotype and lead toxicity: A Huge Review," Am. J. Epidemiology, 2001, 154(1)1-13.
Kim et al., "An allylic ketyl radical intermediate in clostridial amino-acid fermentation," Nature., 452(7184):239-242, Mar. 2008.
Kim et al., "Dehydration of ®-2-hydro9xyacyl-CoA to enoyl-CoA in the fermentation of α-amino acids by anaerobic bacteria," FEMS Microbiol Rev, 2004, 28(4):455-468, 14 pages.
Kim, "On the enzymatic mechanism of 2-hydroxyisocaproyl-CoA dehydratase from Clostridium difficile," 2004, Ph.D. dissertation, Philipps-Universitat, Marburg, 2004.
Kizer et al., "Application of Functional Genomics to Pathway Optimization for Increased Isoprenoid Production," *Applied and Environmental Microbiology*, 2008, 74(10):3229-3241.
Köpke et al., "2,3-Butanediol production by acetogenic bacteria, an alternative route to chemical synthesis, using industrial waste gas," App Enviro Microbiol, 2011, 77(15):5467-5475.
Kuzma et al., "Bacteria produce the volatile hydrocarbon isoprene," *Curr Microbiol.*, 30(2):97-103, Feb. 1995.
Kuzuyama, "Mevalonate and nonmevalonate pathways for the biosynthesis of isoprene units," *Biosci Biotechnol Biochem.*, 66(8):1619-1627, Aug. 2002.
Lan et al., "ATP drives direct photosynthetic production of 1-butanol in cyanobacterial," PNAS, 2012, 109(16):6018-6023, 6 pages.
Lee et al., "Synthesis of pure meso-2,3-butanediol from crude glycerol using an engineered metabolic pathway in *Escherichia coli*," Appl Biochem Biotechnol, 2012, 166(7):1801-1813.
Lee et al., "Conversion of beta-methylbutyric acid to beta-hydroxy-beta-methylbutyric acid by Galactomyces reessii," Appl Environ Microbiol, 1997, 63(11):4191-4195, 5 pages.
Li et al., "Cupriavidus necator JMP134 rapidly reduces furfural with a Zn-dependent alcohol dehydrogenase," Biodegradation, 22(6): 1215-1225, Nov. 2011.

Li et al., "JMP134 rapidly reduces furfural with a Zn-dependent alcohol dehydrogenase," Biodegradation, 2011, 22(6):1215-1225, 11 pages.
Lim et al., "Amplification of the NADPH-Related Genes zwf and gnd for the Oddball Biosynthesis of PHBin an *E. coli* Tranformant Harboring a Cloned phbCAB Operon," J Bioscience and Bioengineering, 2002, 93(6):543-549.
Liu et al., "Microbial production of R-3-hydroxybutyric acid by recombinant *E. coli* harboring genes of phbA, phbB, and tesB," *Appl Microbiol Biotechnol.*, 76(4):811-818, Epub Jul. 4, 2007.
Luddeke et al. "Geraniol and Geranial Dehydrogenases Induced in Anaerobic Monoterpene Degradation by Castellaniella defragrans," Appl. and Environmental Microbiology, 2012, 78(7): 2128-2136.
Luddeke et al.,"Enantiospecific (S)-(+)-linalool formation from beta-myrcene by linalool dehydratase-isomerase," Z Naturforsch C., Jul./Aug. 2011, 66(7-8):409-412.
Luo et al., "Production of 3-hydroxypropionic acid through propionaldehyde dehydrogenase PduP mediated biosynthetic pathway in Klebsiella pneumoniae," *Bioresour Technol.*, 103(1):1-6, Epub Oct. 2, 2011.
Martin et al., "High-titer production of monomeric hydroxyl valerates from levulinic acid I Pseudomonas putida," J Biotechnol, 2009, 139(1):61-67.
Martin et al., "Engineering a mevalonate pathway in *Escherichia coli* for production of terpenoids," Nature Biothechnology, Jul. 2003, 21(7):796-802.
McCarthy et al., "Structural basis of functional group activation by sulfotransferases in complex metabolic pathways," ACS Chem. Biol., 2012, 7:1994-2003.
Meijnen et al., "Improved p-hydroxybenzoate productoin by engineered Pseudomonas putida S12 by using a mixed-substrate feeding strategy," Appl Microbiol Biotechnol, 2011, 90(3):885-893.
Mo et al., "Biosynthesis of the allylmalonyl-CoA extender unit for the FK506 polyketide synthase proceeds through a dedicated polyketide synthase and facilitates the mutasynthesis of analogues," *J Am Chem Soc.*, 133(4):976-985, Epub Dec. 22, 2010 [author manuscript].
Morone et al., "Increasing diterpene yield with a modular metabolic engineering system in *E. coli*: comparison of MEV and MEP isoprenoid precursor pathway engineering," *Applied Microbiology and Biotechnology*, 2010, 85:1893-1906.
Muraki et al., "Prokaryotic homologs of the eukaryotic 3-hydroxyanthranilate 3,4-dioxygenase and 2-amino-3-carboxymuconate-6-semialdehyde decarboxylase in the 2-nitrobenzoate degradation pathway of Pseudomonas fluorescens strain KU-7," *Appl Environ Microbiol.*, 69(3):1564-1572, Mar. 2003.
Ohashi et al., "Continuous production of lactic acid from molasses by perfusion culture of Lactococcus lactis using a stirred ceramic membrane reactor," J Bioscience and Bioengineering, 1999, 87(5):647-654.
Papanikolaou et al., "Citric acid production by Yarrowia lipolytica cultivated on olive-mill wastewater-based media,"Bioresour. Technol., 2008, 99(7):2419-2428.
Pérez-Pantoja et al., "Metabolic reconstruction of aromatic compounds degradation from the genome of the amazing pollutant-degrading bacterium Cupriavidus necator JMP134," FEMS Microbiol Rev., 2008, 32(5):736-794.
Prather et al., "De nova biosynthetic pathways: rational design of microbial chemical factories," 2008, 19:468-474.
"Production of butadiene," China Synthetic Rubber Industry, Special issue of 1978, 21 pages (with partial English translation).
Prybylski et al., "Third-generation feed stocks for the clean and sustainable biotechnological production of bulk chemicals: synthesis of 2-hydroxyisobutyric acid," Energy, Sustainability and Society, 2012, 2:11.
Ramsay et al., "Use of a Nylon Manufacturing Waste as an Industrial Fermentation Substrate," Appl Environ Microbiol, 1986, 52(1):152-156.
Rettie et al., "CYP4 Isozyme Specificity and the Relationship between co-Hydroxylation and Terminal Desaturation of Valproic Acid," Biochemistry, 34(24): 7889-7895 (1995).

(56) References Cited

OTHER PUBLICATIONS

Rude et al., "Terminal olefin (1-alkene) biosynthesis by a novel p450 fatty acid decarboxylase from *Jeotgalicoccus* speciesm," Appl. Environ. Microbiol., 2011, 77(5):1718-1727.
Schäfer et al., "Synthesis of short-chain diols and unsaturated alcohols from secondary alcohol substrates by the Rieske nonheme mononuclear iron oxygenase MdpJ.," Appl Environ Microbiol., 78(17):6280-6284, Epub Jun. 29, 2012.
Scherf and Buckel, "Purification and properties of an iron-sulfur and FAD-containing 4-hydroxybutyryl-CoA dehydratase/vinylacetyl-CoA delta 3-delta 2-isomerase from Clostridium aminobutyricum," *Eur J Biochem.*, 215(2):421-429, Jul. 15, 1993.
Scherf et al., "Succinate-ethanol fermentation in Clostridium kluyveri: purification and characterisation of 4-hydroxybutyryl-CoA dehydratase/vinylacetyl-CoA delta 3-delta 2-isomerase," *Arch Microbiol.*, 161(3):239-245, 1994.
Seedorf et al., "The genome of *Clostridium kluyveri*, a strict anaerobe with unique metabolic features," Proc Natl Acad Sci USA, 2008, 105(6):2128-2133.
Shen et al., "Driving Forces Enable High-Titer Anaerobic 1-Butanol Synthesis in *Escherichia coli*," Appl Environ Microbiol., 2011, 77(9):2905-2915.
Silver and Fall, "Characterization of aspen isoprene synthase, an enzyme responsible for leaf isoprene emission to the atmosphere," *J Biol Chem.*, 270(22):13010-13016, Jun. 2, 1995.
Sweeney et al., "Physiologically based pharmacokinetic modeling of 1,3-butadiene, 1,2-epoxy-3-butene, and 1,2:3,4-diepoxybutane toxicokinetics in mice and rats," *Carcinogenesis.*, 18(4):611-625, Apr. 1997.
Tseng et al., "Biosynthesis of chiral 3-hydroxyvalerate from single propionate-unrelated carbon sources in metabolically engineered *E. coli*," *Microb Cell Fact.*, 9:96, Nov. 27, 2010.
Tsuge et al., "Molecular characterization and properties of (R)-specific enoyl-CoA hydratases from Pseudomonas aeruginosa: metabolic tools for synthesis of polyhydroxyalkanoates via fatty acid beta-oxidation," *Int J Biol Macromol.*, 31(4-5):195-205, Jan. 2003.
Toraya, "Radical catalysis of B12 enzymes: structure, mechanism, inactivation and reactivation of diol and glycerol dehydratases," Cellular and Molecular Life Sciences, 2000, 57:106-127.
Ulmer et al., "Bacterial production of poly(.beta.-hydroxyalkano-ates) containing unsaturated repeating units by Rhodospirillum rubrum," Macromolecules, 27(7):1675-1679, 1994.
Uniprot Accession No. B8ZLF3, Jun. 15, 2010, 2 pages.
Uniprot Accession No. I3RA72, Sep. 5, 2012, 2 pages.
Uniprot Accession No. P32377, Jun. 15, 2010, 4 pages.
Uniprot Accession No. Q7CCL9, Jun. 15, 2010, 2 pages.
Upton and Mckinney, "Role of the methylcitrate cycle in propionate metabolism and detoxification in *Mycobacterium smegmatis*," *Microbiology*, 153(Pt 12):3973-3982, Dec. 2007.
U.S. Final Office Action in U.S. Appl. No. 13/691,623, dated Dec. 9, 2014, 15 pages.
U.S. Final Office Action in U.S. Appl. No. 13/524,973, dated Dec. 22, 2014, 24 pages.
U.S. Non-Final Office Action in U.S. Appl. No. 13/691,623, dated Jun. 25, 2014, 13 pages.
U.S. Non-Final Office Action in U.S. Appl. No. 13/524,973, dated Jun. 11, 2014, 17 pages.
U.S. Non-Final Office Action in U.S. Appl. No. 13/092,115, dated Apr. 1, 2015, 21 pages.
U.S. Non-Final Office Action in U.S. Appl. No. 13/916,156, dated Jul. 14, 2015, 35 pages.
U.S. Non-Final Office Action in U.S. Appl. No. 13/524,973, dated Jul. 23, 2015, 24 pages.
Van Leeuwen et al., "Fermentative production of isobutene," Appl Microbiol Biotechnol, 2012, 93(4):1377-1387.
Wang and Liao, "Alteration of product specificity of Rhodobacter sphaeroides phytoene desaturase by directed evolution," *J Biol Chem.*, 276(44):41161-41164, Epub Aug. 28, 2001.
Wee et al., "Biotechnological production of lactic acid and its recent applications," Food Technol. Biotechnol., 2006, 44(2):163-172.
Wendt et al., "Crystal structure of the carboxyltransferase subunit of the bacterial sodium ion pump glutaconyl-coenzyme A decarboxylase," *EMBO J.*, 22(14):3493-3502, Jul. 15, 2003.
White, "Butadiene production process overview," *Chem Biol Interact.*, 166(1-3):10-14, Epub Jan. 26, 2007.
Yang et al., "Enhancing production of bio-isoprene using hybrid MVA pathway and isoprene synthase in *E. coli*," *PLoS One*, Apr. 2012, 7:1-7.
Yang et al., "Value-added uses for crude glycerol-a byproduct of biodiesel production," Biotechnology for Biofuels, 2012, 5:13, 10 pages.
Zhao et al., "Biosynthesis of isoprene in *Escherichia coli* via methylerythritol phosphate (MEP) pathway," *Applied Microbilogy and Biotechnology*, Apr. 2011, 90:1915-1922.
Zhang et al., "Genes encoding acyl-CoA dehydrogenase (AcdH) homologues from *Streptomyces coelicolor* and *Streptomyces avermitilis* provide insights into the metabolism of small branched-chain fatty acids and macrolide antibiotic production," Microbiology, 1999, 145(9):2323-2334, 12 pages.
Zhuang et al., "Divergence of function in the Hotdog-fold enzyme superfamily: the bacterial thioesterase YciA," Biochemistry, 2008, 47(9):2789-2796, 8 pages.
International Search Report and Written Opinion in Application No. PCT/US2014/049786, dated Sep. 11, 2015, 17 pages.
Office Communication dated Dec. 3, 2015 in U.S. Appl. No. 13/916,156, filed Jun. 12, 2013.
Office Communication dated Mar. 15, 2016 in U.S. Appl. No. 13/916,156, filed Jun. 12, 2013.
Office Communication dated Apr. 7, 2016 in U.S. Appl. No. 13/916,156, filed Jun. 12, 2013.
Office Communication dated Apr. 20, 2016 in U.S. Appl. No. 13/916,156, filed Jun. 12, 2013.
Office Communication dated May 17, 2016 in U.S. Appl. No. 13/916,156, filed Jun. 12, 2013.
Office Communication dated Dec. 7, 2015 in U.S. Appl. No. 13/691,623, filed Nov. 30, 2012.
Office Communication dated May 4, 2016 in U.S. Appl. No. 13/691,623, filed Nov. 30, 2012.
Office Communication dated Apr. 20, 2016 in U.S. Appl. No. 13/524,973, filed Jun. 15, 2012.
Office Communication dated Aug. 30, 2016 in U.S. Appl. No. 13/524,973, filed Jun. 15, 2012.
Office Communication dated Jan. 26, 2017 in U.S. Appl. No. 13/524,973, filed Jun. 15, 2012.
Office Communication dated Feb. 2, 2016 in U.S. Appl. No. 14/092,115, filed Nov. 27, 2013.
Office Communication dated Mar. 21, 2016 in U.S. Appl. No. 14/092,115, filed Nov. 27, 2013.
Office Communication dated Jul. 12, 2016 in U.S. Appl. No. 14/092,115, filed Nov. 27, 2013.
Office Communication dated Oct. 12, 2016 in U.S. Appl. No. 14/092,115, filed Nov. 27, 2013.
Office Communication dated Nov. 17, 2016 in U.S. Appl. No. 14/914,741, filed Feb. 26, 2016.
Office Communication dated Feb. 7, 2017 in U.S. Appl. No. 14/914,741, filed Feb. 26, 2016.
Office Communication dated Feb. 5, 2016 in U.S. Appl. No. 14/334,190, filed Jul. 17, 2014.
Office Communication dated Jul. 27, 2016 in U.S. Appl. No. 14/334,190, filed Jul. 17, 2014.
Office Communication dated Jan. 20, 2017 in U.S. Appl. No. 14/334,190, filed Jul. 17, 2014.
Office Communication in EP12731825.1 dated Nov. 17, 2015.
Office Communication in CN201280068870.1 dated Aug. 23, 2016.
Office Communication in EP12799032.3 dated Jun. 16, 2016.
Office Communication in EP12799032.3 dated Mar. 3, 2016.
Office Communication in EP12799032.3 dated Dec. 10, 2015.
Office Communication in CN201280040122.2 dated Jun. 8, 2016.
Office Communication in CN201280040122.2 dated Jul. 17, 2015.
Office Communication in CN201380043586.3 dated Nov. 8, 2016.
Office Communication in EP13812263.5 dated Jan. 12, 2017.

(56) References Cited

OTHER PUBLICATIONS

Office Communication dated May 20, 2016 in U.S. Appl. No. 14/452,201, filed Aug. 5, 2014.
Office Communication dated Oct. 28, 2016 in U.S. Appl. No. 14/452,201, filed Aug. 5, 2014.
Chica et al. "Semi-rational approached to engineering enzyme activity: combining the benefits of directed evolution and rational design" Current Opinion in Biotechnology 2005 16:378-384.
Liu et al. "Zirconia microbial hollow fibre bioreactor for *Esherichia coli* culture" Ceramics International 2010 36:2087-2093.
Sen et al. "Developments in Directed Evolution for Improving Enzyme Functions" Appl. Biochem. Biotechnol. 2007 143:212-223.
Studier, F.W. "Protein production by auto-induction in high density shaking cultures" Protein Expression and Purification 2005 41:207-234.

\* cited by examiner

FIGURE 8

| SEQ ID NO | Organism | GENBANK reference | Amino acid sequence |
|---|---|---|---|
| 1 | Escherichia coli | AAC76437.1 | MNNIWWQTKGQGNVHLVLLHGWGLNAEVWRCIDEELSSHFTLHLVDLPGFGRSRGFGALS LADMAEAVLQQAPDKAIWLGWSLGGLVASQIALTHPERVQALVTVASSPCFSARDEWPGI KPDVLAGFQQQLSDDFQRTVERFLALQTMGTETARQDARALKKTVLALPMPEVDVLNGGL EILKTVDLRQPLQNVSMPFLRLYGYLDGLVPRKVVPMLDKLWPHSESYIFAKAAHAPFIS HPAEFCHLLVALKQRV |
| 2 | Mycobacterium marinum | ACC40567.1 | MSPITREERLERRIQDLYANDPQFAAAKPATAITAAIERPGLPLPQIIETVMTGYADRPA LAQRSVEFVTDAGTGHTTLRLLPHFETISYGELWDRISALADVLSTEQTVKPGDRVCLLG FNSVDYATIDMTLARLGAVAVPLQTSAAITQLOPIVAETQPTMIAASVDALADATELALS GQTATRVLVFDHHRQVDAHRAAVESARERLAGSAVVETLAEAIARGDVPRGASAGSAPGT DVSDDSLALIIYTSGSTGAPKGAMYPRRNVATFWRKRTWFEGGYEPSITLNFMPMSHVMG RQILYGTLCNGGTAYFVAKSDLSTLFEDLALVRPTELTFVPRVWDMVFDEFQSEVDRRLV DGADRVALEAQVKAEIRNDVLGGRYTSALTGSAPISDEMKAWVEELLDMHLVEGYGSTEA GMILIDGAIRRPAVLDYKLVDVPDLGYFLTDRPHPRGELLVKTDSLFPGYYQRAEVTADV FDADGFYRTGDIMAEVGPEQFVYLDRRNNVLKLSQGEFVTVSKLEAVFGDSPLVRQIYIY GNSARAYLLAVIVPTQEALDAVPVEELKARLGDSLQEVAKAAGLQSYEIPRDFIIETTPW TLENGLLTGIRKLARPQLKKHYGELLEQJYTDLAHGQADELRSLRQSGADAPVLVTVCRA AAALLGGSASDVQPDAHFTDLGGDSLSALSFTNLLHEIFDIEVPVGVIVSPANDLQALAD YVEAARKPGSSRPTFASVHGASNGQVTEVHAGDLSLDKFIDAATLAEAPRLPAANTQVRT VLLTGATGFLGRYLALEWLERMDLVDGKLICLVRAKSDTEARARLDKTFDSGDPELLAHY RALAGDHLEVLAGDKGEADLGLDRQTWQRLADTVDLIVDPAALVNHVLPYSQLFGPNALG TAELLRLALTSKIKPYSYTSTIGVADQIPPSAFTEDADIRVISATRAVDDSYANGYSNSK WAGEVLLREAHDLCGLPVAVFRCDMILADTTWAGQLNVPDMFTRMILSLAATGIAPGSFY ELAADGARQRAHYDGLPVEFIAEAISTLGAQSQDGFHTYHVMNPYDDGIGLDEFVDWLNE SGCPIQRIADYGDWLQRFETALRALPDRQRHSSLLPLLHNYRQPERPVRGSIAPTDRFRA AVQEAKIGPDKDIPHYGAPIIVKYYVSDLRLLGLL |

FIGURE 8 (Continued)

| SEQ ID NO | Organism | GENBANK reference | Amino acid sequence |
|---|---|---|---|
| 3 | Mycobacterium smegmatis | ABK71854.1 | MTSDVHDATDGVTETALDDEQSTRRIAELYATDPEFAAAAPLPAVVDAAHKPGLRLAEIL QTLFTGYGDRPALGYRARELATDEGGRTVTRLLPRFDTLTYAQVWSRVQAVAAALRHNFA QPIYPGDAVATIGFASPDYLTLDLVCAYLGLVSVPLQHNAPVSRLAPILAEVEPRILTVS AEYLDLAVESVRDVNSVSQLVVFDHHPEVDDHRDALARAREQLAGKGIAVTTLDAIADEG AGLPAEPIYTADHDQRLAMILYTSGSTGAPKGAMYTEAMVARLWTMSFITGDPTPVINVN FMPLNHLGGRIPISTAVQNGGTSYFVPESDMSTLFEDLALVRPTELGLVPRVADMLYQHH LATVDRLVTQGADELTAEKQAGAELREQVLGGRVITGFVSTAPLAAEMRAFLDITLGAHI VDGYGLTETGAVTRDGVIVRPPVIDYKLJDVPELGYFSTDKPYPRGELLVRSQITLPGYY KRPEVTASVFDRDGYYHTGDVMAETAPDHLVYVDRRNNVLKLAQGEFVAVANLEAVFSGA ALVRQIFVYGNSERSFLLAVVVPTPEALEQYDPAALKAALADSLQRTARDAELQSYEVPA DFIVETEPFSAANGLLSGVGKLLRPNLKDRYGQRLEQMYADIAATQANQLRELRRAAATQ PVIDTLTQAAATILGTGSEVASDAHFTDLGGDSLSALTLSNLLSDFFGFEVPVGTIVNPA TNLAQLAQHEAQRTAGDRRPSFTTVHGADATEIRASELTLDKFIDAETLRAAPGLPKVT TEPRTVLLSGANGWLGRFLTLQWLERLAPVGGTLITIVRGRDDAAARARLTOAYDTDPEL SRRFAELADRHLRVVAGDIGDPNLGLTPEIWHRLAAEVDLVVHPAALVNHVLPYRQLFGP NVVGTAEVIKLALTERIKPVTYLSTVSVAMGIPDFEEDGDIRTVSPVRPLDGGYANGYGN SKWAGEVLLREAHDLCGLPVATFRSDMILAHPRYRGQVNVPDMFTRLLLSLLITGVAPRS FYIGDGERPRAHYPGLTVDFVAEAVTTLGAQQREGVSYSYDVMNPHDDGISLDVFVDWLIR AGHPIDRVDYDYDDWVRRFETALTALPEKRRAQTVLPLLHAFRAPQAPLRGAPEPTEVFHA AVRTAKVGPGDIPHLDEALIDKYIRDLREFGLI |

FIGURE 8 (Continued)

| SEQ ID NO | Organism | GENBANK reference | Amino acid sequence |
|---|---|---|---|
| 4 | Segniliparus rugosus | EFV11917.1 | MGDGEERAKRFFQRIGELSATDPQFAAAAPDPAVVEAVSDPSLSFTRYLDTLMRGYAERP ALAHRVGAGYETISYGELWARVGAIAAAWQADGLAPGDFVATVGFTSPDYVAVDLAAARS GLVSVPLQAGASLAQLVGILEETEPKVLAASASSLEGAVACALAAPSVQRLVVFDLRGPD ASESAADERRGALADAEFQLARAGRAVVVETLADLAARGEALPEAPLFEPAEGEDPLALL IYTSGSTGAPKGAMYSQRLVSQLWGRTPVVPGMPNISLHYMPLSHSYGRAVLAGALSAGG TAHFTANSDLSTLFEDIALARPTFLALVPRVCEMLFQESQRGQDVAELRERVLGGRLLVA VCGSAPLSPEMRAFMEEVLGFPLLDGYGSTEALGVMRNGIIQRPPVIDYKLVDVPELGYR TTDKPYPRGELCIRSTSLISGYYKRPEITAEVFDAQGYYKTGDVMAEJAPDHLVYVDRSK NVLKLSQGEFVAVAKLEAAYGTSPVVKQIFVYGNSERSFLLAVVVPNAEVLGARDQEEAK PLIAASLQKIAKEAGLQSYEVPRDFLIETEPFTTQNGLLSEVGKLLRPKLKARYGEALEA RYDEIAHGQADELRALRDGAGQRPVVETVVRAAVAISGSEGAEVGPEANFADLGGDSLSA LSLANLLHDVFEVEVPVRIIIGPTASLAGIAKHEAERAGASAPTAASVHGAGATRIRAS ELTLEKFLPEDLLAAAKGLPAADQVRTVLLTGANGWLGRFLALEQLERLARSGQDGGKLI CLVRGKDAAAARRIEETLGTDPALAARFAELAEGRLEVPGDVGEPKFGLDDAAWDRLA EEVDVIVHPAALVNHVLPYHQLFGPNVVGTAEIIRLAITAKRKPVTYLSTVAVAAGVEPS SFEEDGDIRAVVPERPLGDGYANGYGNSKWAGEVLLREAHELVGLPVAVFRSDMILAHTR YTGQLNVPDQFTRLVLSLLATGIAPKSFYQQGAAGERQRAHYDGIPVDFTAEAITTLGAE PSWFDGGAGFRSFDVFNPHHDGVGLDEFVDWLIEAGHPISRIDDHKEWFARFETAVRGLP EAQRQHSLLPLLRAYSFPHPPVDGSVYPTGKFQGAVKAAQVGSDHDVPHLGKALIVKYAD DLKALGLL |

FIGURE 8 (Continued)

| SEQ ID NO | Organism | GENBANK reference | Amino acid sequence |
|---|---|---|---|
| 5 | Mycobacterium smegmatis | ABK75684.1 | MTIETREDRFNRRIDHLFETDPQFAAARPDEAISAAAADPELRLPAAVKQILAGYADRPA LGKRAVEFVTDEEGRTTAKLLPRFDTITYRQLAGRIQAVTNAWHNHPVNAGDRVAILGFT SVDYTTIDIALLELGAVSVPLQTSAPVAQLQPIVAETEPKVIASSVDFLADAVALVESGP APSRLVVFDYSHEVDDQREAFEAAKGKLAGTGVVVETITDALDRGRSLADAPLYVPDEAD PLTLLIYTSGSTGTPKGAMYPESKTATMWQAGSKARWDETLGVMPSITLNFMPMSHVMGR GILCSTLASGGTAYFAARSDLSTFLEDLALVRPTQLNFVPRIWDMLFQEYQSRLDNRRAE GSEDRAEAAVLEEVRTQLLGGRFVSALTGSAPISAEMKSWVEDLLDMHLLEGYGSTEAGA VFIDGQIQRPPVIDYKLVDVPDLGYFATDRPYPRGELLVKSEQMFPGYYKRPEITAEMFD EDGYYRTGDIVAELGPDHLEYLDRRNNVLKLSQGEFVTVSKLEAVFGDSPLVRQIYVYGN SARSYLLAVVVPTEEALSRWDGDELKSRISDSLQDAARAAGLQSYEIPRDFLVETTPFTL ENGLLTGIRKLARPKLKAHYGERLEQLYTDLAEGQANELRELRRNGADRPVVETVSRAAV ALLGASVTDLRSDAHFTDLGGDSLSALSFSNLLHEIFDVDVPVGVIVSPATDLAGVAAYI EGELRGSKRPTYASVHGRDATEVRARDLALGKFIDAKTLSAAPGLPRSGTEIRTVLLTGA TGFLGRYLALEWLERMDLVDGKVICLVRARSDDEARARILDATFDTGDATLLEHYRALAAD HLEVIAGDKGEADLGLDHDTWQRLADTVDLIVDPAALVNHVLPYSQMFGPNALGTAELIR IALTTTIKPVVYVSTIGVGQGISPEAFVEDADIREISATRRVDDSYANGYGNSKWAGEVL LREAHDWCGLPVSVFRCDMILADTTYSGQLNLPDMFTRLMLSLVATGIAPGSFYELDADG NRQRAHYDGLPVEFIAEAISTIGSQVTDGFETFHVMNPYDDGIGLDEYVDWLIEAGYPVH RVDDYATWLSRFETALRALPERQRQASLLPLLHNYQQPSPPVCGAMAPTDRFRAAVQDAK IGPDKDIPHVTADVIVKYISNLQMLGLL |

FIGURE 8 (Continued)

| SEQ ID NO | Organism | GENBANK reference | Amino acid sequence |
|---|---|---|---|
| 6 | Mycobacterium massiliense | EIV11143.1 | MTNETNPQQEQLSRRIESLRESDPQFRAAQPDPAVAEQVLRPGLHLSEAIAALMTGYAER PALGERARELVIDQDGRTTLRLLPRFDTTYGELWSRTTSVAAAWHHDATHPVKAGDLVA TLGFTSIDYTVLDLAIMILGGVAVPLQTSAPASQWTTILAEFAEPNTLAVSIELIGAAMES VRATPSIKQVVVFDYTPEVDDQREAFEAASTQLAGTGIALETILDAVIARGAALPAAPLYA PSAGDDPLALLIYTSGSTGAPKGAMHSENIVRRWWIREDVMAGTENLPMIGLNFMPMSHI MGRGTLTSTLSTGGTGYFAASSDMSTLFEDMELIRPTALALVPRVCDMVFQRFQTEVDRR LASGDTASAEAVAAEVKADIRDNLFGGRVSAVMVGSAPLSEELGEFIESCFELNLTDGYG STEAGMVFRDGIVQRPPVIDYKLVDVPELGYFSTDKPHPRGELLLKTDGMFLGYYKRPEV TASVFDADGFYMTGDIVAELAHDNIEHDRRNNVLKLSQGEFVAVATLEAEYANSPVVHQ IYVYGSSERSYLLAVVVPTPEAVAAAKGDAAALKTTIADSLQDIAKEIQLQSYEVPRDFI IEPQPFTQGNGLLTGIAKLARPNLKAHYGPRLEQMYAEIAEQQAAELRALHGVDPDKPAL ETVLKAAQALLGVSSAELAADAHFTDLGGDSLSALSFSDLLRDIFAVEVPVGVIVSAAND LGGVAKFVDEQRHSGGTRPTAETVHGAGHTEIRAADLTLDKFIDEATLHAAPSLPKAAGI PHTVLLTGSNGYLGHYLALEWLERLDKTDGKLIVIVRGKNAEAAYGRLEEAFDTGDTELL AHFRSLADKHLEVLAGDIGDPNLGLDADTWQRLADTVDVIVHPAALVNHVLPYNQLFGPN VVGTAEIIKLAITTKIKPVTYLSTVAVAAYVDPTTFDEESDIRLISAVRPIDDGYANGYG NAKWAGEVLLREAHDLCGLPVAVFRSDMILAHSRYTGQLNVPDQFTRLILSLIATGIAPG SFYQAQTTGERPLAHYDGLPGDFTAEAITTLGTQVPEGSEGFVTYDCVNPHADGISLDNF VDWLIEAGYPIARIDNYTEWFTRFDTAIRGLSEKQKQHSLLPLLHAFEQPSAAENHGVVP AKRFQHAVQAAGIGPVGQDGTTDIPHLSRRLIVKYAKDLEQLGLL |

FIGURE 8 (Continued)

| SEQ ID NO | Organism | GENBANK reference | Amino acid sequence |
|---|---|---|---|
| 7 | Segniliparus rotundus | ADG98140.1 | MTQSHTQGPQASAAHSRLARRAAELLATDPQAAATLPDPEVVRQATRPGLRLAERVDAIL SGYADRPALGQRSFQTVKDPITGRSSVELLPTFDTITYRELRERATAIASDLAHHPQAPA KPGDFLASIGFISVDYVAIDIAGVFAGLTAVPLQTGATLATLTAITAETAPTLFAASIEH LPTAVDAVLATPSVRRLLVFDYRAGSDEDREAVEAAKRKIADAGSSVLVDVLDEVIARGK SAPKAPLPPATDAGDDSLSLLIYTSGSTGTPKGAMYPERNVAHFWGGVWAAAFDEDAAPP VPAINITFLPLSHVASRLSLMPTLARGGLMHFVAKSDLSTLFEDLKLARPTNLFLVPRVV EMLYQHYQSELDRRGVQDGTREAEAVKDDLRTGLLGGRILTAGFGSAPLSAELAGFIESL LQIHLVDGYGSTEAGPVWRDGYLVKPPVTDYKLIDVPELGYFSTDSPHPRGELAIKTQJI LPGYYKRPETTAEVFDEDGFYLTGDVVAQIGPEQFAYVDRRKNVLKLSQGEFVTLAKLEA AYSSPLVRQLFVYGSSERSYLLAVIVPTPDALKKFGVGEAAKAALGESLQKIARDEGLQ SYEVPRDFHETDPFTVENGILSDARKSLRPKLKEHYGERLEAMYKELADGQANELRDIR RGVQQRPTLETVRRAAAAMLGASAAEIKPDAHFTDLGGDSLSALTSNFLHDLFEVDVPV GVIVSAANTLGSVAEHIDAQLAGGRARPTFATVHGKGSTTIKASDLTLDKFIDEQTLEAA KHLPKPADPPRTVLLTGANGWLGRFLALEWLERLAPAGGKLITIVRGKDAAQAKARLDAA YESGDPKLAGHYQDLAATTLEVLAGDFSEPRLGLDEATWNRLADEVDFISHPGALVNHVL PYNQLFGPNVAGVAEIIKLAITTRIKPVTYLSTVAVAAGVEPSALDEDGDIRTVSAERSV DEGYANGYGNSKWGGEVLLREAHDRTGLPVRVFRSDMILAHQKYTGQVNATDQFTRLVQS LLATGLAPKSFYELDAQGNRQRAHYDGIPVDFTAESITTLGGDGLEGYRSYNVFNPHRDG VGLDEFVDWLIEAGHPITRIDDYDQWLSRFETSLRGLPESKRQASVLPLLHAFARPGPAV DGSPFRNTVFRTDVQKAKIGAEHDIPHLGKALVLKYADDIKQLGLL |
| 8 | Pseudomonas fluorescens | AAC60471.2 | MQIQGHYELQFEAVREAFAALFDDPQERGAGLCIQIQGGETVDLWAGTADKDGTEAWHSD TIVNLFSCTKTFTAVTALQLVAEGKLQLDAPVANYWPEFAAAGKEAITLRQLLCHQAGLP AIREMILPTEALYDWRLMVDTLAAEAPWWTPGQGHGYEAITYGWLVGELLRRADGRGPGES IVARVARPLGLDFHVGLADEEFYRVAHIARSKGNMGDEAAQRLLQVMMREPTAMTTRAFA NPPSILTSTNKPEWRRMQQPAANGHGNARSLAGFYSGLLDGSLLEADMLEQLTREHSIGP DKTLLTQTRFGLGCMLDQQPQLPNATFGLGPRAFGHPRSAPVVRWVLPEHDVAFGFVTNT LGPYVLMDPRAQKLVGILAGCL |
| 9 | Lactobacillus brevis | ABJ63754.1 | MAANEFSETHRVVYYEADDTGQLTAMLINLFVLVSEDQNDALGLSTAFVQSHGVGWVVT QYHLHIDELPRTGAQVTIKTRATAYNRYFAYREYWLLDDAGQVLAYGEGIWVTMSYATRK ITTIPAEVMAPYHSEEQTRLPRLPRPDHFDEAVNQTLKPYTVRYFDIDGNGHVNNAHYFD WMLDVLPATFLRAHHPTDVKIRFENEVQYGHQVTSELSQAAALTTQHMIKVGDLTAVKAT IQWDNR |

FIGURE 8 (Continued)

| SEQ ID NO | Organism | GENBANK reference | Amino acid sequence |
|---|---|---|---|
| 10 | Lactobacillus plantarum | CCC78182.1 | MAATLGANASLYSEQHRITYYECDRTGRATLTTLIDIAVLASEDQSDALGLTTEMVQSHGV GWVVTQYAIDITRMPRQDEVVTIAVRGSAYNPYFAYREFWIRDADGQQLAYITSIWVMMS QTTRRIVKILPELVAPYQSEVVKRIPRLPRPISFEATDTTITKPYHVRFFDIDPNRHVNN AHYFDWLVDTLPATFLLQHDLVHVDVRYENEVKYGQTVTAHANILPSEVADQVTTSHUE VDDEKCCEVTIQWRTLPEPIQ |
| 11 | Treponema denticola | AAS11092.1 | MIVKPMVRNNICLNAHPQGCKKGVEDQJEYTKKRITAEVKAGAKAPKNVLVLGCSNGYGL ASRITAAFGYGAATIGVSFEKAGSETKYGTPGWYNNLAFDEAAKREGLYSVTIDGDAFSD EIKAQVIEEAKKGIKFDLIVYSLASPVRTDPDTGIMHKSVLKPFGKTFTGKTVDPFTGE LKEISAEPANDEEAAATVKVMGGEDWERWIKQLSKEGLLEEGCITLAYSYIGPEATQALY RKGTIGKAKEHLEATAHRLNKENPSIRAFVSVNKGLVTRASSAVIPVIPLYLASLFKVMKE KGNHEGCIEQJTRLYAERLYRKDGTIPVDEENRIRIDDWELEEDVQKAVSALMEKVTGEN AESLTDLAGYRHDFLASNGFDVEGINYEAEVERFDRI |
| 12 | Euglena gracilis | AAW66853.1 | MSCPASPSAAVVSAGALCLCVATVLLATGSNPTALSTASTRSPTSLVRGVDRGLMRPTTA AALTTMREVPQMAEGFSGEATSAWAAAGPQWAAPLVAAASSALALWWWAARRSVRRPLAA LAELPTAVTHLAPPMAMFTTAKVIQPKIRGFICTTHPIGCEKRVQEEIAYARAHPPTS PGPKRVLVIGCSTGYGLSTRITAAFGYQAATLGVFLAGPPTKGRPAAAGWYNTVAFEKAA LEAGLYARSLNGDAFDSTTKARTVEAIKRDLGTVDLVVYSIAAPKRTDPATGVLHKACLK PIGATYTNRTVNTDKAEVTDVSIEPASPEEIADTVKVMGGEDWELWIQALSEAGVLAEGA KTVAYSYIGPEMTWPVYWSGTIGEAKKDVEKAAKRITQQYGCPAYPVVAKALVTQASSAI PVVPLYICLLYRVMKEKGTHEGCIEQMVRLLTTKLYPENGAPIVDEAGRVRVDDWEMAED VQQAVKDLWSQVSTANLKDISDFAGYQTEFLRLFGFGIDGVDYDQPVDVEADLPSAAQQ |
| 13 | Bacillus cereus | AAP11034.1 | MINKTLLQKRFNGAAVSYDRYANVQKKMAHSLLSILKERYSETASIRILELGCGTGYVTE QLSKLFPKSHITAVDFAESMIAIAQTRQNVKNVTFHCEDIERLRLEESYDVIISNATFQW LNNLQQVLRNLFQHLSIDGILLFSTFGHETFQELHASFQRAKEERNIKNETSIGQRFYSK DQLLHICKIETGDVHVSETCYIESFTEVKEFLHSIRKVGATNSNEGSYCQSPSLFRAMLR IYERDFTGNEGIMATYHALFIHITKEGKR |
| 14 | Escherichia coli | AAB59067.1 | MSTTHNVPQGDLVLRTLAMPADTNANGDIFGGWLMSQMDIGGAILAKEIAHGRVVTVRVE GMTFLRPVAVGDVVCCYARCVQKGTTSVSINIEVWVKKVASEPIGQRYKATEALFKYVAV DPEGKPRALPVE |

FIGURE 8 (Continued)

| SEQ ID NO | Organism | GENBANK reference | Amino acid sequence |
|---|---|---|---|
| 15 | Escherichia coli | AAA24665.1 | MSQALKNLLTLLNLEKIEEGLFRQSEDLGLRQVFGGQVVGQALYAAKETVPEERLVHSFHSYFLRPGDSKKPIIYDVETLRDGNSFSARRVAAIQNGKPIFYMTASFQAPEAGFEHQKTMPSAPAPDGLPSETQIAQSLAHLLPPVLKDKFICDRPLEVRPVEFHNPLKGHVAEPHRQVWIRANGSVPDDLRVHQYILLGYASDLNFLPVALQPHGIGFLEPGIQIATIDHSMWFHRPFNLNEWLLYSVESTSASSARGFVRGEFYTQDGVLVASTVQEGVMRNHN |
| 16 | Bacillus subtilis | CAA44858.1 | MKIYGIYMDRPLSQEENERFMSFISPEKREKCRRFYHKEDAHRTLLGDVLVRSVISRQYQLDKSDIRFSTQEYGKPCIPDLPDAHFNISHSGRWVICAFDSQPIGIDIEKTKPISLEIAKRFFSKTEYSDLLAKDKDEQTDYFYHLWSMKESFIKQEGKGLSLPLDSFSVRLHQDGQVSIELPDSHSPCYIKTYEVDPGYKMAVCAAHPDFPEDITMVSYEELL |
| 17 | Nocardia sp. NRRL 5646 | ABI83656.1 | MIETILPAGVESAELLEYPEDLKAHPAEEHLIAKSVEKRRDFIGARHCARLALAELGEPPVAIGKGERGAPIWPRGVVGSLTHCDGYRAAAVAHKMRFRSIGIDAEPHATLPEGVLDSVSLPPEREWLKTIDSALHLDRLLFCAKEATYKAWWPLTARWLGFEEAHITFEIEDGSADSGNGTFHSELLVPGQTNDGGTPLLSFDGRWLIADGFILTAIAYA |

FIGURE 11

| Sample ID | Analyte | Mwt [g/mol] | Peak Retention Time [min] | Peak Area @ 260nm [mAu] | Observed Mass (m/z) | |
|---|---|---|---|---|---|---|
| | | | | | Negative mode (M-H) | Positive mode (M+H) |
| Reference Standard | glutaryl-CoA methyl ester | 895 | 5.464 | 1879.6 | 894 | 896 |
| Biotransformation at 1 [h] time point #1 | glutaryl-CoA methyl ester | 894 | 5.513 | 303.2 | 894 | 896 |
| | glutaryl-CoA | 880 | 4.839 | 332.5 | 880 | 882 |
| Biotransformation at 1 [h] time point #2 | glutaryl-CoA methyl ester | 894 | 5.521 | 239.93 | 894 | 896 |
| | glutaryl-CoA | 880 | 4.844 | 293.6 | 880 | 882 |
| Biotransformation at 1 [h] time point #3 | glutaryl-CoA methyl ester | 894 | 5.532 | 173.8 | 894 | 896 |
| | glutaryl-CoA | 880 | 4.852 | 219.2 | 880 | 882 |
| Substrate only control (no enzyme) at 1 [h] time point | glutaryl-CoA methyl ester | 894 | 5.495 | 709.514 | 894 | 896 |
| | glutaryl-CoA | 880 | nd | nd | nd | nd |

US 9,938,543 B2

METHODS, REAGENTS AND CELLS FOR BIOSYNTHESIZING GLUTARATE METHYL ESTER

CROSS REFERENCE TO RELATED APPLICATIONS

This application claims the benefit of U.S. Provisional Application No. 62/012,722, filed Jun. 16, 2014, and U.S. Provisional Application No. 62/012,586, filed Jun. 16, 2014, the disclosures of which are incorporated by reference herein in their entireties.

TECHNICAL FIELD

This invention relates to a method of increasing the activity of a polypeptide having carboxylate reductase activity on a dicarboxylic acid by enzymatically converting the dicarboxylic acid to a methyl ester using a polypeptide having malonyl-CoA methyltransferase activity. This invention also relates to methods for biosynthesizing 2,4-pentadienoyl-CoA (e.g., as a precursor to the biosynthesis of 1,3-butadiene), and more particularly to synthesizing 2,4-pentadienoyl-CoA using one or more isolated enzymes such as one or more of a malonyl-CoA O-methyltransferase, methyl ester esterase, a carboxylate reductase, or a 5-hydroxyvaleryl-CoA dehydratase, or using recombinant host cells expressing one or more of such enzymes.

BACKGROUND 1,3-butadiene (hereinafter butadiene) is an important monomer for the production of synthetic rubbers including styrene-butadiene-rubber (SBR), polybutadiene (PB), styrene-butadiene latex (SBL), acrylonitrile-butadiene-styrene resins (ABS), nitrile rubber, and adiponitrile, which is used in the manufacture of Nylon-66 (White, Chemico-Biological Interactions, 2007, 166, 10-14).

Butadiene is typically produced as a co-product from the steam cracking process, distilled to a crude butadiene stream, and purified via extractive distillation (White, Chemico-Biological Interactions, 2007, 166, 10-14).

On-purpose butadiene has been prepared among other methods by dehydrogenation of n-butane and n-butene (Houdry process); and oxidative dehydrogenation of n-butene (Oxo-D or O-X-D process) (White, Chemico-Biological Interactions, 2007, 166, 10-14).

Industrially, 95% of global butadiene production is undertaken via the steam cracking process using petrochemical-based feedstocks such as naphtha. Production of on-purpose butadiene is not significant, given the high cost of production and low process yield (White, Chemico-Biological Interactions, 2007, 166, 10-14).

Given a reliance on petrochemical feedstocks and, for on-purpose butadiene, energy intensive catalytic steps; biotechnology offers an alternative approach via biocatalysis. Biocatalysis is the use of biological catalysts, such as enzymes, to perform biochemical transformations of organic compounds.

Accordingly, against this background, it is clear that there is a need for sustainable methods for producing intermediates wherein the methods are biocatalyst based (Jang et al., Biotechnology & Bioengineering, 2012, 109(10), 2437-2459).

SUMMARY

This disclosure is based at least in part on the development of enzymatic systems and recombinant hosts for biosynthesizing 2,4-pentadienoyl-CoA or precursors thereof, which are useful for producing, for example, 1,3-butadiene and polymers or copolymers of 1,3-butadiene. In particular, as described herein, 2,4-pentadienoyl-CoA can be biosynthetically produced from renewable feedstocks without the need for any chemical catalysts such as metal oxides. For example, in the pathways described herein, 2,4-pentadienoyl-CoA can be produced from malonyl-CoA or malonyl-[acp] via various methyl-ester shielded routes. Such methyl-ester shielded routes include using a methyl ester esterase such as a pimelyl-[acp] methyl ester esterase or esterase to hydrolyze the methyl ester of glutaryl-[acp] methyl ester, glutaryl-CoA methyl ester, glutarate methyl ester, glutarate semialdehyde methyl ester, or 5-hydroxypentanoate methyl ester, and using a 5-hydroxyvaleryl-CoA dehydratase to introduce the first terminal vinyl group of 1,3-butadiene. For example, 1,3-butadiene can be produced from precursors stemming from 2,4-pentadienoyl-CoA as outlined in FIG. 7.

In some embodiments, the C5 aliphatic backbone for conversion to 1,3-butadiene can be formed from malonyl-[acp] or malonyl-CoA via conversion to glutaryl-[acp] methyl ester or glutaryl-CoA methyl ester, followed by (i) de-esterification of glutaryl-[acp] methyl ester or glutaryl-CoA methyl ester to glutaryl-[acp] or glutaryl-CoA respectively, or (ii) hydrolysis of glutaryl-[acp] methyl ester or glutaryl-CoA methyl ester to glutarate methyl ester. See FIG. 1-3.

In some embodiments, an enzyme in the pathway generating the C5 aliphatic backbone purposefully contains irreversible enzymatic steps.

In some embodiments, the terminal carboxyl groups can be enzymatically formed using an esterase, a thioesterase, a reversible CoA-ligase, a CoA-transferase, an aldehyde dehydrogenase, a 7-oxoheptanoate dehydrogenase, a 6-oxohexanoate dehydrogenase or a 5-oxopentanoate dehydrogenase. See FIG. 4.

In some embodiments, the terminal hydroxyl group can be enzymatically formed using an alcohol dehydrogenase, a 4-hydroxybutyrate dehydrogenase, a 5-hydroxypentanoate dehydrogenase and a 6-hydroxyhexanoate dehydrogenase. See FIG. 5.

In some embodiments, the terminal vinyl group can be enzymatically formed using a 5-hydroxyvaleryl-CoA dehydratase. See FIG. 6.

In one aspect this document features a method of biosynthesizing glutarate methyl ester in a recombinant host. The method includes enzymatically converting at least one of malonyl-[acp] and malonyl-CoA to glutarate methyl ester in the host using at least one polypeptide having malonyl-CoA O-methyltransferase activity and at least one polypeptide having thioesterase activity.

In some embodiments, the malonyl-[acp] is enzymatically converted to malonyl-[acp] methyl ester using the at least one polypeptide having malonyl-CoA O-methyltransferase activity. The malonyl-[acp] methyl ester can be enzymatically converted to glutaryl-[acp] methyl ester using at least one polypeptide having an activity selected from the group consisting of synthase activity, dehydrogenase activity, dehydratase activity, and reductase activity. The glutaryl-[acp] methyl ester can be enzymatically converted to glutarate methyl ester using the at least one polypeptide having thioesterase activity.

In some embodiments, malonyl-CoA is enzymatically converted to malonyl-CoA methyl ester using the at least one polypeptide having malonyl-CoA O-methyltransferase activity. The malonyl-CoA methyl ester can be enzymatically converted to glutaryl-CoA methyl ester using at least one polypeptide having an activity selected from the group consisting of synthase activity, β-ketothiolase activity, dehydrogenase activity, hydratase activity, and reductase activity. The glutaryl-CoA methyl ester can be enzymatically converted to glutarate methyl ester using the at least one polypeptide having thioesterase activity.

The polypeptide having malonyl-CoA O-methyltransferase activity can have at least 70% sequence identity (e.g., at least 75%, 80%, 85%, 90%, 91%, 92%, 93%, 94%, 95%, 96%, 97%, 98%, 99%, or 100%) to the amino acid sequence set forth in SEQ ID NO:13.

The polypeptide having reductase activity can have at least 70% sequence identity (e.g., at least 75%, 80%, 85%, 90%, 91%, 92%, 93%, 94%, 95%, 96%, 97%, 98%, 99%, or 100%) to the amino acid sequence set forth in SEQ ID NO: 11 or 12.

In some embodiments, the method further includes enzymatically converting glutarate methyl ester to glutarate semialdehyde methyl ester in the host using at least one polypeptide having carboxylate reductase activity. The polypeptide having carboxylate reductase activity can be used in combination with a polypeptide having phosphopantetheine transferase enhancer activity.

In some embodiments, the method further includes enzymatically converting glutarate methyl ester to 5-oxopentanoic acid using at least one polypeptide having an activity selected from the group consisting of carboxylate reductase activity and esterase activity. The polypeptide having carboxylate reductase activity can be used in combination with a polypeptide having phosphopantetheine transferase enhancer activity.

In some embodiments, the method further includes enzymatically converting glutarate semialdehyde methyl ester to 5-hydroxypentanoic acid using at least one polypeptide having esterase activity. In some embodiments, the method further includes using at least one polypeptide having dehydrogenase activity to enzymatically convert glutarate semialdehyde methyl ester to 5-hydroxypentanoic acid.

The polypeptide having esterase activity can have at least 70% sequence identity (e.g., at least 75%, 80%, 85%, 90%, 91%, 92%, 93%, 94%, 95%, 96%, 97%, 98%, 99%, or 100%) to the amino acid sequence set forth in SEQ ID NO: 8.

In some embodiments, the method further includes enzymatically converting glutarate methyl ester to glutaric acid using at least one polypeptide having esterase activity. The method can further include enzymatically converting glutaric acid to 5-hydroxypentanoic acid using at least one polypeptide having carboxylate reductase activity and at least one polypeptide having dehydrogenase activity classified under EC 1.1.1.—. The polypeptide having carboxylate reductase activity can be used in combination with a polypeptide having phosphopantetheine transferase enhancer activity.

The polypeptide having carboxylate reductase activity can have at least 70% sequence identity (e.g., at least 75%, 80%, 85%, 90%, 91%, 92%, 93%, 94%, 95%, 96%, 97%, 98%, 99%, or 100%) to any one of the amino acid sequences set forth in any one of SEQ ID NOs: 2-7.

The polypeptide having thioesterase activity can have at least 70% sequence identity (e.g., at least 75%, 80%, 85%, 90%, 91%, 92%, 93%, 94%, 95%, 96%, 97%, 98%, 99%, or 100%) to any one of the amino acid sequences set forth in SEQ ID NO: 9, 10, 14 or 15.

In some embodiments, the method further includes enzymatically converting 5-hydroxypentanoic acid to 2,4-pentadienoyl-CoA using at least one polypeptide having an activity selected from the group consisting of CoA-transferase activity, a synthase activity, and dehydratase activity. A polypeptide having a CoA-transferase activity or a synthase activity and a polypeptide having dehydratase activity can enzymatically convert 5-hydroxypentanoic acid to 2,4-pentadienoyl-CoA. The method can further include enzymatically converting 2,4-pentadienoyl-CoA into 1,3 butadiene using at least one polypeptide having an activity selected from the group consisting of hydratase activity, thioesterase activity, decarboxylase activity, dehydrogenase activity, CoA-transferase activity, and dehydratase activity.

The polypeptide having thioesterase activity can have at least 70% sequence identity (e.g., at least 75%, 80%, 85%, 90%, 91%, 92%, 93%, 94%, 95%, 96%, 97%, 98%, 99%, or 100%) to any one of the amino acid sequences set forth in SEQ ID NOs: 14-15.

In another aspect, this document features a method of making glutarate. The method includes (i) enzymatically converting glutaryl-[acp] methyl ester to glutaryl-[acp] or glutaryl-CoA methyl ester to glutaryl-CoA using a polypeptide having pimeloyl-[acp] methyl ester methylesterase activity, and (ii) enzymatically converting glutaryl-[acp] or glutaryl-CoA to glutarate using at least one polypeptide having thioesterase activity, reversible CoA-ligase activity, a CoA-transferase activity, an acylating dehydrogenase activity, an aldehyde dehydrogenase activity, a glutarate semialdehyde dehydrogenase activity, or a succinate-semialdehyde dehydrogenase activity.

The polypeptide having pimeloyl-[acp] methyl ester methylesterase activity can have at least 70% sequence identity (e.g., at least 75%, 80%, 85%, 90%, 91%, 92%, 93%, 94%, 95%, 96%, 97%, 98%, 99%, or 100%) to the amino acid sequence set forth in SEQ ID NO: 1.

In some embodiments, glutaryl-[acp] or glutaryl-CoA is enzymatically converted to glutaric acid using a polypeptide having thioesterase activity. In some embodiments, glutaryl-[acp] or glutaryl-CoA is enzymatically converted to glutaric acid using a polypeptide having reversible CoA-ligase activity or a CoA-transferase activity. In some embodiments, glutaryl-[acp] or glutaryl-CoA is enzymatically converted to glutaric acid using a polypeptide having an acylating dehydrogenase activity, an aldehyde dehydrogenase activity, a glutarate semialdehyde dehydrogenase activity, or a succinate-semialdehyde dehydrogenase activity.

In another aspect, this document features a recombinant host cell. The recombinant host cell includes at least one exogenous nucleic acid encoding a polypeptide having malonyl-CoA O-methyltransferase activity and a polypeptide having thioesterase activity, the host producing glutarate methyl ester.

The host can further include an exogenous polypeptide having carboxylate reductase activity, the host further producing glutarate semialdehyde methyl ester. In some embodiments, the host furthers include one or more exogenous polypeptides having an activity selected from the group consisting of synthase activity, dehydrogenase activity, dehydratase activity, and reductase activity. In some embodiments, the host further includes one or more exogenous polypeptides having an activity selected from the group consisting of synthase activity, β-ketothiolase activity, dehydrogenase activity, hydratase activity, and reductase activity.

The polypeptide having malonyl-CoA O-methyltransferase activity can have at least 70% sequence identity (e.g., at least 75%, 80%, 85%, 90%, 91%, 92%, 93%, 94%, 95%, 96%, 97%, 98%, 99%, or 100%) to the amino acid sequence set forth in SEQ ID NO: 13.

The polypeptide having thioesterase activity can have at least 70% sequence identity (e.g., at least 75%, 80%, 85%, 90%, 91%, 92%, 93%, 94%, 95%, 96%, 97%, 98%, 99%, or 100%) to any one of the amino acid sequences set forth in any one of SEQ ID NOs: 14-15.

The polypeptide having reductase activity can have at least 70% sequence identity (e.g., at least 75%, 80%, 85%, 90%, 91%, 92%, 93%, 94%, 95%, 96%, 97%, 98%, 99%, or 100%) to any one of the amino acid sequences set forth in SEQ ID NOs: 11 or 12.

The host can further include an exogenous polypeptide having esterase activity, the host further producing glutaric acid or 5-oxopentanoic acid.

In some embodiments, the host includes one or more exogenous polypeptides having an activity selected from the group consisting of esterase activity, 6-hydroxyhexanoate dehydrogenase activity, 4-hydroxybutyrate dehydrogenase activity, 5-hydroxypentanoate dehydrogenase activity, and alcohol dehydrogenase activity, the host producing 5-hydroxypentanoic acid. The host can further include one or more exogenous polypeptides having an activity selected from the group consisting of CoA-transferase activity, a synthase activity, and dehydratase activity, the host producing 2,4-pentadienoyl-CoA from 5-hydroxypentanoic acid. The host can further include one or more exogenous polypeptides having an activity selected from the group consisting of hydratase activity, thioesterase activity, decarboxylase activity, dehydrogenase activity, CoA-transferase activity, and dehydratase activity, the host producing 1,3-butadiene from 2,4-pentadienoyl-CoA.

The polypeptide having thioesterase activity can at least 70% sequence identity (e.g., at least 75%, 80%, 85%, 90%, 91%, 92%, 93%, 94%, 95%, 96%, 97%, 98%, 99%, or 100%) to the amino acid sequence set forth in SEQ ID NO: 14 or SEQ ID NO: 15

The polypeptide having carboxylate reductase activity can have at least 70% sequence identity (e.g., at least 75%, 80%, 85%, 90%, 91%, 92%, 93%, 94%, 95%, 96%, 97%, 98%, 99%, or 100%) to any one of the amino acid sequences set forth in any one of SEQ ID NOs: 2-7.

In some embodiments, when the host includes an exogenous polypeptide having carboxylate reductase activity it is used in combination with an exogenous polypeptide having phosphopantetheine transferase enhancer activity.

In another aspect, this document features a recombinant host including at least one exogenous nucleic acid encoding a polypeptide having pimeloyl-[acp] methyl ester methylesterase activity, and at least one polypeptide having an activity selected from the group consisting of thioesterase activity, reversible CoA-ligase activity, a CoA-transferase activity, an acylating dehydrogenase activity, an aldehyde dehydrogenase activity, a glutarate semialdehyde dehydrogenase activity, and a succinate-semialdehyde dehydrogenase activity.

The polypeptide having pimeloyl-[acp] methyl ester methylesterase activity can have at least 70% sequence identity (e.g., at least 75%, 80%, 85%, 90%, 91%, 92%, 93%, 94%, 95%, 96%, 97%, 98%, 99%, or 100%) to the amino acid sequence set forth in SEQ ID NO: 1.

In some embodiments, when the host includes an exogenous polypeptide having carboxylate reductase activity it is used in combination with an exogenous polypeptide having phosphopantetheine transferase enhancer activity.

In another aspect, this document features a bio-derived product, bio-based product or fermentation-derived product, wherein the product includes (i.) a composition including at least one bio-derived, bio-based or fermentation-derived compound as described herein, or any combination thereof; (ii.) a bio-derived, bio-based or fermentation-derived polymer including the bio-derived, bio-based or fermentation-derived composition or compound of (i.), or any combination thereof; (iii.) a bio-derived, bio-based or fermentation-derived resin including the bio-derived, bio-based or fermentation-derived compound or bio-derived, bio-based or fermentation-derived composition of (i.) or any combination thereof or the bio-derived, bio-based or fermentation-derived polymer of ii. or any combination thereof; (iv.) a molded substance obtained by molding the bio-derived, bio-based or fermentation-derived polymer of (ii.) or the bio-derived, bio-based or fermentation-derived resin of (iii.), or any combination thereof; (v.) a bio-derived, bio-based or fermentation-derived formulation including the bio-derived, bio-based or fermentation-derived composition of (i.), bio-derived, bio-based or fermentation-derived compound of (i.), bio-derived, bio-based or fermentation-derived polymer of (ii.), bio-derived, bio-based or fermentation-derived resin of (iii.), or bio-derived, bio-based or fermentation-derived molded substance of (iv.), or any combination thereof; or (vi.) a bio-derived, bio-based or fermentation-derived semi-solid or a non-semi-solid stream, including the bio-derived, bio-based or fermentation-derived composition of (i.), bio-derived, bio-based or fermentation-derived compound of (i.), bio-derived, bio-based or fermentation-derived polymer of (ii.), bio-derived, bio-based or fermentation-derived resin of (iii.), bio-derived, bio-based or fermentation-derived formulation of (v.), or bio-derived, bio-based or fermentation-derived molded substance of (iv.), or any combination thereof.

This document also features a method of increasing the activity of a polypeptide having carboxylate reductase activity on a substituted or unsubstituted $C_4$-$C_8$ dicarboxylic acid such as glutaric acid or adipic acid. The method includes enzymatically converting the $C_4$-$C_8$ dicarboxylic acid to a $HOC(=O)(C_2$-$C_6$ alkyl)-$C(=O)OCH_3$ ester using a polypeptide having malonyl-CoA methyltransferase activity before enzymatically converting the $HOC(=O)(C_2$-$C_6$ alkyl)-$C(=O)OCH_3$ ester to a $HC(=O)(C_2$-$C_6$ alkyl)-$C(=O)OCH_3$ using a polypeptide having carboxylate reductase activity. The method further can include enzymatically converting the $HC(=O)(C_2$-$C_6$ alkyl)-$C(=O)OCH_3$ to $HOCH_2(C_2$-$C_6$ alkyl)-$C(=O)OCH_3$ using a polypeptide having dehydrogenase activity. In some embodiments, the method further includes enzymatically converting the $HOCH_2(C_2$-$C_6$ alkyl)-$C(=O)OCH_3$ product to a $HOCH_2(C_2$-$C_6$ alkyl)-$C(=O)OH$ product using a polypeptide having the activity of an esterase.

This document also features a recombinant host that includes at least one exogenous nucleic acid encoding a (i) malonyl-[acp] O-methyltransferase, (ii) a pimeloyl-[acp] methyl ester methylesterase and (iii) a thioesterase, and produce glutarate methyl ester, glutaryl-[acp] or glutaryl-CoA.

Such a recombinant host producing glutarate methyl ester further can include an esterase, and further produce glutaric acid.

Such a recombinant host producing glutaryl-[acp] further can include a thioesterase and produce glutaric acid.

Such a recombinant host producing glutaryl-CoA further can include one or more of (i) a thioesterase, (ii) a reversible CoA-ligase, (iii) a CoA-transferase, or (iv) an acylating dehydrogenase, and (v) an aldehyde dehydrogenase such as such as 7-oxoheptanoate dehydrogenase, 6-oxohexanoate dehydrogenase or 5-oxopentanoate dehydrogenase and further produce glutaric acid or 5-oxopentanoate.

A recombinant host producing 5-oxopentanoate or glutaric acid further can include one or more of (i) an alcohol dehydrogenase or (ii) a carboxylate reductase and further produce 5-hydroxypentanoate.

A recombinant host producing glutarate methyl ester further can include one or more of (i) an alcohol dehydrogenase, (ii) an esterase or (iii) a carboxylate reductase and further produce 5-hydroxypentanoate.

In another aspect, this document features a method for producing a bioderived four or five carbon compound. The method includes culturing or growing a host as described herein under conditions and for a sufficient period of time to produce the bioderived four or five carbon compound, wherein, optionally, the bioderived four or five carbon compound can be selected from the group consisting of 2,4-pentadienoyl-CoA, glutaryl-[acp] methyl ester, 5-hydroxypentanoic acid, 3-buten-2-one, 3-buten-2-ol, 1,3-butadiene and combinations thereof.

In another aspect, this document features a composition including a bioderived for or five carbon compound and a compound other than the bioderived four or fivecarbon compound, wherein the bioderived four or five carbon compound is selected from the group consisting of 2,4-pentadienoyl-CoA, glutaryl-[acp] methyl ester, 5-hydroxypentanoic acid, 3-buten-2-one, 3-buten-2-ol, 1,3-butadiene and combinations thereof. For example, the bioderived 4-carbon compound can be a cellular portion of a host cell or an organism.

This document also features a biobased polymer including the bioderived four or five carbon compound including 2,4-pentadienoyl-CoA, glutaryl-[acp] methyl ester, 5-hydroxypentanoic acid, 3-buten-2-one, 3-buten-2-ol, 1,3-butadiene and combinations thereof.

This document also features biobased resin including the bioderived four or five carbon compound including 2,4-pentadienoyl-CoA, glutaryl-[acp] methyl ester, 5-hydroxypentanoic acid, 3-buten-2-one, 3-buten-2-ol, 1,3-butadiene and combinations thereof, as well as a molded product obtained by molding a biobased resin.

In another aspect this document also features a process for producing a biobased polymer including chemically reacting the bioderived four or five carbon compound with itself or another compound in a polymer-producing reaction.

In another aspect this document features a process for producing a biobased resin as described herein including chemically reacting the bioderived four or five carbon compound with itself or another compound in a resin producing reaction.

This document also features a biochemical network including a malonyl-CoA O-methyltransferase, wherein the malonyl-CoA O-methyltransferase enzymatically converts malonyl-[acp] to malonyl-[acp] methyl ester. The biochemical network can further include a synthase, a dehydrogenase, a dehydratase, a reductase, and a thioesterase, wherein the synthase, the dehydrogenase, the dehydratase, the reductase, and the thioesterase, enzymatically convert the malonyl-[acp] methyl ester to glutarate methyl ester.

In some embodiments the biochemical network further includes a carboxylate reductase, wherein the carboxylate reductase enzymatically converts glutarate methyl ester to glutarate semialdehyde methyl ester. The biochemical network can further include an esterase and a dehydrogenase, wherein the esterase and dehydrogenase enzymatically convert glutarate semialdehyde methyl ester to 5-hydroxypentanoic acid.

In some embodiments, the biochemical network can further include a CoA-transferase and dehydratase, wherein the CoA-transferase and dehydratase enzymatically convert 5-hydroxypentanoic acid to 2,4-pentadienoyl-CoA. The biochemical network can further include a hydratase, a thioesterase, a decarboxylase, a dehydrogenase, a CoA-transferase, and a dehydratase, wherein the hydratase, the thioesterase, the decarboxylase, the dehydrogenase, the CoA-transferase, and the dehydratase enzymatically convert the 2,4-pentadienoyl-CoA to 1,3-butadiene.

This document also features a biochemical network including a malonyl-CoA O-methyltransferase, wherein the malonyl-CoA O-methyltransferase enzymatically converts malonyl-CoA to malonyl-CoA methyl ester. The biochemical network can further include a synthase, a β-ketothiolase, a dehydrogenase, a hydratase, a reductase, and a thioesterase, wherein the synthase, the β-ketothiolase, the dehydrogenase, the hydratase, the reductase, and the thioesterase, enzymatically convert the malonyl-CoA methyl ester to glutarate methyl ester.

In some embodiments the biochemical network further includes a carboxylate reductase, wherein the carboxylate reductase enzymatically converts glutarate methyl ester to glutarate semialdehyde methyl ester. The biochemical network can further include an esterase and a dehydrogenase, wherein the esterase and dehydrogenase enzymatically convert glutarate semialdehyde methyl ester to 5-hydroxypentanoic acid.

In some embodiments, the biochemical network can further include a CoA-transferase and dehydratase, wherein the CoA-transferase and dehydratase enzymatically convert 5-hydroxypentanoic acid to 2,4-pentadienoyl-CoA. The biochemical network can further include a hydratase, a thioesterase, a decarboxylase, a dehydrogenase, a CoA-transferase, and a dehydratase, wherein the hydratase, the thioesterase, the decarboxylase, the dehydrogenase, the CoA-transferase, and the dehydratase enzymatically convert the 2,4-pentadienoyl-CoA to 1,3-butadiene.

This document also features a method of increasing the activity of a polypeptide having carboxylate reductase activity on a substituted or unsubstituted C4-C8 dicarboxylic acid such as glutaric acid or adipic acid. The method includes enzymatically converting the $C_4$-$C_8$ dicarboxylic acid to a $HOC(=O)(C_2$-$C_6$ alkyl)-$C(=O)OCH_3$ ester using a polypeptide having malonyl-CoA methyltransferase activity before enzymatically converting the $HOC(=O)(C_2$-$C_6$ alkyl)-$C(=O)OCH_3$ ester to a $HC(=O)(C_2$-$C_6$ alkyl)-$C(=O)OCH_3$ using a polypeptide having carboxylate reductase activity. The method further can include enzymatically converting the $HC(=O)(C_2$-$C_6$ alkyl)-$C(=O)OCH_3$ to $HOCH_2(C_2$-$C_6$ alkyl)-$C(=O)OCH_3$ using a polypeptide having dehydrogenase activity. In some embodiments, the method further includes enzymatically converting the $HOCH_2(C_2$-$C_6$ alkyl)-$C(=O)OCH_3$ product to a $HOCH_2(C_2$-$C_6$ alkyl)-$C(=O)OH$ product using a polypeptide having the activity of an esterase.

Any of the methods can be performed in a recombinant host by fermentation. The host can be subjected to a cultivation strategy under aerobic, anaerobic, or micro-aerobic cultivation conditions. The host can be cultured under conditions of nutrient limitation such as phosphate, oxygen or nitrogen limitation. The host can be retained using a ceramic membrane to maintain a high cell density during fermentation.

In some embodiments, the host is subjected to a cultivation strategy under aerobic or micro-aerobic cultivation conditions.

In some embodiments, a biological feedstock can be used as the principal carbon source for the fermentation. For example, the biological feedstock can be, or can derive from monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, a non-biological feedstock can be used as the principal carbon source for the fermentation. The non-biological feedstock can be, or can be derived from, natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

In any of the embodiments described herein, the host can be a prokaryote. The prokaryote can be selected from the group consisting of *Escherichia; Clostridia; Corynebacteria; Cupriavidus; Pseudomonas; Delftia; Bacilluss; Lactobacillus; Lactococcus*; and *Rhodococcus*. For example, the prokaryote can be selected from the group consisting of *Escherichia coli, Clostridium ljungdahlii, Clostridium autoethanogenum, Clostridium kluyveri, Corynebacterium glutamicum, Cupriavidus necator, Cupriavidus metallidurans. Pseudomonas fluorescens, Pseudomonas putida, Pseudomonas oleavorans, Delftia acidovorans, Bacillus subtillis, Lactobacillus delbrueckii, Lactococcus lactis*, and *Rhodococcus equi*.

In any of the embodiments described herein, the host can be a eukaryote. The eukaryote can selected from the group consisting of *Aspergillus, Saccharomyces, Pichia, Yarrowia, Issatchenkia, Debaryomyces, Arxula*, and *Kluyveromyces*. For example, the eukaryote can be selected from the group consisting of *Aspergillus niger, Saccharomyces cerevisiae, Pichia pastoris, Yarrowia lipolytica, Issathenkia orientalis, Debaryomyces hansenii, Arxula adenoinivorans*, and *Kluyveromyces lactis*.

In some embodiments, the host exhibits tolerance to high concentrations of a C5 building block, and wherein the tolerance to high concentrations of a C5 building block is improved through continuous cultivation in a selective environment.

In some embodiments, the host's endogenous biochemical network is attenuated or augmented to (1) ensure the intracellular availability of acetyl-CoA, (2) create a cofactor, i.e. NADH or NADPH, imbalance that may be balanced via the formation of glutarate methyl ester, 2,4-pentadienoyl-CoA, or 1,3-butadiene, (3) prevent degradation of central metabolites, central precursors leading to and including glutarate methyl ester, 2,4-pentadienoyl-CoA, or 1,3-butadiene and (4) ensure efficient efflux from the cell.

In some embodiments, the host includes one or more of the following: the intracellular concentration of oxaloacetate for biosynthesis of a C5 building block is increased in the host by overexpressing recombinant genes forming oxaloacetate; wherein an imbalance in NADPH is generated that can be balanced via the formation of a C5 building block; wherein an exogenous lysine biosynthesis pathway synthesizing lysine from 2-oxoglutarate via 2-oxoadipate is introduced in a host using the meso 2,6 diaminopimelate pathway for lysine synthesis; wherein an exogenous lysine biosynthesis pathway synthesizing lysine from oxaloacetate to meso 2,6 diaminopimelate is introduced in a host using the 2-oxoadipate pathway for lysine synthesis; wherein endogenous degradation pathways of central metabolites and central precursors leading to and including C5 building blocks are attenuated in the host; or wherein the efflux of a C5 building block across the cell membrane to the extracellular media is enhanced or amplified by genetically engineering structural modifications to the cell membrane or increasing any associated transporter activity for a C5 building block.

Any of the recombinant hosts described herein further can include one or more of the following attenuated polypeptides having attenuated activity of a: polyhydroxyalkanoate synthase, an acetyl-CoA thioesterase, an acetyl-CoA specific β-ketothiolase, an acetoacetyl-CoA reductase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, a transhydrogenase dissipating the cofactor imbalance, aglutamate dehydrogenase specific for the cofactor for which an imbalance is created, a NADH/NADPH-utilizing glutamate dehydrogenase, a pimeloyl-CoA dehydrogenase; an acyl-CoA dehydrogenase accepting C5 building blocks and central precursors as substrates; a glutaryl-CoA dehydrogenase; or a pimeloyl-CoA synthetase.

Any of the recombinant hosts described herein further can overexpress one or more genes encoding a polypeptide having: an acetyl-CoA synthetase, a 6-phosphogluconate dehydrogenase; a transketolase; a feedback resistant threonine deaminase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a propionyl-CoA synthetase; a L-alanine dehydrogenase; a L-glutamate dehydrogenase; a L-glutamine synthetase; a lysine transporter; a dicarboxylate transporter; and/or a multidrug transporter activity.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from of the above types of host cells and used in a purified or semi-purified form. Extracted enzymes can optionally be immobilized to the floors and/or walls of appropriate reaction vessels. Moreover, such extracts include lysates (e.g. cell lysates) that can be used as sources of relevant enzymes. In the methods provided by the document, all the steps can be performed in cells (e.g., host cells), all the steps can be performed using extracted enzymes, or some of the steps can be performed in cells and others can be performed using extracted enzymes.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein including GenBank and NCBI submissions with accession numbers are incorporated by reference in their entirety. In case of conflict, the present specification, including definitions, will control. In addition, the materials, methods, and examples are illustrative only and not intended to be limiting.

One of skill in the art understands that compounds containing carboxylic acid groups (including, but not limited to, organic monoacids, hydroxyacids, aminoacids, and dicarboxylic acids) are formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free acid by reducing the pH to below the pKa, through addition of acid or treatment with an acidic ion exchange resin.

One of skill in the art understands that compounds containing amine groups (including, but not limited to, organic amines, aminoacids, and diamines) are formed or converted to their ionic salt form, for example, by addition of an acidic proton to the amine to form the ammonium salt, formed with inorganic acids such as hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free amine by raising the pH to above the pKb through addition of base or treatment with a basic ion exchange resin.

One of skill in the art understands that compounds containing both amine groups and carboxylic acid groups (including, but not limited to, aminoacids) are formed or converted to their ionic salt form by either 1) acid addition salts, formed with inorganic acids including, but not limited to, hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like, or 2) when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt can of the present invention is isolated as a salt or converted to the free acid by reducing the pH to below the pKa through addition of acid or treatment with an acidic ion exchange resin.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

DESCRIPTION OF DRAWINGS

FIG. 8 contains the amino acid sequences of an *Escherichia coli* pimeloyl-[acp] methyl ester methylesterase (see Genbank Accession No. AAC76437.1, SEQ ID NO: 1), a *Mycobacterium marinum* carboxylate reductase (see Genbank Accession No. ACC40567.1, SEQ ID NO: 2), a *Mycobacterium smegmatis* carboxylate reductase (see Genbank Accession No. ABK71854.1, SEQ ID NO: 3), a *Segniliparus rugosus* carboxylate reductase (see Genbank Accession No. EFV11917.1, SEQ ID NO: 4), a *Mycobacterium smegmatis* carboxylate reductase (see Genbank Accession No. ABK75684.1, SEQ ID NO: 5), a *Mycobacterium massiliense* carboxylate reductase (see Genbank Accession No. EIV11143.1, SEQ ID NO: 6), a *Segniliparus rotundus* carboxylate reductase (see Genbank Accession No. ADG98140.1, SEQ ID NO: 7), an *Pseudomonas fluorescens* esterase (see Genbank Accession No. AAC60471.2, SEQ ID NO: 8), a *Lactobacillus brevis* acyl-[acp] thioesterase (see Genbank Accession NO: ABJ63754.1, SEQ ID NO:9), a *Lactobacillus plantarum* acyl-[acp] thioesterase (see Genbank Accession Nos. CCC78182.1, SEQ ID NO: 10), a *Treponema denticola* enoyl-CoA reductase (see, e.g., Genbank Accession No. AAS11092.1, SEQ ID NO: 11), an *Euglena gracilis* enoyl-CoA reductase (see, e.g., Genbank Accession No. AAW66853.1, SEQ ID NO: 12), a *Bacillus cereus* malonyl-[acp] O-methyltransferase (see, e.g., Genbank Accession No. AAP11034.1, SEQ ID NO: 13), an *Escherichia coli* thioesterase (see, e.g., Genbank Accession No. AAB59067.1, SEQ ID NO: 14), and an *Escherichia coli* thioesterase (see, e.g., Genbank Accession No. AAA24665.1, SEQ ID NO: 15), a *Bacillus subtilis* phosphopantetheinyl transferase (see Genbank Accession No. CAA44858.1, SEQ ID NO:16), a *Nocardia* sp. NRRL 5646 phosphopantetheinyl transferase (see Genbank Accession No. ABI83656.1, SEQ ID NO:17)

FIG. 11 is a table of conversion after 1 hour of glutaryl-CoA methyl ester to glutaryl-CoA by pimeloyl-[acp] methyl ester methylesterase.

DETAILED DESCRIPTION

Figure 1:
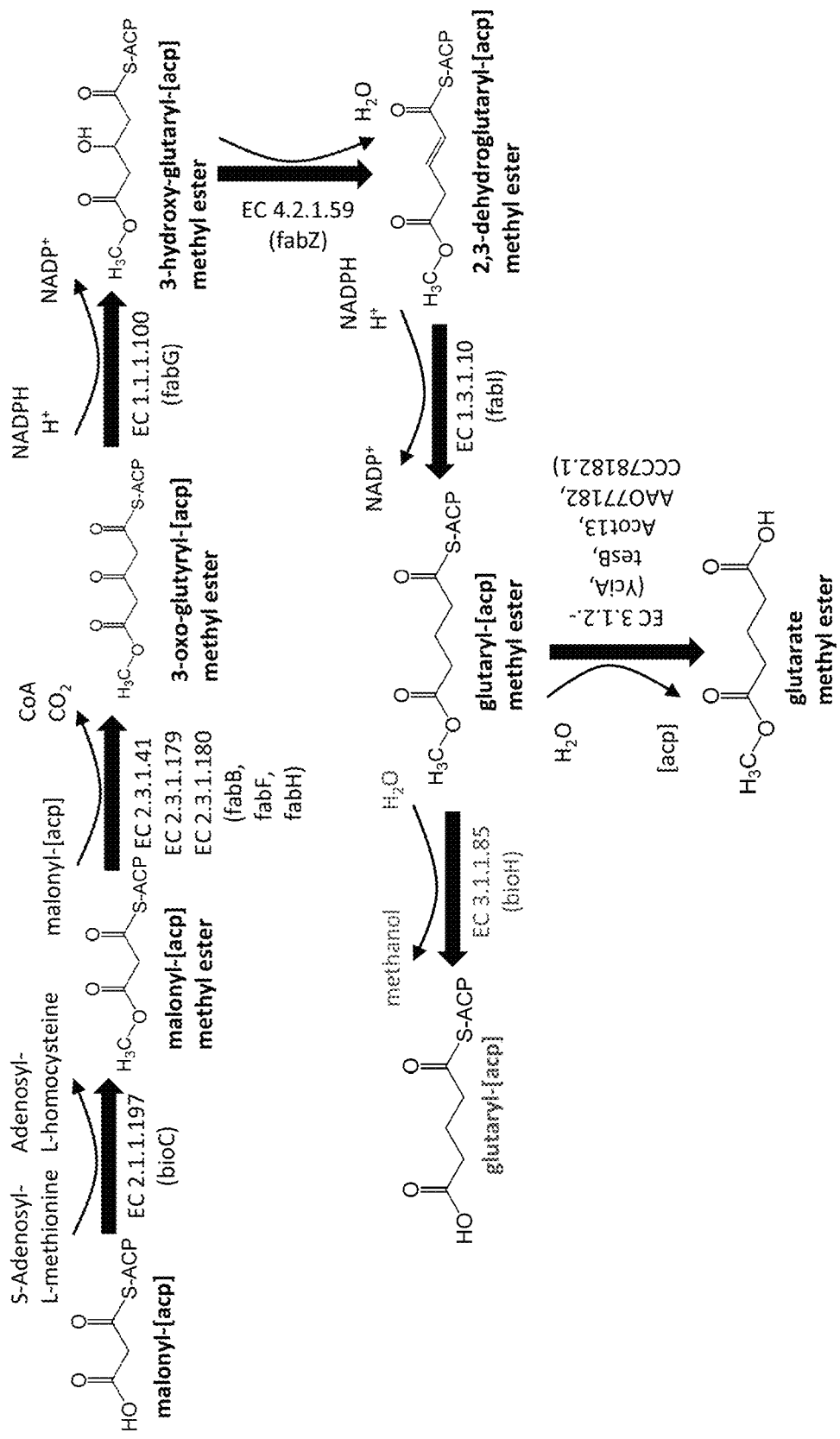
FIG. 1 is a schematic of exemplary biochemical pathways leading to glutarate methyl ester or glutaryl-[acp] from malonyl-[acp].

This document provides enzymes, non-natural pathways, cultivation strategies, feedstocks, host microorganisms and attenuations to the host's biochemical network, which can be used to synthesize 2,4-pentadienoyl-CoA and, optionally, 1,3-butadiene (also known as buta-1,3-diene, biethylene, or vinylethylene) from central precursors or central metabolites. Production of butadiene thus can proceed through a common intermediate, 2,4-pentadienoyl-CoA, even though there are a number of different feedstocks and different pathways that can be used to produce 2,4-pentadienoyl-CoA. For example, malonyl-CoA or malonyl-[acp] can be used to produce 2,4-pentadienoyl-CoA via different methyl-ester shielded routes. As used herein, the term "central precursor" is used to denote any metabolite in any metabolic pathway shown herein leading to the synthesis of 5-hydroxypentanoate, 2,4-pentadienoyl-CoA or butadiene. The term "central metabolite" is used herein to denote a metabolite that is produced in all microorganisms to support growth.

As such, host microorganisms described herein can include endogenous pathways that can be manipulated such that 2,4-pentadienoyl-CoA can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in the host including a malonyl-[acp] O-methyltransferase, a pimeloyl-[acp] methyl ester methylesterase, an esterase, a reversible CoA-ligase, CoA-transferase, a 4-hydroxybutyrate dehydrogenase, a 5-hydroxypentanoate dehydrogenase, a 6-hydroxyhexanoate dehydrogenase, an alcohol dehydrogenase, a 5-oxopentanoate dehydrogenase, a 6-oxohexanoate dehydrogenase, a 7-oxoheptanoate dehydrogenase, an aldehyde dehydrogenase, or a carboxylate reductase. In recombinant hosts expressing a carboxylate reductase, a phosphopantetheinyl transferase also can be expressed as it enhances activity of the carboxylate reductase.

This document also features a recombinant host that includes at least one exogenous nucleic acid encoding (i) a polypeptide having malonyl-[acp] O-methyltransferase activity, (ii) a polypeptide having pimeloyl-[acp] methyl ester methylesterase activity and (iii) a polypeptide having thioesterase activity, and produce glutarate methyl ester, glutaryl-[acp] or glutaryl-CoA.

Such a recombinant host producing glutarate methyl ester further can include a polypeptide having esterase activity, and further produce glutaric acid.

Such a recombinant host producing glutaryl-[acp] further can include a polypeptide having thioesterase activity and produce glutaric acid.

Such a recombinant host producing glutaryl-CoA further can include one or more of (i) a polypeptide having thioesterase activity, (ii) a polypeptide having reversible CoA-ligase activity, (iii) a polypeptide having CoA-transferase activity, or (iv) a polypeptide having acylating dehydrogenase activity, and (v) a polypeptide having aldehyde dehydrogenase activity such as a 7-oxoheptanoate dehydrogenase, 6-oxohexanoate dehydrogenase or 5-oxopentanoate dehydrogenase activity and further produce glutaric acid or 5-oxopentanoate.

A recombinant host producing 5-oxopentanoate or glutaric acid further can include one or more of (i) a polypeptide having alcohol dehydrogenase activity or (ii) a polypeptide having carboxylate reductase activity and further produce 5-hydroxypentanoate.

A recombinant host producing glutarate methyl ester further can include one or more of (i) a polypeptide having alcohol dehydrogenase activity, (ii) a polypeptide having esterase activity or (iii) a polypeptide having carboxylate reductase activity and further produce 5-hydroxypentanoate.

Within an engineered pathway, the enzymes can be from a single source, i.e., from one species or genus, or can be from multiple sources, i.e., different species or genera. Nucleic acids encoding the enzymes described herein have been identified from various organisms and are readily available in publicly available databases such as GenBank or EMBL.

Any of the enzymes described herein that can be used for production of one or more C5 building blocks can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a polypeptide having pimeloyl-[acp] methyl ester methylesterase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* (see Genbank Accession Nos. AAC76437.1, SEQ ID NO: 1) pimeloyl-[acp] methyl ester methylesterase. See FIG. 1-3.

For example, a polypeptide having carboxylate reductase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Segniliparus rugosus* (see Genbank Accession No. EFV11917.1, SEQ ID NO: 4), a *Mycobacterium smegmatis* (see Genbank Accession No. ABK75684.1, SEQ ID NO: 5), a *Mycobacterium massiliense* (see Genbank Accession No. EIV11143.1, SEQ ID NO: 6), or a *Segniliparus rotundus* (see Genbank Accession No. ADG98140.1, SEQ ID NO: 7) carboxylate reductase. See, FIG. 5.

For example, a polypeptide having phosphopantetheinyl transferase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Bacillus subtilis* phosphopantetheinyl transferase (see Genbank Accession No. CAA44858.1, SEQ ID NO: 16) or a *Nocardia* sp. NRRL 5646 phosphopantetheinyl transferase (see Genbank Accession No. ABI83656.1, SEQ ID NO: 17). See FIG. 5.

For example, a polypeptide having esterase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Pseudomonas fluorescens* esterase (see Genbank Accession Nos. AAC60471.2, SEQ ID NO: 8). See FIG. 4, 5.

For example, a polypeptide having thioesterase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Lactobacillus brevis* acyl-[acp] thioesterase (see Genbank Accession Nos. ABJ63754.1, SEQ ID NO: 9), a *Lactobacillus plantarum* acyl-[acp] thioesterase (see Genbank Accession Nos. CCC78182.1, SEQ ID NO: 10), or a *Escherichia coli* thioesterase (see Genbank Accession Nos. AAB59067.1 or AAA24665.1, SEQ ID NO: 14 or 15). See FIG. 4.

For example, a polypeptide having malonyl-[acp] O-methyltransferase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Bacillus cereus* (see Genbank Accession Nos. AAP11034.1, SEQ ID NO: 13) malonyl-[acp] O-methyltransferase. See FIG. 1-3.

For example, a polypeptide having enoyl-CoA reductase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Treponema denticola* (see Genbank Accession Nos. AAS11092.1, SEQ ID NO:11), or a *Euglena gracilis* (see Genbank Accession Nos. AAW66853.1, SEQ ID NO:12) enoyl-CoA reductase. See FIGS. 1-3.

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: —i is set to a file containing the first amino acid sequence to be compared (e.g., C:\seq1.txt); —j is set to a file containing the second amino acid sequence to be compared (e.g., C:\seq2.txt); —p is set to blastp; —o is set to any desired file name (e.g., C:\output.txt); and all other options are left at their default setting. For example, the following command can be used to generate an output file containing a comparison between two amino acid sequences: C:\Bl2seq-i c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more polypeptide having the activity of a reductase, deacetylase, N-acetyltransferase, malonyl-[acp] O-methyltransferase, esterase, thioesterase, hydratase, dehydrogenase, CoA-ligase, and/or CoA-transferase as described herein.

In addition, the production of one or more C5 building blocks can be performed in vitro using the isolated enzymes described herein, using a lysate (e.g., a cell lysate) from a host microorganism as a source of the enzymes, or using a plurality of lysates from different host microorganisms as the source of the enzymes.

Figure 4:
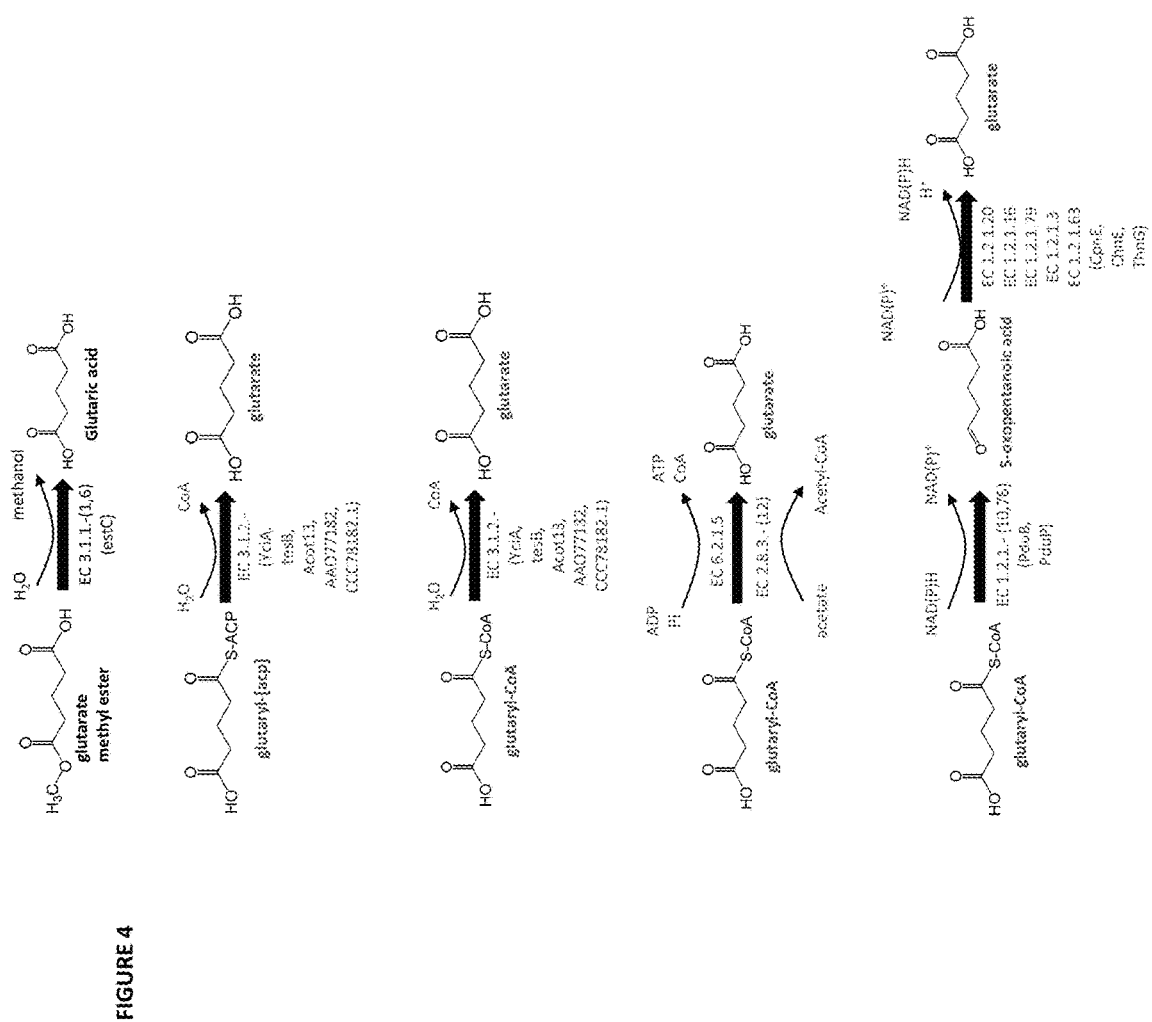
FIG. 4 is a schematic of exemplary biochemical pathways leading to glutarate using glutarate methyl ester, glutaryl-[acp] or glutaryl-CoA as central precursor.

Enzymes Generating the Terminal Carboxyl Groups in the Biosynthesis of 2,4-Pentadienoyl-CoA As depicted in FIG. 4, a terminal carboxyl group can be enzymatically formed using (i) a polypeptide having thioesterase activity, (ii) a polypeptide having reversible CoA-ligase activity, (iii) a polypeptide having CoA-transferase activity, (iv) a polypeptide having acylating dehydrogenase activity, or (v) a polypeptide having aldehyde dehydrogenase activity such as a 7-oxoheptanoate dehydrogenase, a 6-oxohexanoate dehydrogenase, or a 5-oxopentanoate dehydrogenase activity, or (vi) a polypeptide having esterase activity.

In some embodiments, a terminal carboxyl group leading to the synthesis of glutarate is enzymatically formed by a thioesterase classified under EC 3.1.2.—, such as the gene product of YciA (SEQ ID NO: 14), tesB (Genbank Accession No. AAA24665.1, SEQ ID NO: 15) or Acot13 (see, for example, Cantu et al., *Protein Science*, 2010, 19, 1281-1295; Zhuang et al., *Biochemistry*, 2008, 47(9), 2789-2796; or Naggert et al., *J. Biol. Chem.*, 1991, 266(17), 11044-11050).

In some embodiments, the second terminal carboxyl group leading to the synthesis of glutaric acid is enzymatically formed by a CoA-transferase such as a glutaconate CoA-transferase classified, for example, under EC 2.8.3.12 such as from *Acidaminococcus fermentans*. See, for example, Buckel et al., 1981, *Eur. J. Biochem.*, 118:315-321. FIG. 4.

In some embodiments, the second terminal carboxyl group leading to the synthesis of glutaric acid is enzymatically formed by a reversible CoA-ligase such as a succinate-CoA ligase classified, for example, under EC 6.2.1.5 such as from *Thermococcus kodakaraensis*. See, for example, Shikata et al., 2007, *J. Biol. Chem.*, 282(37):26963-26970.

In some embodiments, the second terminal carboxyl group leading to the synthesis of glutaric acid is enzymatically formed by an acyl-[acp] thioesterase classified under EC 3.1.2.—, such as the acyl-[acp] thioesterase from *Lactobacillus brevis* (GenBank Accession No. ABJ63754.1, SEQ ID NO: 9) or from *Lactobacillus plantarum* (GenBank Accession No. CCC78182.1, SEQ ID NO: 10). Such acyl-[acp] thioesterases have C6-C8 chain length specificity (see, for example, Jing et al., 2011, *BMC Biochemistry*, 12(44)). See, e.g., FIG. 4.

In some embodiments, the second terminal carboxyl group leading to the synthesis of glutaric acid is enzymatically formed by an aldehyde dehydrogenase classified, for example, under EC 1.2.1.3 (see, Guerrillot & Vandecasteele, *Eur. J. Biochem.*, 1977, 81, 185-192). See, FIG. 4.

In some embodiments, the second terminal carboxyl group leading to the synthesis of glutaric acid is enzymatically formed by an aldehyde dehydrogenase classified under EC 1.2.1.—such as a glutarate semialdehyde dehydrogenase classified, for example, under EC 1.2.1.20, a succinate-semialdehyde dehydrogenase classified, for example, under EC 1.2.1.16 or EC 1.2.1.79, or an aldehyde dehydrogenase classified under EC 1.2.1.3. For example, an aldehyde dehydrogenase classified under EC 1.2.1.—can be a 5-oxopentanoate dehydrogenase such as the gene product of CpnE, a 6-oxohexanoate dehydrogenase (e.g., the gene product of ChnE from *Acinetobacter* sp.), or a 7-oxoheptanoate dehydrogenase (e.g., the gene product of ThnG from *Sphingomonas macrogolitabida*) (Iwaki et al., *Appl. Environ. Microbiol.*, 1999, 65(11), 5158-5162; Lopez-Sanchez et al., *Appl. Environ. Microbiol.*, 2010, 76(1), 110-118). For example, a 6-oxohexanoate dehydrogenase can be classified under EC 1.2.1.63 such as the gene product of ChnE. For example, a 7-oxoheptanoate dehydrogenase can be classified under EC 1.2.1.—.

In some embodiments, the second terminal carboxyl group leading to the synthesis of glutaric acid is enzymatically formed by a polypeptide having esterase activity such as an esterase classified under EC 3.1.1.—such as EC 3.1.1.1 or EC 3.1.1.6.

Figure 5:
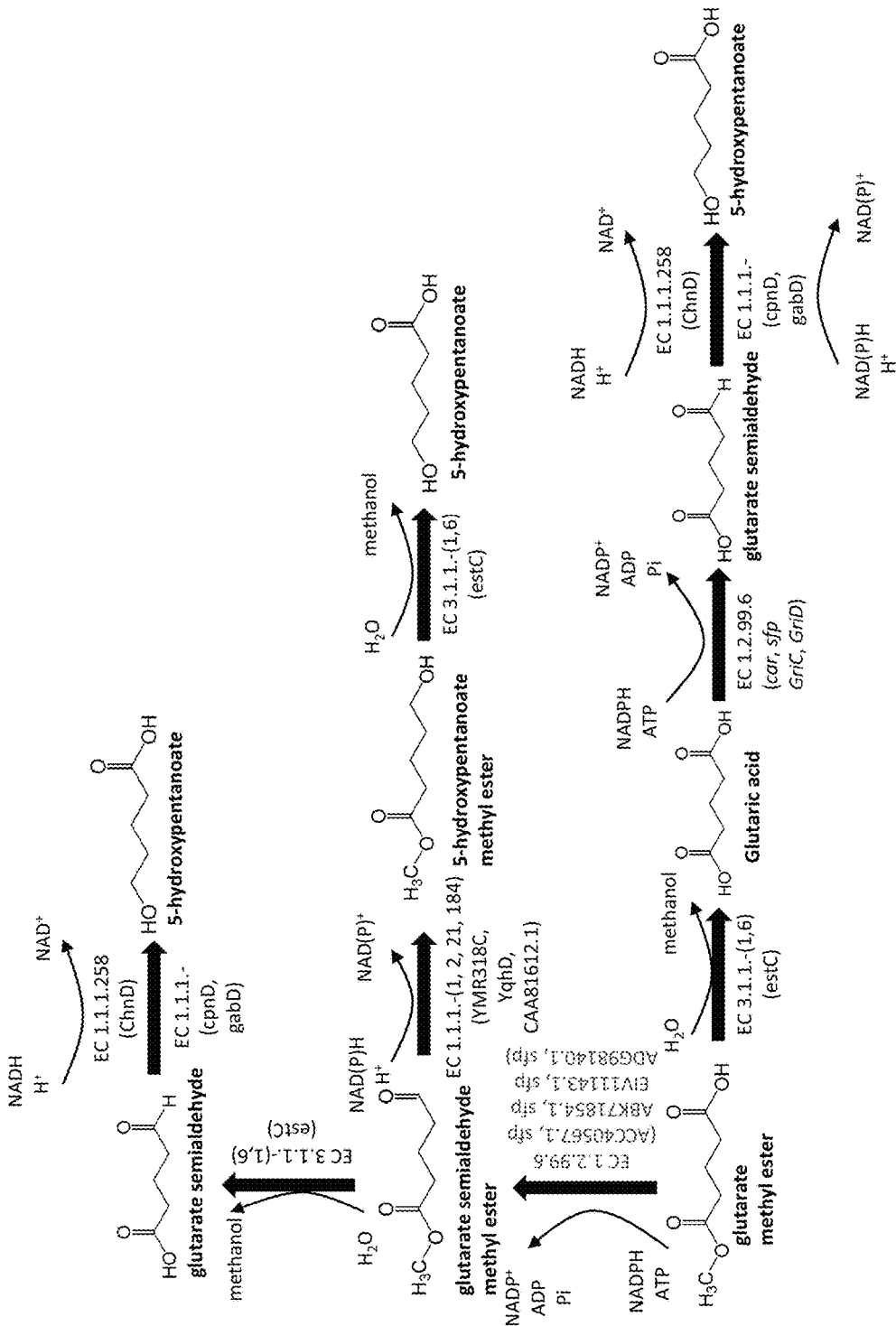
FIG. 5 is a schematic of an exemplary biochemical pathway leading to 5-hydroxypentanoate using glutarate methyl ester or glutarate as a central precursor.

Enzymes Generating the Terminal Hydroxyl Groups in the Biosynthesis of a 2,4-Pentadienoyl-CoA As depicted in FIG. 5, a terminal hydroxyl group can be enzymatically formed using an alcohol dehydrogenase such as a 6-hydroxyhexanoate dehydrogenase, a 5-hydroxypentanoate dehydrogenase, or a 4-hydroxybutyrate dehydrogenase.

For example, a terminal hydroxyl group leading to the synthesis of 5-hydroxypentanoate can be enzymatically formed by a dehydrogenase classified, for example, under EC 1.1.1.—such as a 6-hydroxyhexanoate dehydrogenase classified, for example, under EC 1.1.1.258 (e.g., the gene from ChnD), a 5-hydroxypentanoate dehydrogenase classified, for example, under EC 1.1.1.—such as the gene product of CpnD (see, for example, Iwaki et al., 2002, *Appl. Environ. Microbiol.*, 68(11):5671-5684), a 5-hydroxypentanoate dehydrogenase from *Clostridium viride*, or a 4-hydroxybutyrate dehydrogenase such as gabD (see, for example, Lütke-Eversloh & Steinbüchel, 1999, *FEMS Microbiology Letters*, 181(1):63-71). See, FIG. 5.

Figure 6:
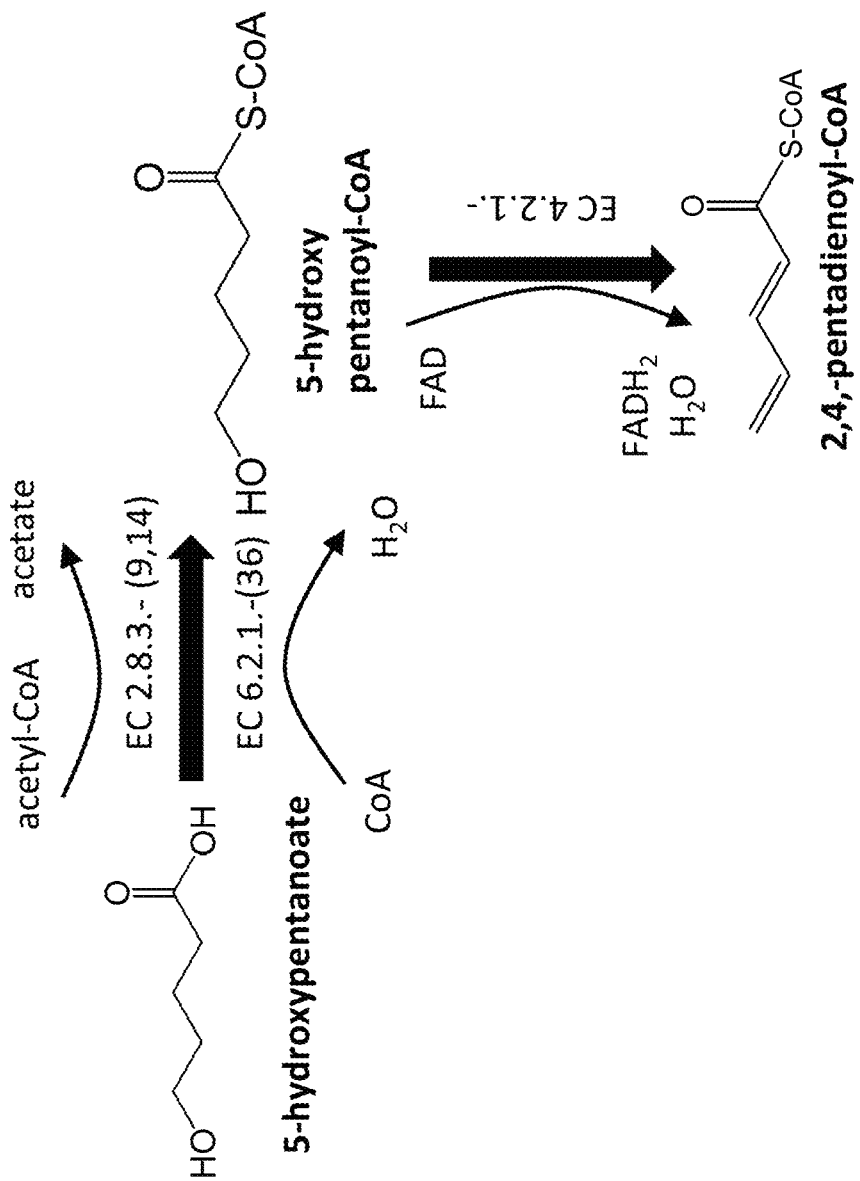
FIG. 6 is a schematic of an exemplary biochemical pathway leading to 2,4-pentadienoyl-CoA using 5-hydroxypentanoate as a central precursor.

Enzymes Generating the Terminal Vinyl Group in the Biosynthesis of a 2,4-Pentadienoyl-CoA As depicted in FIG. 6, a terminal vinyl group can be enzymatically formed using a dehydratase such as 5-hydroxypentanoyl-CoA dehydratase from *Clostridium viride* (Eikmanns and Buckel, 1991, Eur. J. Biochem., 197, 661-668).

Biochemical Pathways

Pathway to Glutarate Methyl Ester, Glutaryl-CoA or Glutaryl-[Acp] from Malonyl-[Acp] or Malonyl-CoA As shown in FIG. 1, glutarate methyl ester can be synthesized from malonyl-[acp] by conversion of malonyl-[acp] to malonyl-[acp] methyl ester by a malonyl-CoA O-methyltransferase classified, for example, under EC 2.1.1.197 such as the gene product of bioC; followed by conversion to 3-oxoglutaryl-[acp] methyl ester by condensation with malonyl-[acp] and a β-ketoacyl-[acp] synthase classified, for example, under EC 2.3.1.—such as EC 2.3.1.41, EC 2.3.1.179 or EC 2.3.1.180 (e.g., the gene product of fabB, fabF or fabH); followed by conversion to 3-hydroxy-glutaryl-[acp] methyl ester by a 3-hydroxyacyl-CoA dehydrogenase classified, for example, under EC 1.1.1.—such as EC 1.1.1.100 (e.g., the gene product of fabG); followed by conversion to 2,3-dehydroglutaryl-[acp] methyl ester by a 3-hydroxyacyl-[acp] dehydratase classified, for example, under EC 4.2.1.59 such as the gene product of fabZ; followed by conversion to glutaryl-[acp] methyl ester by a trans-2-enoyl-CoA reductase classified, for example, EC 1.3.1.—such as EC 1.3.1.10 such as the gene product of fabI; followed by (i) conversion to glutarate methyl ester by a thioesterase classified, for example, under EC 3.1.2.—such as the tesB (SEQ ID NO:15), YciA (SEQ ID NO:14) or Acot13, a *Bacteroides thetaiotaomicron* acyl-ACP thioesterase (GenBank Accession No. AAO77182) or a *Lactobacillus plantarum* acyl-CoA thioesterase (GenBank Accession No. CCC78182.1) or (ii) conversion to glutaryl-[acp] by a pimeloyl-[acp] methyl ester methylesterase classified, for example, under EC 3.1.1.85 such as bioH (SEQ ID NO: 1).

Figure 2:
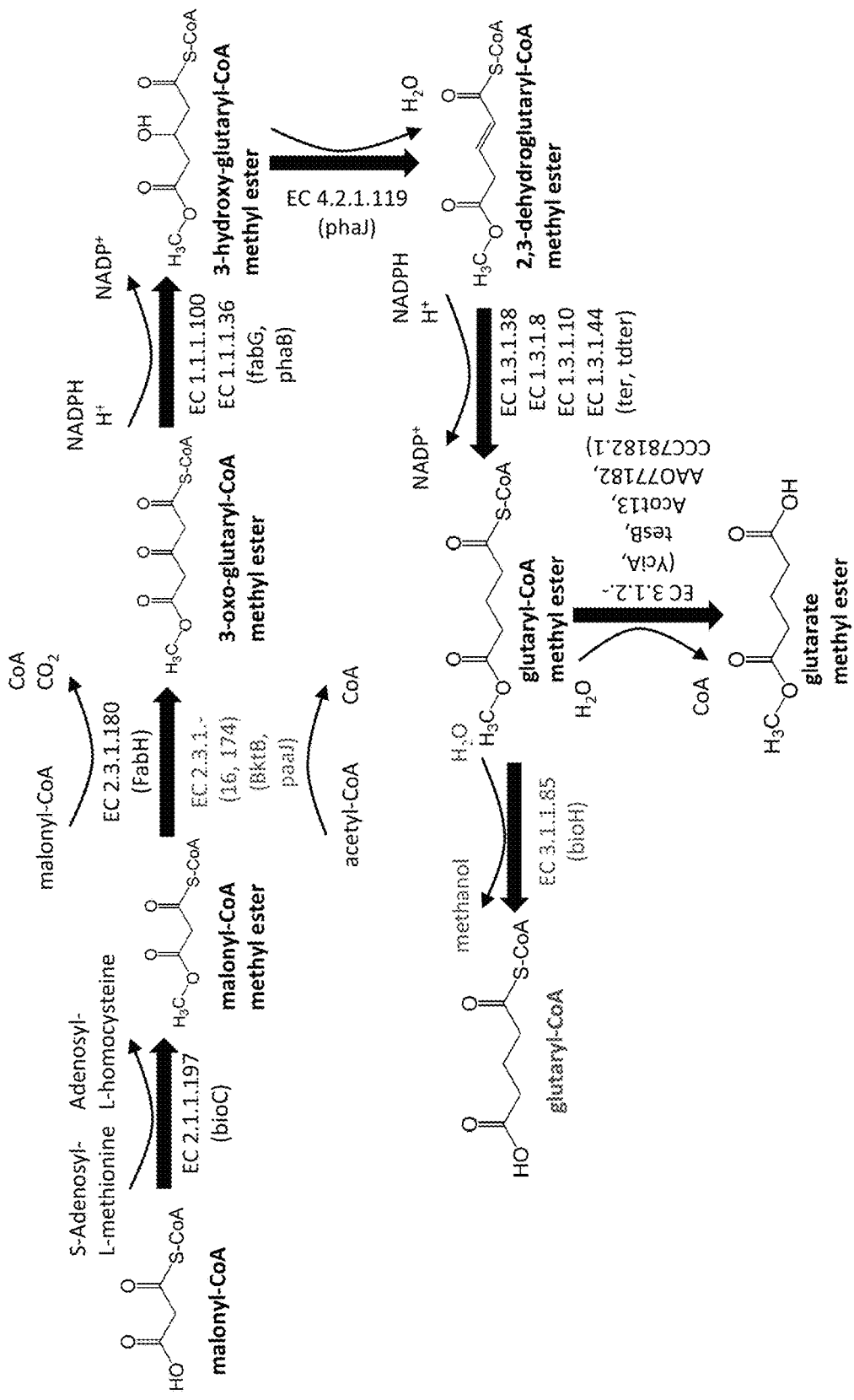
FIG. 2 is a schematic of exemplary biochemical pathways leading to glutarate methyl ester or glutaryl-CoA from malonyl-CoA using NADPH as reducing equivalent.

As shown in FIG. 2, glutarate methyl ester can be synthesized from malonyl-CoA by conversion of malonyl-CoA to malonyl-CoA methyl ester by a malonyl-CoA O-methyltransferase classified, for example, under EC 2.1.1.197 such as the gene product of bioC; followed by conversion to 3-oxoglutaryl-CoA methyl ester by condensation with acetyl-CoA by a β-ketothiolase classified, for example, under EC 2.3.1.16 such as the gene product of bktB or by condensation with malonyl-CoA by a β-ketoacyl-[acp] synthase classified, for example, under EC 2.3.1.180 such as the gene product of fabH; followed by conversion to 3-hydroxyglutaryl-CoA methyl ester by a 3-hydroxyacyl-CoA dehydrogenase classified, for example, under EC 1.1.1.—such as EC 1.1.1.100 (e.g., the gene product of fabG) or EC 1.1.1.36 (e.g., the gene product of phaB); followed by conversion to 2,3-dehydroglutaryl-CoA methyl ester by an enoyl-CoA hydratase classified, for example, under EC 4.2.1.119 such as the gene product of phaJ (Shen et al., *Appl. Environ. Microbiol.*, 2011, 77(9), 2905-2915; Fukui et al., Journal of Bacteriology, 1998, 180(3), 667-673); followed by conversion to glutaryl-CoA methyl ester by a trans-2-enoyl-CoA reductase classified, for example, EC 1.3.1.—such as EC 1.3.1.38, EC 1.3.1.8, EC 1.3.1.10 or EC 1.3.1.44; followed by (i) conversion to glutarate methyl ester by a thioesterase classified, for example, under EC 3.1.2.—such as the tesB (SEQ ID NO:15), YciA (SEQ ID NO:14) or Acot13, a *Bacteroides thetaiotaomicron* acyl-ACP thioesterase (GenBank Accession No. AAO77182) or a *Lactobacillus plantarum* acyl-ACP thioesterase (GenBank Accession No. CCC78182.1) or (ii) conversion to glutaryl-CoA by a pimeloyl-[acp] methyl ester methylesterase classified, for example, under EC 3.1.1.85 such as bioH (SEQ ID NO: 1).

Figure 3:
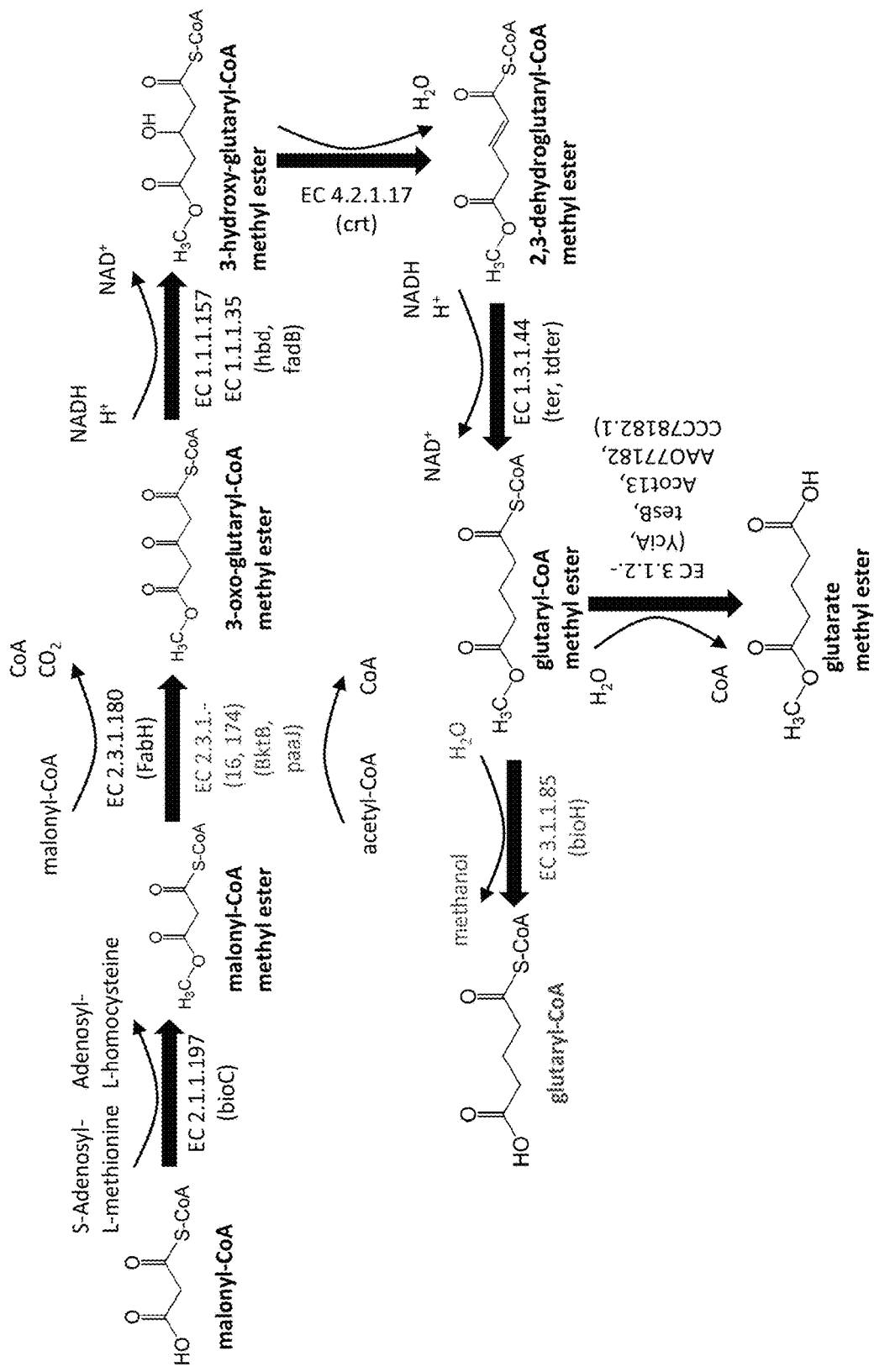
FIG. 3 is a schematic of exemplary biochemical pathways leading to glutarate methyl ester or glutaryl-CoA from malonyl-CoA using NADH as reducing equivalent.

As shown in FIG. 3, glutarate methyl ester can be synthesized from malonyl-CoA by conversion of malonyl-CoA to malonyl-CoA methyl ester by a malonyl-CoA O-methyltransferase classified, for example, under EC 2.1.1.197 such as the gene product of bioC; followed by conversion to 3-oxoglutaryl-CoA methyl ester by condensation with acetyl-CoA by a β-ketothiolase classified, for example, under EC 2.3.1.16 such as the gene product of bktB or by condensation with malonyl-CoA by a β-ketoacyl-[acp] synthase classified, for example, under EC 2.3.1.180 such as the gene product of fabH; followed by conversion to 3-hydroxyglutaryl-CoA methyl ester by a 3-hydroxyacyl-CoA dehydrogenase classified, for example, under EC 1.1.1.—such as EC 1.1.1.35 or EC 1.1.1.157 (e.g., the gene product of fadB or hbd); followed by conversion to 2,3-dehydroglutaryl-CoA methyl ester by an enoyl-CoA hydratase classified, for example, under EC 4.2.1.17 such as the gene product of crt; followed by conversion to glutaryl-CoA methyl ester by a trans-2-enoyl-CoA reductase classified, for example, under EC 1.3.1.44 such as the gene product of ter or tdter; followed by (i) conversion to glutarate methyl ester by a thioesterase classified, for example, under EC 3.1.2.—such as the tesB (SEQ ID NO:15), YciA (SEQ ID NO:14) or Acot13, a *Bacteroides thetaiotaomicron* acyl-ACP thioesterase (GenBank Accession No. AAO77182) or a *Lactobacillus plantarum* acyl-CoA thioesterase (GenBank Accession No. CCC78182.1) or (ii) conversion to glutaryl-CoA by a pimeloyl-[acp] methyl ester methylesterase classified, for example, under EC 3.1.1.85 such as bioH (SEQ ID NO: 1).

Pathway to Glutarate or 5-Oxopentanoate Using Glutarate Methyl Ester, Glutaryl-[Acp] or Glutaryl-CoA as a Central Precursor As depicted in FIG. 4, glutarate methyl ester can be converted to glutarate by an esterase classified, for example, EC 3.1.1.—, such as EC 3.1.1.1 or EC 3.1.1.6 such as estC (SEQ ID NO: 8).

As depicted in FIG. 4, glutaryl-CoA can be converted to glutarate by a (i) a thioesterase classified, for example, EC 3.1.2.—, such as the tesB (SEQ ID NO:15), YciA (SEQ ID NO:14) or Acot13, a *Bacteroides thetaiotaomicron* acyl-ACP thioesterase (GenBank Accession No. AAO77182) or a *Lactobacillus plantarum* acyl-CoA thioesterase (GenBank Accession No. CCC78182.1) (ii) a reversible CoA-ligase classified, for example, under EC 6.2.1.5, (iii) a CoA-transferase classified, for example, under EC 2.8.3.—such as EC 2.8.3.12, or (iv) an acylating dehydrogenase classified under, for example, EC 1.2.1.10 or EC 1.2.1.76 such as encoded by PduB or PduP and an aldehyde dehydrogenase classified under EC 1.2.1.—such as a glutarate semialdehyde dehydrogenase classified, for example, under EC 1.2.1.20, a succinate-semialdehyde dehydrogenase classified, for example, under EC 1.2.1.16 or EC 1.2.1.79, or an aldehyde dehydrogenase classified under EC 1.2.1.3. For example, a 5-oxovalerate dehydrogenase such as the gene product of CpnE, a 6-oxohexanoate dehydrogenase such as the gene product of ChnE, or a 7-oxoheptanoate dehydrogenase (e.g., the gene product of ThnG from *Sphingomonas macrogolitabida*) can be used to convert 5-oxopentanoic acid to glutarate.

As depicted in FIG. 4, glutaryl-[acp] can be converted to glutarate by a thioesterase classified, for example, EC 3.1.2.—, such as the tesB (SEQ ID NO:15), YciA (SEQ ID NO:14) or Acot13, a *Bacteroides thetaiotaomicron* acyl-ACP thioesterase (GenBank Accession No. AAO77182) or a *Lactobacillus plantarum* acyl-CoA thioesterase (GenBank Accession No. CCC78182.1).

Pathway to 5-Hydroxypentanoate Using Glutarate Methyl Ester as a Central Precursor As depicted in FIG. 5, 5-hydroxypentanoate can be synthesized from the central precursor glutarate methyl ester by conversion of glutarate methyl ester to glutaric acid by an esterase classified under EC 3.1.1.—(e.g., the gene product of estC) such as a carboxyl esterase classified under EC 3.1.1.1 or an acetylesterase classified under EC 3.1.1.6; followed by conversion of glutaric acid to glutarate semialdehyde by a carboxylate reductase classified, for example, under EC 1.2.99.6 such as the gene product of car in combination with a phosphopantetheine transferase enhancer (e.g., encoded by a sfp (Genbank Accession No. CAA44858.1, SEQ ID NO:16) gene from *Bacillus subtilis* or npt (Genbank Accession No. ABI83656.1, SEQ ID NO:17) gene from *Nocardia*), or the gene product of GriC & GriD (Suzuki et al., *J. Antibiot.*, 2007, 60(6), 380-387); followed by conversion to 5-hydroxypentanoate by a dehydrogenase classified, for example, under EC 1.1.1.—such as a 6-hydroxyhexanoate dehydrogenase classified, for example, under EC 1.1.1.258 (e.g., the gene from of ChnD), a 5-hydroxypentanoate dehydrogenase classified, for example, under EC 1.1.1.—such as the gene product of CpnD (see, for example, Iwaki et al., 2002, *Appl. Environ. Microbiol.*, 68(11):5671-5684), or a 4-hydroxybutyrate dehydrogenase such as gabD (see, for example, Lütke-Eversloh & Steinbüchel, 1999, *FEMS Microbiology Letters*, 181(1):63-71). See, FIG. 5.

As depicted in FIG. 5, 5-hydroxypentanoate can be synthesized from the central precursor glutarate methyl ester by conversion of glutarate methyl ester to glutarate semialdehyde methyl ester by a carboxylate reductase classified, for example, under EC 1.2.99.6 such as from a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Mycobacterium massiliense* (see Genbank Accession No. EIV11143.1, SEQ ID NO: 6), or a *Segniliparus rotundus* (see Genbank Accession No. ADG98140.1, SEQ ID NO: 7), in combination with a phosphopantetheine transferase enhancer (e.g., encoded by a sfp (Genbank Accession No. CAA44858.1, SEQ ID NO:16) gene from *Bacillus subtilis* or npt (Genbank Accession No. ABI83656.1, SEQ ID NO:17) gene from *Nocardia*), or the gene product of GriC & GriD (Suzuki et al., *J. Antibiot.*, 2007, 60(6), 380-387); followed by conversion to glutarate semialdehyde by an esterase classified under EC 3.1.1.—(e.g., the gene product of estC) such as a carboxyl esterase classified under EC 3.1.1.1 or an acetylesterase classified under EC 3.1.1.6; followed by conversion to 5-hydroxypentanoate by a dehydrogenase classified, for example, under EC 1.1.1.—such as a 6-hydroxyhexanoate dehydrogenase classified, for example, under EC 1.1.1.258 (e.g., the gene from of ChnD), a 5-hydroxypentanoate dehydrogenase classified, for example, under EC 1.1.1.—such as the gene product of CpnD, or a 4-hydroxybutyrate dehydrogenase such as gabD.

As depicted in FIG. 5, 5-hydroxypentanoate can be synthesized from the central precursor glutarate methyl ester by conversion of glutarate methyl ester to glutarate semialdehyde methyl ester by a carboxylate reductase classified, for example, under EC 1.2.99.6 such as from a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Mycobacterium massiliense* (see Genbank Accession No. EIV11143.1, SEQ ID NO: 6), or a *Segniliparus rotundus* (see Genbank Accession No. ADG98140.1, SEQ ID NO: 7), in combination with a phosphopantetheine transferase enhancer (e.g., encoded by a sfp (Genbank Accession No. CAA44858.1, SEQ ID NO:16) gene from *Bacillus subtilis* or npt (Genbank Accession No. ABI83656.1, SEQ ID NO:17) gene from *Nocardia*), or the gene product of GriC & GriD (Suzuki et al., *J. Antibiot.*, 2007, 60(6), 380-387); followed by conversion to 5-hydroxypentanoate methyl ester by an alcohol dehydrogenase classified, for example, under EC 1.1.1.—(e.g., EC 1.1.1.1, EC 1.1.1.2, EC 1.1.1.21, or EC 1.1.1.184) such as the gene product of YMR318C, YqhD, or the protein having GenBank Accession No. CAA81612.1; followed by conversion to 5-hydroxypentanoate by an esterase classified under EC 3.1.1.—(e.g., the gene product of estC) such as a carboxyl esterase classified under EC 3.1.1.1 or an acetylesterase classified under EC 3.1.1.6.

Pathway to 2,4-Pentadienoyl-CoA Using 5-Hydroxypentanoate as a Central Precursor As depicted in FIG. 6, 2,4-pentadienoyl-CoA can be synthesized from 5-hydroxypentanoate by conversion of 5-hydroxypentanoate to 5-hydroxypentanoyl-CoA by a 5-hydroxypentanoate CoA-transferase or 4-hydroxybutryrate CoA-transferase classified, for example, under EC 2.8.3.—such as EC 2.8.3.14 or EC 2.8.3.9 or by a synthase classified, for example, under EC 6.2.1.—such as a 3-hydroxypropionyl-CoA synthase classified under EC 6.2.1.36; followed by conversion to 2,4-pentadienoyl-CoA by a dehydratase such as 5-hydroxypentanoy-CoA dehydratase classified, for example, under EC 4.2.1.—obtained from *Clostridium viride*.

Cultivation Strategy

In some embodiments, the cultivation strategy entails achieving an aerobic, anaerobic, micro-aerobic, or mixed oxygen/denitrification cultivation condition. Enzymes characterized in vitro as being oxygen sensitive require a micro-aerobic cultivation strategy maintaining a very low dissolved oxygen concentration (See, for example, Chayabatra & Lu-Kwang, *Appl. Environ. Microbiol.*, 2000, 66(2), 493 0 498; Wilson and Bouwer, 1997, *Journal of Industrial Microbiology and Biotechnology*, 18(2-3), 116-130).

In some embodiments, a cyclical cultivation strategy entails alternating between achieving an anaerobic cultivation condition and achieving an aerobic cultivation condition.

In some embodiments, the cultivation strategy entails nutrient limitation such as nitrogen, phosphate or oxygen limitation.

In some embodiments, a final electron acceptor other than oxygen such as nitrates can be utilized. In some embodiments, a cell retention strategy using, for example, ceramic membranes can be employed to achieve and maintain a high cell density during either fed-batch or continuous fermentation.

In some embodiments, the principal carbon source fed to the fermentation in the synthesis of one or more C5 building blocks can derive from biological or non-biological feedstocks.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli*, *Cupriavidus necator*, *Pseudomonas oleavorans*, *Pseudomonas putida* and *Yarrowia lipolytica* (Lee et al., *Appl. Biochem. Biotechnol.*, 2012, 166:1801-1813; Yang et al., *Biotechnology for Biofuels*, 2012, 5:13; Meijnen et al., *Appl. Microbiol. Biotechnol.*, 2011, 90:885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, 2011, supra; Martin and Prather, *J. Biotechnol.*, 2009, 139:61-67).

The efficient catabolism of lignin-derived aromatic compounds such as benzoate analogues has been demonstrated in several microorganisms such as *Pseudomonas putida*, *Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7):2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli*, *Corynebacterium glutamicum* and *Lactobacillus delbrueckii* and *Lactococcus lactis* (see, e.g., Hermann et al, *J. Biotechnol.*, 2003, 104: 155-172; Wee et al., *Food Technol. Biotechnol.*, 2006, 44(2):163-172; Ohashi et al., *J. Bioscience and Bioengineering*, 1999, 87(5):647-654).

The efficient utilization of furfural, derived from a variety of agricultural lignocellulosic sources, has been demonstrated for *Cupriavidus necator* (Li et al., *Biodegradation*, 2011, 22:1215-1225).

In some embodiments, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Köpke et al., *Applied and Environmental Microbiology*, 2011, 77(15): 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1):152-156).

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12 or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a 2,4-pentadienoyl-CoA.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data can be utilized to inform or support genome-scale system biology techniques, thereby devising genome scale attenuation or knockout strategies in directing carbon flux to 2,4-pentadienoyl-CoA.

In some embodiments, the host microorganism's tolerance to high concentrations of 2,4-pentadienoyl-CoA can be improved through continuous cultivation in a selective environment.

In some embodiments, the host microorganism's endogenous biochemical network can be attenuated or augmented to (1) ensure the intracellular availability of acetyl-CoA, (2) create a NADH or NADPH imbalance that may be balanced via the formation of 2,4-pentadienoyl-CoA, and/or (3) prevent degradation of central metabolites, central precursors leading to and including 2,4-pentadienoyl-CoA.

In some embodiments requiring intracellular availability of acetyl-CoA-CoA for C5 building block synthesis, endogenous enzymes catalyzing the hydrolysis of acetyl-CoA such as short-chain length thioesterases can be attenuated in the host organism.

In some embodiments requiring condensation of acetyl-CoA and malonyl-CoA for 2,4-pentadienoyl-CoA synthesis, one or more endogenous β-ketothiolases catalyzing the condensation of only acetyl-CoA to acetoacetyl-CoA such as the endogenous gene products of AtoB or phaA can be attenuated.

In some embodiments requiring the intracellular availability of acetyl-CoA for 2,4-pentadienoyl-CoA synthesis, an endogenous phosphotransacetylase generating acetate such as pta can be attenuated (Shen et al., *Appl. Environ. Microbiol.*, 2011, 77(9):2905-2915).

In some embodiments requiring the intracellular availability of acetyl-CoA for 2,4-pentadienoyl-CoA synthesis, an endogenous gene in an acetate synthesis pathway encoding an acetate kinase, such as ack, can be attenuated.

In some embodiments requiring the intracellular availability of acetyl-CoA and NADH for 2,4-pentadienoyl-CoA synthesis, an endogenous gene encoding an enzyme that catalyzes the degradation of pyruvate to lactate such as a lactate dehydrogenase encoded by ldhA can be attenuated (Shen et al., 2011, supra).

In some embodiments requiring the intracellular availability of acetyl-CoA and NADH for 2,4-pentadienoyl-CoA synthesis, endogenous genes encoding enzymes, such as menaquinol-fumarate oxidoreductase, that catalyze the degradation of phophoenolpyruvate to succinate such as frdBC can be attenuated (see, e.g., Shen et al., 2011, supra).

In some embodiments requiring the intracellular availability of acetyl-CoA and NADH for 2,4-pentadienoyl-CoA synthesis, an endogenous gene encoding an enzyme that catalyzes the degradation of acetyl-CoA to ethanol such as the alcohol dehydrogenase encoded by adhE can be attenuated (Shen et al., 2011, supra).

In some embodiments, where pathways require excess NADH co-factor for 2,4-pentadienoyl-CoA synthesis, a recombinant formate dehydrogenase gene can be overexpressed in the host organism (Shen et al., 2011, supra).

In some embodiments, acetyl-CoA carboxylase can be overexpressed in the host organisms.

In some embodiments, one or more of 3-phosphoglycerate dehydrogenase, 3-phosphoserine aminotransferase and phosphoserine phosphatase can be overexpressed in the host to generate serine as a methyl donor for the S-Adenosyl-L-methionine cycle.

In some embodiments, a methanol dehydrogenase or a formaldehyde dehydrogenase can be overexpressed in the host to allow methanol catabolism via formate.

In some embodiments, where pathways require excess NADH or NADPH co-factor for 2,4-pentadienoyl-CoA synthesis, a transhydrogenase dissipating the cofactor imbalance can be attenuated.

In some embodiments, an endogenous gene encoding an enzyme that catalyzes the degradation of pyruvate to ethanol such as pyruvate decarboxylase can be attenuated.

In some embodiments, an endogenous gene encoding an enzyme that catalyzes the generation of isobutanol such as a 2-oxoacid decarboxylase can be attenuated.

In some embodiments requiring the intracellular availability of acetyl-CoA for 2,4-pentadienoyl-CoA synthesis, a recombinant acetyl-CoA synthetase such as the gene product of acs can be overexpressed in the microorganism (Satoh et al., *J. Bioscience and Bioengineering*, 2003, 95(4):335-341).

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, Biotechnology Progress, 19(5), 1444-1449).

In some embodiments, where pathways require excess NADPH co-factor in the synthesis of 2,4-pentadienoyl-CoA, a gene such as UdhA encoding a puridine nucleotide transhydrogenase can be overexpressed in the host organisms (Brigham et al., *Advanced Biofuels and Bioproducts*, 2012, Chapter 39, 1065-1090).

In some embodiments, where pathways require excess NADPH co-factor in the synthesis of 2,4-pentadienoyl-CoA, a recombinant glyceraldehyde-3-phosphate-dehydrogenase gene such as GapN can be overexpressed in the host organisms (Brigham et al., 2012, supra).

In some embodiments, where pathways require excess NADPH co-factor in the synthesis of 2,4-pentadienoyl-CoA, a recombinant malic enzyme gene such as maeA or maeB can be overexpressed in the host organisms (Brigham et al., 2012, supra).

In some embodiments, where pathways require excess NADPH co-factor in the synthesis of 2,4-pentadienoyl-CoA, a recombinant glucose-6-phosphate dehydrogenase gene such as zwf can be overexpressed in the host organisms (Lim et al., *J. Bioscience and Bioengineering*, 2002, 93(6), 543-549).

In some embodiments, where pathways require excess NADPH co-factor in the synthesis of 2,4-pentadienoyl-CoA, a recombinant fructose 1,6 diphosphatase gene such as fbp can be overexpressed in the host organisms (Becker et al., *J. Biotechnol.*, 2007, 132:99-109).

In some embodiments, where pathways require excess NADPH co-factor in the synthesis of a C5 building block, endogenous triose phosphate isomerase (EC 5.3.1.1) can be attenuated.

In some embodiments, where pathways require excess NADPH co-factor in the synthesis of 2,4-pentadienoyl-CoA, a recombinant glucose dehydrogenase such as the gene product of gdh can be overexpressed in the host organism (Satoh et al., *J. Bioscience and Bioengineering*, 2003, 95(4): 335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific).

In some embodiments, an endogenous glutamate dehydrogenase (EC 1.4.1.3) that utilizes both NADH and NADPH as co-factors can be attenuated.

In some embodiments, a membrane-bound enoyl-CoA reductase can be solubilized via expression as a fusion protein to a small soluble protein such as a maltose binding protein (Gloerich et al., FEBS Letters, 2006, 580, 2092-2096).

In some embodiments using hosts that naturally accumulate polyhydroxyalkanoates, the endogenous polyhydroxyalkanoate synthase enzymes can be attenuated in the host strain.

In some embodiments using hosts that naturally accumulate lipid bodies, the genes encoding enzymes involved with lipid body synthesis are attenuated.

In some embodiments, a L-glutamate dehydrogenase, a L-glutamine synthetase, or a glutamate synthase can be overexpressed in the host to regenerate L-glutamate from 2-oxoglutarate as an amino donor for w-transaminase reactions.

In some embodiments, enzymes such as pimeloyl-CoA dehydrogenase classified under, EC 1.3.1.62; an acyl-CoA dehydrogenase classified, for example, under EC 1.3.8.7 or EC 1.3.8.1; and/or a glutaryl-CoA dehydrogenase classified, for example, under EC 1.3.8.6 that degrade central metabolites and central precursors leading to and including C5 building blocks can be attenuated.

In some embodiments, endogenous enzymes activating C5 building blocks via Coenzyme A esterification such as CoA-ligases (e.g., a glutaryl-CoA synthetase) classified under, for example, EC 6.2.1.6 can be attenuated.

Producing 2,4-Pentadienoyl-CoA Using a Recombinant Host

Typically, 2,4-pentadienoyl-CoA can be produced by providing a host microorganism and culturing the provided microorganism with a culture medium containing a suitable carbon source as described above. In general, the culture media and/or culture conditions can be such that the microorganisms grow to an adequate density and produce 2,4-pentadienoyl-CoA efficiently. For large-scale production processes, any method can be used such as those described elsewhere (Manual of Industrial Microbiology and Biotechnology, 2$^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Figure 7:
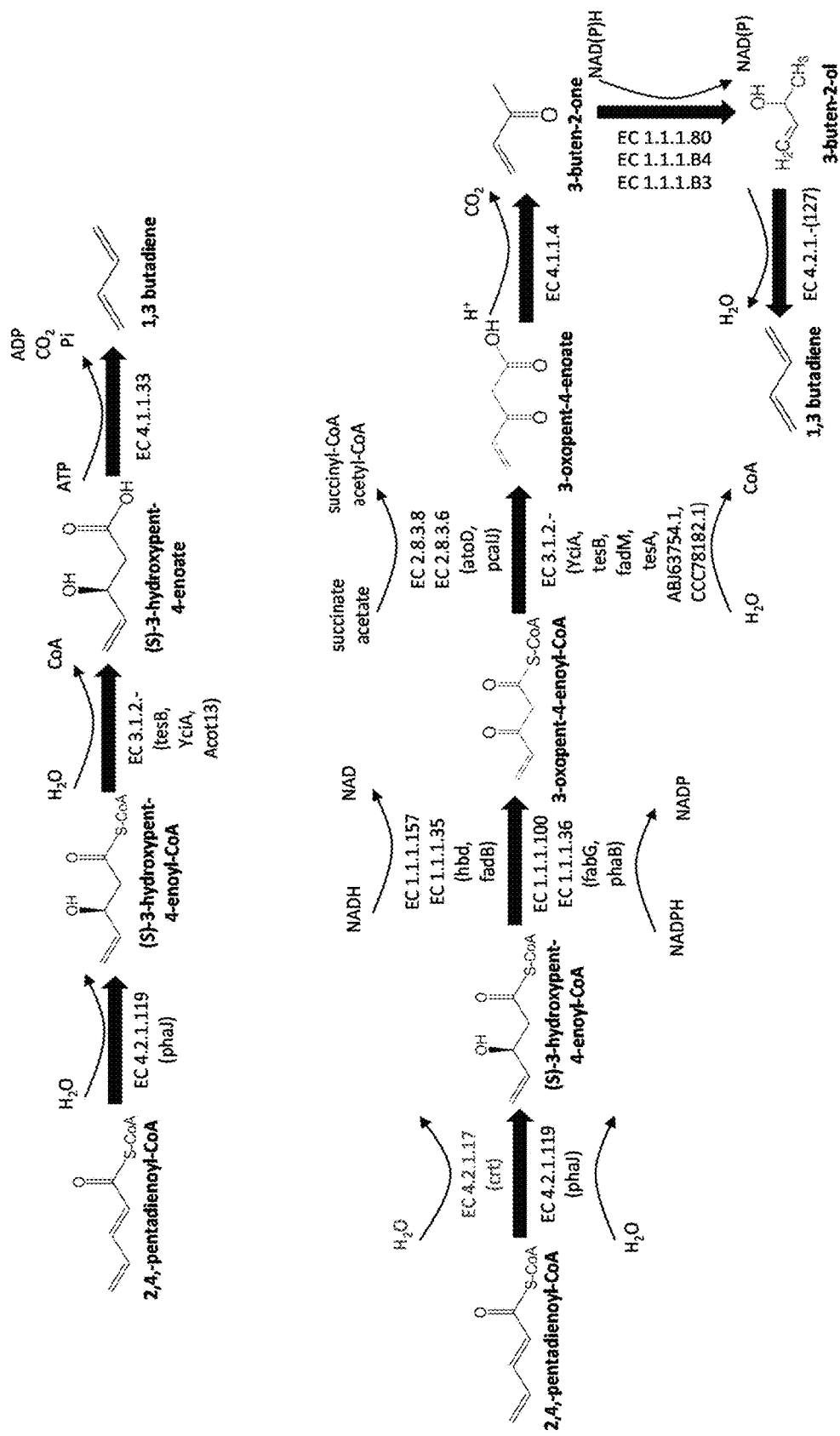
FIG. 7 is a schematic of an exemplary biochemical pathway leading to 1,3-butadiene using 2,4-pentadienoyl-CoA as central precursor.

Once transferred, the microorganisms can be incubated to allow for the production of 2,4-pentadienoyl-CoA. Once produced, any method can be used to produce 1,3-butadiene from 2,4-pentadienoyl-CoA such as depicted in FIG. 7. The invention is further described in the following examples, which do not limit the scope of the invention described in the claims.

EXAMPLES

Example 1

Enzyme Activity of Carboxylate Reductase Using Glutarate Methyl Ester as Substrate and Forming Glutarate Semialdehyde Methyl Ester A nucleotide sequence encoding a His-tag was added to the genes from *Mycobacterium marinum*, *Mycobacterium smegmatis*, *Segniliparus rugosus*, *Mycobacterium massiliense*, and *Segniliparus rotundus* that encode the carboxylate reductases of SEQ ID NOs: 2-4, 6 and 7, respectively (GenBank Accession Nos. ACC40567.1, ABK71854.1, EFV11917.1, EIV11143.1, and ADG98140.1, respectively) (see FIG. 8) such that N-terminal HIS tagged carboxylate reductases could be produced. Each of the modified genes was cloned into a pET Duet expression vector alongside a sfp gene encoding a His-tagged phosphopantetheine transferase from *Bacillus subtilis*, both under control of the T7 promoter. Each expression vector was transformed into a BL21[DE3] *E. coli* host along with the expression vectors from Example 2. Each resulting recombinant *E. coli* strain was cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5) and concentrated via ultrafiltration.

Figure 9:
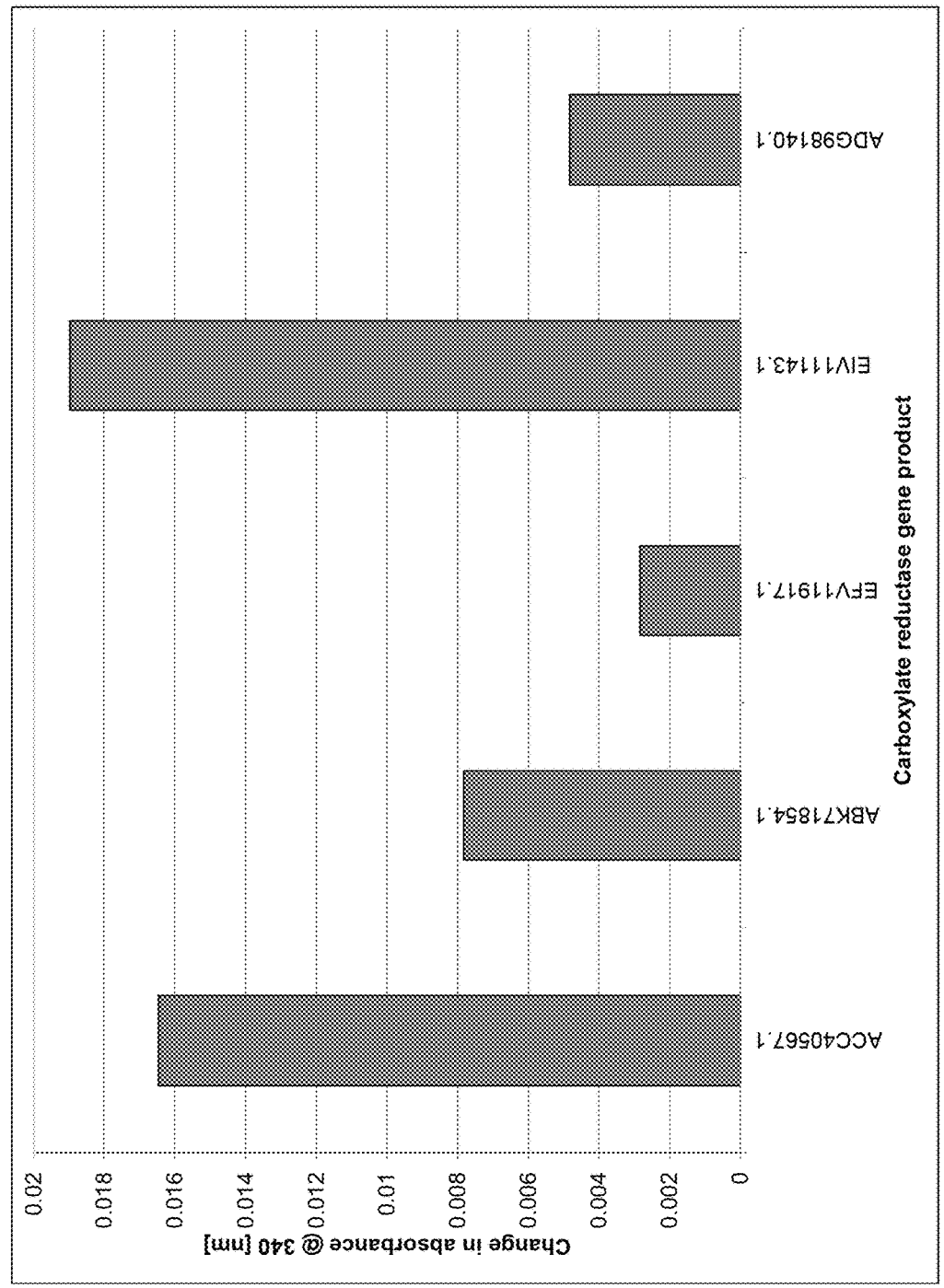
FIG. 9 is a bar graph summarizing the change in absorbance at 340 nm after 20 minutes, which is a measure of the consumption of NADPH and activity of five carboxylate reductase preparations in enzyme only controls (no substrate).

The enzyme activity assay was performed in triplicate in a buffer composed of a final concentration of 50 mM HEPES buffer (pH=7.5), 2 mM glutarate methyl ester, 10 mM $MgCl_2$, 1 mM ATP and 1 mM NADPH. The enzyme activity assay reaction was initiated by adding purified carboxylate reductase and phosphopantetheine transferase or the empty vector control to the assay buffer containing the glutarate methyl ester and then incubated at room temperature for 20 min. The consumption of NADPH was monitored by absorbance at 340 nm. The enzyme only control without glutarate methyl ester demonstrated low base line consumption of NADPH. See FIG. 9.

Figure 10:
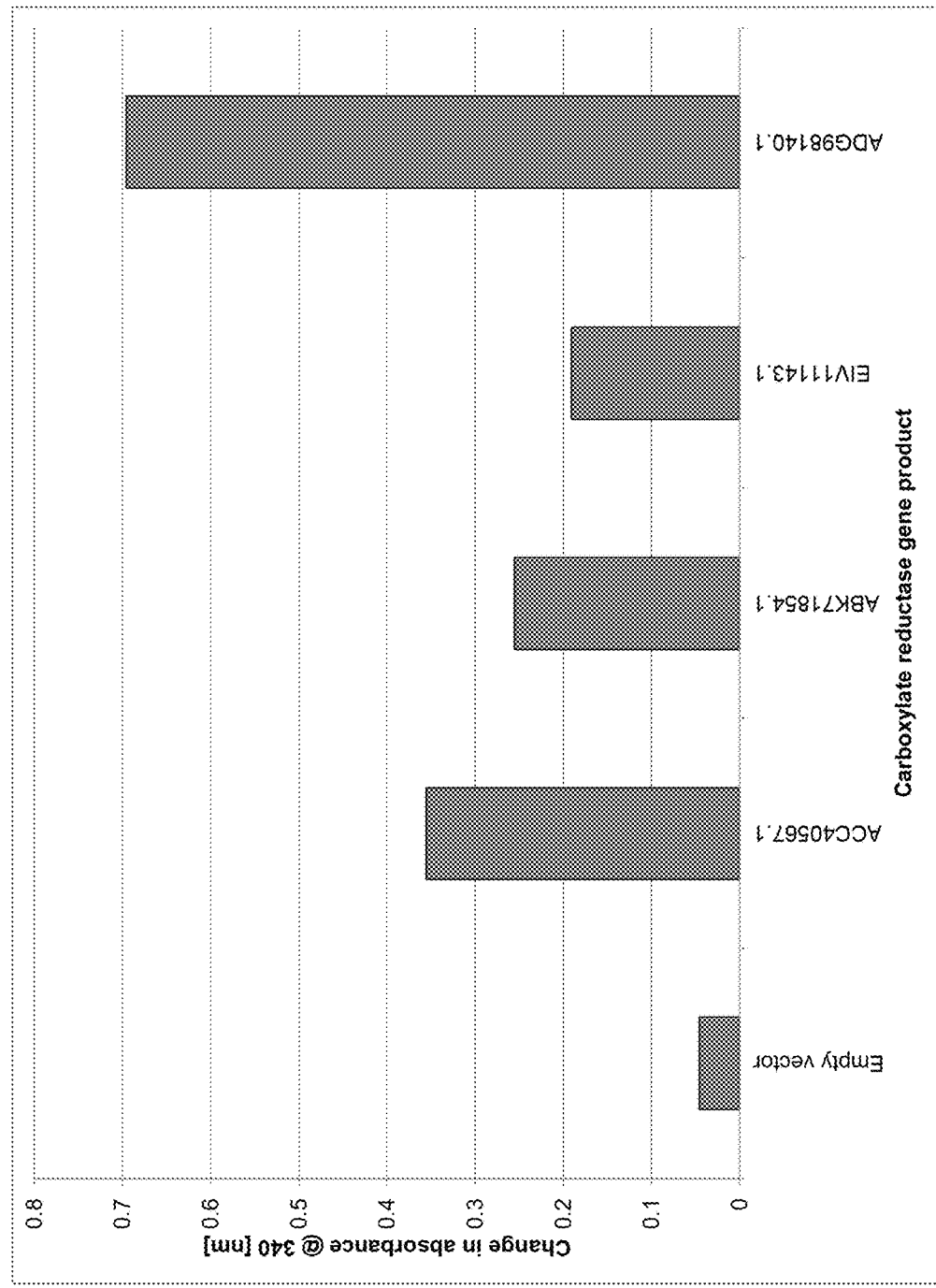
FIG. 10 is a bar graph of the change in absorbance at 340 nm after 20 minutes, which is a measure of the consumption of NADPH and activity of a carboxylate reductase preparation for converting glutarate methyl ester to glutarate semialdehyde methyl ester relative to the empty vector control.

The gene product of SEQ ID NO 2, 3, 6, and 7, enhanced by the gene product of sfp, accepted glutarate methyl ester as substrate as confirmed against the empty vector control (see FIG. 10) and synthesized glutarate semialdehyde methyl ester.

Example 2

Enzyme Activity of Pimeloyl-[Acp] Methyl Ester Methylesterase Using Glutaryl-CoA Methyl Ester as Substrate and Forming Glutaryl-CoA A sequence encoding an C-terminal His-tag was added to the gene from *Escherichia coli* encoding the pimeloyl-[acp] methyl ester methylesterase of SEQ ID NO: 1 (see FIG. 8) such that C-terminal HIS tagged pimeloyl-[acp] methyl ester methylesterase could be produced. The resulting modified gene was cloned into a pET28b+ expression vector under control of the T7 promoter and the expression vector was transformed into a BL21[DE3] *E. coli* host. The resulting recombinant *E. coli* strain was cultivated at 37° C. in a 500 mL shake flask culture containing 100 mL LB media and antibiotic selection pressure, with shaking at 230 rpm. Each culture was induced overnight at 18° C. using 0.3 mM IPTG.

The pellet from each induced shake flask culture was harvested via centrifugation. Each pellet was resuspended and lysed via sonication. The cell debris was separated from the supernatant via centrifugation. The pimeloyl-[acp] methyl ester methylesterase was purified from the supernatant using Ni-affinity chromatography, buffer exchanged and concentrated into 20 mM HEPES buffer (pH=7.5) via ultrafiltration and stored at 4° C.

Enzyme activity assays converting glutaryl-CoA methyl ester to glutaryl-CoA were performed in triplicate in a buffer composed of a final concentration of 25 mM Tris.HCl buffer (pH=7.0) and 5 [mM] glutaryl-CoA methyl ester. The enzyme activity assay reaction was initiated by adding pimeloyl-[acp] methyl ester methylesterase to a final concentration of 10 [µM] to the assay buffer containing the glutaryl-CoA methyl ester and incubated at 30° C. for 1 h, with shaking at 250 rpm. The formation of glutaryl-CoA was quantified via LC-MS.

The substrate only control without enzyme showed no trace quantities of the substrate glutaryl-CoA. See FIG. 11. The pimeloyl-[acp] methyl ester methylesterase of SEQ ID NO. 1 accepted glutaryl-CoA methyl ester as substrate and synthesized glutaryl-CoA as reaction product as confirmed via LC-MS. See FIG. 11.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of biosynthesizing glutarate methyl ester in a recombinant host comprising at least one exogenous nucleic acid encoding a polypeptide having malonyl-CoA O-methyltransferase activity, the method comprising enzymatically converting at least one of malonyl-[acp] and malonyl-CoA to glutarate methyl ester in said host using a polypeptide having malonyl-CoA O-methyltransferase activity, a polypeptide having thioesterase activity, or a combination thereof, wherein said polypeptide having malonyl-CoA O-methyltransferase activity has at least 90% sequence identity to the amino acid sequence set forth in SEQ ID NO:13 and is capable of enzymatically converting malonyl-CoA to malonyl-CoA methyl ester or malonyl-[acp] to malonyl-[acp] methyl ester, and wherein said polypeptide having thioesterase activity has at least 90% sequence identity to the amino acid sequence set forth in SEQ ID NO:9, SEQ ID NO:10, SEQ ID NO:14, or SEQ ID NO:15 and is capable of enzymatically converting glutaryl-CoA methyl ester to glutarate methyl ester,
   wherein malonyl-CoA is enzymatically converted to malonyl-CoA methyl ester using said at least one polypeptide having malonyl-CoA O-methyltransferase activity; or
   wherein malonyl-[acp] is enzymatically converted to malonyl-[acp] methyl ester using said at least one polypeptide having malonyl-CoA O-methyltransferase activity,
   the method optionally further comprising enzymatically converting glutarate methyl ester to glutarate semialdehyde methyl ester in said host using at least one polypeptide having carboxylate reductase activity, wherein said polypeptide having carboxylate reductase activity has at least 90% sequence identity to the amino acid sequence set forth in SEQ ID NO: 2, SEQ ID NO:3, SEQ ID NO:4, SEQ ID NO:5, SEQ ID NO:6 or SEQ ID NO:7 and is capable of enzymatically converting glutarate methyl ester to glutarate semialdehyde methyl ester,
   wherein said enzymatic conversion occurs in the host using said polypeptide having malonyl-CoA O-methyltransferase activity, said polypeptide having thioesterase activity, or a combination thereof.

2. The method of claim 1, wherein malonyl-[acp] methyl ester is enzymatically converted to glutaryl-[acp] methyl ester using at least one polypeptide having an activity selected from the group consisting of synthase activity, dehydrogenase activity, dehydratase activity, and reductase activity, wherein said polypeptide having reductase activity has at least 90% sequence identity to the amino acid sequence set forth in SEQ ID NO: 11 or 12 and is capable of enzymatically converting malonyl-[acp] methyl ester to glutaryl-[acp] methyl ester, and wherein glutaryl-[acp] methyl ester is enzymatically converted to glutarate methyl ester using at least one polypeptide having thioesterase activity, wherein said polypeptide having thioesterase activity has at least 90% sequence identity to the amino acid sequence set forth in SEQ ID NO: 9, SEQ ID NO:10, SEQ ID NO:14, or SEQ ID NO:15 and is capable of enzymatically converting glutaryl-CoA methyl ester to glutarate methyl ester.

3. The method of claim 1, further comprising enzymatically converting glutarate methyl ester to 5-oxopentanoic acid using at least one polypeptide having an activity selected from the group consisting of carboxylate reductase activity and esterase activity, the method optionally further comprising enzymatically converting glutarate semialdehyde methyl ester to 5-hydroxypentanoic acid using at least one polypeptide having esterase activity, wherein the polypeptide having esterase activity has at least 90% sequence identity to the amino acid sequence set forth in SEQ ID NO:8 and is capable of enzymatically converting glutarate semialdehyde methyl ester to 5-hydroxypentanoic acid,
   the method optionally further comprising using at least one polypeptide having dehydrogenase activity classified in EC 1.1.1- to enzymatically convert glutarate semialdehyde methyl ester to 5-hydroxypentanoic acid.

4. The method of claim 1, said method further comprising enzymatically converting glutarate methyl ester to glutaric acid using at least one polypeptide having esterase activity, wherein the polypeptide having esterase activity has at least 90% sequence identity to the amino acid sequence set forth in SEQ ID NO:8, the method optionally further comprising enzymatically converting glutaric acid to 5-hydroxypentanoic acid using at least one polypeptide having carboxylate reductase activity and at least one polypeptide having dehydrogenase activity classified under EC 1.1.1.-, wherein the polypeptide having carboxylate reductase activity has at least 90% sequence identity to any one of the amino acid sequences set forth in any one of SEQ ID NOs: 2-7 and is capable of enzymatically converting glutarate methyl ester to glutaric acid.

5. The method of claim 4, further comprising enzymatically converting 5-hydroxypentanoic acid to 2,4-pentadienoyl-CoA using at least one polypeptide having an activity selected from the group consisting of CoA-transferase activity, a synthase activity, and dehydratase activity.

6. The method of claim 5, wherein (i) the polypeptide having a CoA-transferase activity or a synthase activity and (ii) the polypeptide having dehydratase activity enzymatically convert 5-hydroxypentoic acid to 2,4-pentadienoyl-CoA, the method optionally further comprising enzymatically converting 2,4-pentadienoyl-CoA into 1,3 butadiene using at least one polypeptide having an activity selected from the group consisting of hydratase activity, thioesterase activity, decarboxylase activity, dehydrogenase activity, CoA-transferase activity, and dehydratase activity, wherein the polypeptide having thioesterase activity has at least 90% sequence identity to any one of the amino acids set forth in SEQ ID NO:14-15 and is capable of enzymatically converting 5-hydroxypentoic acid to 2,4-pentadienoyl-CoA.

7. The method of claim 1, wherein the host is subjected to a cultivation strategy under aerobic or micro-aerobic cultivation conditions.

8. The method of claim 1, wherein the host is cultured under conditions of nutrient limitation either via nitrogen, phosphate or oxygen limitation.

9. The method of claim 1, wherein the host is retained using a ceramic membrane to maintain a high cell density during fermentation.

10. The method of claim 1, wherein a principal carbon source fed to the fermentation is derived from a biological feedstock.

11. The method of claim 10, wherein the biological feedstock is, or derives from monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

12. The method of claim 1, wherein a principal carbon source fed to the fermentation is derived from a non-biological feedstock.

13. The method of claim 12, wherein the non-biological feedstock is, or derives from, natural gas, syngas, $CO_2/H_2$, methanol, ethanol, benzoate, non-volatile residue (NVR) or a caustic wash waste stream from cyclohexane oxidation processes, or terephthalic acid I isophthalic acid mixture waste streams.

14. The method of claim 1, wherein the host is a prokaryote selected from the group consisting of *Escherichia; Clostridia; Corynebacteria; Cupriavidus; Pseudomonas; Delftia; Bacillus; Lactobacillus; Lactococcus*; and *Rhodococcus*, or a eukaryote selected from the group consisting of *Aspergillus, Saccharomyces, Pichia, Yarrowia, Issatchenkia, Debaryomyces, Arxula*, and *Kluyveromyces*.

15. The method of claim 1, wherein the host exhibits tolerance to high concentrations of a C5 building block, and wherein the tolerance to high concentrations of a C5 building block is improved through continuous cultivation in a selective environment.

16. The method of claim 1, wherein said host expresses one or more exogenous polypeptides selected from the group consisting of having an acetyl-CoA synthetase, a 6-phosphogluconate dehydrogenase; a transketolase; a feedback resistant threonine deaminase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a propionyl-CoA synthetase; a L-alanine dehydrogenase; a L-glutamate dehydrogenase; a L-glutamine synthetase; a lysine transporter; a dicarboxylate transporter; and a multidrug transporter activity.

17. The method of claim 1, wherein the host comprises an attenuation of one or more polypeptides having an activity selected from the group consisting of: polyhydroxyalkanoate synthase, an acetyl-CoA thioesterase, an acetyl-CoA specific/J-ketothiolase, an acetoacetyl-CoA reductase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, a transhydrogenase dissipating the cofactor imbalance, aglutamate dehydrogenase specific for the cofactor for which an imbalance is created, a NADH/NADPH-utilizing glutamate dehydrogenase, a pimeloyl-CoA dehydrogenase; an acyl-CoA dehydrogenase accepting C5 building blocks and central precursors as substrates; a glutaryl-CoA dehydrogenase; and a pimeloyl-CoA synthetase.

18. The method of claim 2 wherein the at least one polypeptide having synthase activity is classified under EC 2.3.1.-, the polypeptide having dehydrogenase activity is classified under EC 1.1.1-, and the polypeptide having dehydratase activity is classified under EC 4.2.1-.

19. The method of claim 5 wherein the polypeptide having CoA-transferase activity is classified under EC 2.8.3-, the polypeptide having synthase activity is classified under EC 2.3.1.-, and the polypeptide having dehydratase activity is classified under EC 4.2.1.-.

20. The method of claim 6 wherein the polypeptide having hydratase activity is classified under EC 4.2.1.119 or EC 4.2.1.17, the polypeptide having dehydrogenase activity is classified under EC 1.1.1.-, the polypeptide having CoA-transferase activity is classified under 2.8.3.-, and the polypeptide having dehydratase activity is classified under EC 4.2.1.-.

* * * * *

SEQUENCE LISTING

```
<160> NUMBER OF SEQ ID NOS: 17

<210> SEQ ID NO 1
<211> LENGTH: 256
<212> TYPE: PRT
<213> ORGANISM: Escherichia coli

<400> SEQUENCE: 1

Met Asn Asn Ile Trp Trp Gln Thr Lys Gly Gln Gly Asn Val His Leu
 1               5                   10                  15
```

-continued

Val Leu Leu His Gly Trp Gly Leu Asn Ala Glu Val Trp Arg Cys Ile
20 25 30

Asp Glu Glu Leu Ser Ser His Phe Thr Leu His Leu Val Asp Leu Pro
35 40 45

Gly Phe Gly Arg Ser Arg Gly Phe Gly Ala Leu Ser Leu Ala Asp Met
50 55 60

Ala Glu Ala Val Leu Gln Gln Ala Pro Asp Lys Ala Ile Trp Leu Gly
65 70 75 80

Trp Ser Leu Gly Gly Leu Val Ala Ser Gln Ile Ala Leu Thr His Pro
85 90 95

Glu Arg Val Gln Ala Leu Val Thr Val Ala Ser Ser Pro Cys Phe Ser
100 105 110

Ala Arg Asp Glu Trp Pro Gly Ile Lys Pro Asp Val Leu Ala Gly Phe
115 120 125

Gln Gln Gln Leu Ser Asp Asp Phe Gln Arg Thr Val Glu Arg Phe Leu
130 135 140

Ala Leu Gln Thr Met Gly Thr Glu Thr Ala Arg Gln Asp Ala Arg Ala
145 150 155 160

Leu Lys Lys Thr Val Leu Ala Leu Pro Met Pro Glu Val Asp Val Leu
165 170 175

Asn Gly Gly Leu Glu Ile Leu Lys Thr Val Asp Leu Arg Gln Pro Leu
180 185 190

Gln Asn Val Ser Met Pro Phe Leu Arg Leu Tyr Gly Tyr Leu Asp Gly
195 200 205

Leu Val Pro Arg Lys Val Val Pro Met Leu Asp Lys Leu Trp Pro His
210 215 220

Ser Glu Ser Tyr Ile Phe Ala Lys Ala Ala His Ala Pro Phe Ile Ser
225 230 235 240

His Pro Ala Glu Phe Cys His Leu Leu Val Ala Leu Lys Gln Arg Val
245 250 255

<210> SEQ ID NO 2
<211> LENGTH: 1174
<212> TYPE: PRT
<213> ORGANISM: Mycobacterium marinum

<400> SEQUENCE: 2

Met Ser Pro Ile Thr Arg Glu Glu Arg Leu Glu Arg Arg Ile Gln Asp
1 5 10 15

Leu Tyr Ala Asn Asp Pro Gln Phe Ala Ala Ala Lys Pro Ala Thr Ala
20 25 30

Ile Thr Ala Ala Ile Glu Arg Pro Gly Leu Pro Leu Pro Gln Ile Ile
35 40 45

Glu Thr Val Met Thr Gly Tyr Ala Asp Arg Pro Ala Leu Ala Gln Arg
50 55 60

Ser Val Glu Phe Val Thr Asp Ala Gly Thr Gly His Thr Thr Leu Arg
65 70 75 80

Leu Leu Pro His Phe Glu Thr Ile Ser Tyr Gly Glu Leu Trp Asp Arg
85 90 95

Ile Ser Ala Leu Ala Asp Val Leu Ser Thr Glu Gln Thr Val Lys Pro
100 105 110

Gly Asp Arg Val Cys Leu Leu Gly Phe Asn Ser Val Asp Tyr Ala Thr
115 120 125

Ile Asp Met Thr Leu Ala Arg Leu Gly Ala Val Ala Val Pro Leu Gln
130 135 140

```
Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
            165                 170                 175

Leu Ala Leu Ser Gly Gln Thr Ala Thr Arg Val Leu Val Phe Asp His
        180                 185                 190

His Arg Gln Val Asp Ala His Arg Ala Ala Val Glu Ser Ala Arg Glu
    195                 200                 205

Arg Leu Ala Gly Ser Ala Val Val Glu Thr Leu Ala Glu Ala Ile Ala
210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
            260                 265                 270

Phe Trp Arg Lys Arg Thr Trp Phe Glu Gly Gly Tyr Glu Pro Ser Ile
        275                 280                 285

Thr Leu Asn Phe Met Pro Met Ser His Val Met Gly Arg Gln Ile Leu
    290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
            340                 345                 350

Ser Glu Val Asp Arg Arg Leu Val Asp Gly Ala Asp Arg Val Ala Leu
        355                 360                 365

Glu Ala Gln Val Lys Ala Glu Ile Arg Asn Asp Val Leu Gly Gly Arg
370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                405                 410                 415

Ser Thr Glu Ala Gly Met Ile Leu Ile Asp Gly Ala Ile Arg Arg Pro
            420                 425                 430

Ala Val Leu Asp Tyr Lys Leu Val Asp Val Pro Asp Leu Gly Tyr Phe
        435                 440                 445

Leu Thr Asp Arg Pro His Pro Arg Gly Glu Leu Leu Val Lys Thr Asp
    450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
            500                 505                 510

Leu Ser Gln Gly Glu Phe Val Thr Val Ser Lys Leu Glu Ala Val Phe
        515                 520                 525

Gly Asp Ser Pro Leu Val Arg Gln Ile Tyr Ile Tyr Gly Asn Ser Ala
    530                 535                 540

Arg Ala Tyr Leu Leu Ala Val Ile Val Pro Thr Gln Glu Ala Leu Asp
545                 550                 555                 560
```

```
Ala Val Pro Val Glu Glu Leu Lys Ala Arg Leu Gly Asp Ser Leu Gln
            565                 570                 575
Glu Val Ala Lys Ala Ala Gly Leu Gln Ser Tyr Glu Ile Pro Arg Asp
        580                 585                 590
Phe Ile Ile Glu Thr Thr Pro Trp Thr Leu Glu Asn Gly Leu Leu Thr
    595                 600                 605
Gly Ile Arg Lys Leu Ala Arg Pro Gln Leu Lys Lys His Tyr Gly Glu
610                 615                 620
Leu Leu Glu Gln Ile Tyr Thr Asp Leu Ala His Gly Gln Ala Asp Glu
625                 630                 635                 640
Leu Arg Ser Leu Arg Gln Ser Gly Ala Asp Ala Pro Val Leu Val Thr
                645                 650                 655
Val Cys Arg Ala Ala Ala Ala Leu Leu Gly Gly Ser Ala Ser Asp Val
            660                 665                 670
Gln Pro Asp Ala His Phe Thr Asp Leu Gly Gly Asp Ser Leu Ser Ala
        675                 680                 685
Leu Ser Phe Thr Asn Leu Leu His Glu Ile Phe Asp Ile Glu Val Pro
    690                 695                 700
Val Gly Val Ile Val Ser Pro Ala Asn Asp Leu Gln Ala Leu Ala Asp
705                 710                 715                 720
Tyr Val Glu Ala Ala Arg Lys Pro Gly Ser Ser Arg Pro Thr Phe Ala
                725                 730                 735
Ser Val His Gly Ala Ser Asn Gly Gln Val Thr Glu Val His Ala Gly
            740                 745                 750
Asp Leu Ser Leu Asp Lys Phe Ile Asp Ala Ala Thr Leu Ala Glu Ala
        755                 760                 765
Pro Arg Leu Pro Ala Ala Asn Thr Gln Val Arg Thr Val Leu Leu Thr
    770                 775                 780
Gly Ala Thr Gly Phe Leu Gly Arg Tyr Leu Ala Leu Glu Trp Leu Glu
785                 790                 795                 800
Arg Met Asp Leu Val Asp Gly Lys Leu Ile Cys Leu Val Arg Ala Lys
                805                 810                 815
Ser Asp Thr Glu Ala Arg Ala Arg Leu Asp Lys Thr Phe Asp Ser Gly
            820                 825                 830
Asp Pro Glu Leu Leu Ala His Tyr Arg Ala Leu Ala Gly Asp His Leu
        835                 840                 845
Glu Val Leu Ala Gly Asp Lys Gly Glu Ala Asp Leu Gly Leu Asp Arg
    850                 855                 860
Gln Thr Trp Gln Arg Leu Ala Asp Thr Val Asp Leu Ile Val Asp Pro
865                 870                 875                 880
Ala Ala Leu Val Asn His Val Leu Pro Tyr Ser Gln Leu Phe Gly Pro
                885                 890                 895
Asn Ala Leu Gly Thr Ala Glu Leu Leu Arg Leu Ala Leu Thr Ser Lys
            900                 905                 910
Ile Lys Pro Tyr Ser Tyr Thr Ser Thr Ile Gly Val Ala Asp Gln Ile
        915                 920                 925
Pro Pro Ser Ala Phe Thr Glu Asp Ala Asp Ile Arg Val Ile Ser Ala
    930                 935                 940
Thr Arg Ala Val Asp Asp Ser Tyr Ala Asn Gly Tyr Ser Asn Ser Lys
945                 950                 955                 960
Trp Ala Gly Glu Val Leu Leu Arg Glu Ala His Asp Leu Cys Gly Leu
                965                 970                 975
Pro Val Ala Val Phe Arg Cys Asp Met Ile Leu Ala Asp Thr Thr Trp
```

```
              980             985             990
Ala Gly Gln Leu Asn Val Pro Asp Met Phe Thr Arg Met Ile Leu Ser
            995                 1000                1005

Leu Ala Ala Thr Gly Ile Ala Pro Gly Ser Phe Tyr Glu Leu Ala Ala
        1010                1015                1020

Asp Gly Ala Arg Gln Arg Ala His Tyr Asp Gly Leu Pro Val Glu Phe
1025                1030                1035                1040

Ile Ala Glu Ala Ile Ser Thr Leu Gly Ala Gln Ser Gln Asp Gly Phe
                1045                1050                1055

His Thr Tyr His Val Met Asn Pro Tyr Asp Gly Ile Gly Leu Asp
            1060                1065                1070

Glu Phe Val Asp Trp Leu Asn Glu Ser Gly Cys Pro Ile Gln Arg Ile
        1075                1080                1085

Ala Asp Tyr Gly Asp Trp Leu Gln Arg Phe Glu Thr Ala Leu Arg Ala
            1090                1095                1100

Leu Pro Asp Arg Gln Arg His Ser Ser Leu Leu Pro Leu His Asn
1105                1110                1115                1120

Tyr Arg Gln Pro Glu Arg Pro Val Arg Gly Ser Ile Ala Pro Thr Asp
                1125                1130                1135

Arg Phe Arg Ala Ala Val Gln Glu Ala Lys Ile Gly Pro Asp Lys Asp
            1140                1145                1150

Ile Pro His Val Gly Ala Pro Ile Ile Val Lys Tyr Val Ser Asp Leu
        1155                1160                1165

Arg Leu Leu Gly Leu Leu
    1170

<210> SEQ ID NO 3
<211> LENGTH: 1173
<212> TYPE: PRT
<213> ORGANISM: Mycobacterium smegmatis

<400> SEQUENCE: 3

Met Thr Ser Asp Val His Asp Ala Thr Asp Gly Val Thr Glu Thr Ala
1               5                   10                  15

Leu Asp Asp Glu Gln Ser Thr Arg Ile Ala Glu Leu Tyr Ala Thr
            20                  25                  30

Asp Pro Glu Phe Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175
```

```
Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
    290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
370                 375                 380

Leu Arg Glu Gln Val Leu Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
            420                 425                 430

Thr Arg Asp Gly Val Ile Val Arg Pro Pro Val Ile Asp Tyr Lys Leu
        435                 440                 445

Ile Asp Val Pro Glu Leu Gly Tyr Phe Ser Thr Asp Lys Pro Tyr Pro
450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
        515                 520                 525

Ala Val Ala Asn Leu Glu Ala Val Phe Ser Gly Ala Ala Leu Val Arg
530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
            580                 585                 590

Leu Gln Ser Tyr Glu Val Pro Ala Asp Phe Ile Val Glu Thr Glu Pro
```

```
                595                 600                 605
        Phe Ser Ala Ala Asn Gly Leu Leu Ser Gly Val Gly Lys Leu Leu Arg
        610                 615                 620
        Pro Asn Leu Lys Asp Arg Tyr Gly Gln Arg Leu Glu Gln Met Tyr Ala
        625                 630                 635                 640
        Asp Ile Ala Ala Thr Gln Ala Asn Gln Leu Arg Glu Leu Arg Arg Ala
                            645                 650                 655
        Ala Ala Thr Gln Pro Val Ile Asp Thr Leu Thr Gln Ala Ala Ala Thr
                        660                 665                 670
        Ile Leu Gly Thr Gly Ser Glu Val Ala Ser Asp Ala His Phe Thr Asp
                    675                 680                 685
        Leu Gly Gly Asp Ser Leu Ser Ala Leu Thr Leu Ser Asn Leu Leu Ser
        690                 695                 700
        Asp Phe Phe Gly Phe Glu Val Pro Val Gly Thr Ile Val Asn Pro Ala
        705                 710                 715                 720
        Thr Asn Leu Ala Gln Leu Ala Gln His Ile Glu Ala Gln Arg Thr Ala
                        725                 730                 735
        Gly Asp Arg Arg Pro Ser Phe Thr Thr Val His Gly Ala Asp Ala Thr
                    740                 745                 750
        Glu Ile Arg Ala Ser Glu Leu Thr Leu Asp Lys Phe Ile Asp Ala Glu
                755                 760                 765
        Thr Leu Arg Ala Ala Pro Gly Leu Pro Lys Val Thr Thr Glu Pro Arg
        770                 775                 780
        Thr Val Leu Leu Ser Gly Ala Asn Gly Trp Leu Gly Arg Phe Leu Thr
        785                 790                 795                 800
        Leu Gln Trp Leu Glu Arg Leu Ala Pro Val Gly Gly Thr Leu Ile Thr
                        805                 810                 815
        Ile Val Arg Gly Arg Asp Asp Ala Ala Ala Arg Ala Arg Leu Thr Gln
                    820                 825                 830
        Ala Tyr Asp Thr Asp Pro Glu Leu Ser Arg Arg Phe Ala Glu Leu Ala
                835                 840                 845
        Asp Arg His Leu Arg Val Val Ala Gly Asp Ile Gly Asp Pro Asn Leu
        850                 855                 860
        Gly Leu Thr Pro Glu Ile Trp His Arg Leu Ala Ala Glu Val Asp Leu
        865                 870                 875                 880
        Val Val His Pro Ala Ala Leu Val Asn His Val Leu Pro Tyr Arg Gln
                        885                 890                 895
        Leu Phe Gly Pro Asn Val Val Gly Thr Ala Glu Val Ile Lys Leu Ala
                    900                 905                 910
        Leu Thr Glu Arg Ile Lys Pro Val Thr Tyr Leu Ser Thr Val Ser Val
                915                 920                 925
        Ala Met Gly Ile Pro Asp Phe Glu Glu Asp Gly Asp Ile Arg Thr Val
        930                 935                 940
        Ser Pro Val Arg Pro Leu Asp Gly Gly Tyr Ala Asn Gly Tyr Gly Asn
        945                 950                 955                 960
        Ser Lys Trp Ala Gly Glu Val Leu Leu Arg Glu Ala His Asp Leu Cys
                        965                 970                 975
        Gly Leu Pro Val Ala Thr Phe Arg Ser Asp Met Ile Leu Ala His Pro
                    980                 985                 990
        Arg Tyr Arg Gly Gln Val Asn Val Pro Asp Met Phe Thr Arg Leu Leu
                995                 1000                1005
        Leu Ser Leu Leu Ile Thr Gly Val Ala Pro Arg Ser Phe Tyr Ile Gly
        1010                1015                1020
```

```
Asp Gly Glu Arg Pro Arg Ala His Tyr Pro Gly Leu Thr Val Asp Phe
1025                1030                1035                1040

Val Ala Glu Ala Val Thr Thr Leu Gly Ala Gln Gln Arg Glu Gly Tyr
            1045                1050                1055

Val Ser Tyr Asp Val Met Asn Pro His Asp Asp Gly Ile Ser Leu Asp
        1060                1065                1070

Val Phe Val Asp Trp Leu Ile Arg Ala Gly His Pro Ile Asp Arg Val
    1075                1080                1085

Asp Asp Tyr Asp Asp Trp Val Arg Arg Phe Glu Thr Ala Leu Thr Ala
    1090                1095                1100

Leu Pro Glu Lys Arg Arg Ala Gln Thr Val Leu Pro Leu Leu His Ala
1105                1110                1115                1120

Phe Arg Ala Pro Gln Ala Pro Leu Arg Gly Ala Pro Glu Pro Thr Glu
                1125                1130                1135

Val Phe His Ala Ala Val Arg Thr Ala Lys Val Gly Pro Gly Asp Ile
            1140                1145                1150

Pro His Leu Asp Glu Ala Leu Ile Asp Lys Tyr Ile Arg Asp Leu Arg
        1155                1160                1165

Glu Phe Gly Leu Ile
    1170

<210> SEQ ID NO 4
<211> LENGTH: 1148
<212> TYPE: PRT
<213> ORGANISM: Segniliparus rugosus

<400> SEQUENCE: 4

Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
        35                  40                  45

Leu Asp Thr Leu Met Arg Gly Tyr Ala Glu Arg Pro Ala Leu Ala His
    50                  55                  60

Arg Val Gly Ala Gly Tyr Glu Thr Ile Ser Tyr Gly Glu Leu Trp Ala
65                  70                  75                  80

Arg Val Gly Ala Ile Ala Ala Trp Gln Ala Asp Gly Leu Ala Pro
                85                  90                  95

Gly Asp Phe Val Ala Thr Val Gly Phe Thr Ser Pro Asp Tyr Val Ala
            100                 105                 110

Val Asp Leu Ala Ala Ala Arg Ser Gly Leu Val Ser Val Pro Leu Gln
        115                 120                 125

Ala Gly Ala Ser Leu Ala Gln Leu Val Gly Ile Leu Glu Glu Thr Glu
    130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                165                 170                 175

Arg Gly Pro Asp Ala Ser Glu Ser Ala Ala Asp Glu Arg Arg Gly Ala
            180                 185                 190

Leu Ala Asp Ala Glu Glu Gln Leu Ala Arg Ala Gly Arg Ala Val Val
        195                 200                 205

Val Glu Thr Leu Ala Asp Leu Ala Ala Arg Gly Glu Ala Leu Pro Glu
```

```
                210                 215                 220
Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                245                 250                 255

Gln Arg Leu Val Ser Gln Leu Trp Gly Arg Thr Pro Val Val Pro Gly
                260                 265                 270

Met Pro Asn Ile Ser Leu His Tyr Met Pro Leu Ser His Ser Tyr Gly
                275                 280                 285

Arg Ala Val Leu Ala Gly Ala Leu Ser Ala Gly Gly Thr Ala His Phe
                290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                325                 330                 335

Gln Glu Ser Gln Arg Gly Gln Asp Val Ala Glu Leu Arg Glu Arg Val
                340                 345                 350

Leu Gly Gly Arg Leu Leu Val Ala Val Cys Gly Ser Ala Pro Leu Ser
                355                 360                 365

Pro Glu Met Arg Ala Phe Met Glu Glu Val Leu Gly Phe Pro Leu Leu
                370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                405                 410                 415

Leu Gly Tyr Arg Thr Thr Asp Lys Pro Tyr Pro Arg Gly Glu Leu Cys
                420                 425                 430

Ile Arg Ser Thr Ser Leu Ile Ser Gly Tyr Tyr Lys Arg Pro Glu Ile
                435                 440                 445

Thr Ala Glu Val Phe Asp Ala Gln Gly Tyr Tyr Lys Thr Gly Asp Val
                450                 455                 460

Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Tyr Gly Thr Ser Pro Tyr Val Lys Gln Ile Phe Val Tyr
                500                 505                 510

Gly Asn Ser Glu Arg Ser Phe Leu Leu Ala Val Val Val Pro Asn Ala
                515                 520                 525

Glu Val Leu Gly Ala Arg Asp Gln Glu Glu Ala Lys Pro Leu Ile Ala
                530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Thr Gln Asn
                565                 570                 575

Gly Leu Leu Ser Glu Val Gly Lys Leu Leu Arg Pro Lys Leu Lys Ala
                580                 585                 590

Arg Tyr Gly Glu Ala Leu Glu Ala Arg Tyr Asp Glu Ile Ala His Gly
                595                 600                 605

Gln Ala Asp Glu Leu Arg Ala Leu Arg Asp Gly Ala Gly Gln Arg Pro
                610                 615                 620

Val Val Glu Thr Val Val Arg Ala Ala Val Ala Ile Ser Gly Ser Glu
625                 630                 635                 640
```

```
Gly Ala Glu Val Gly Pro Glu Ala Asn Phe Ala Asp Leu Gly Gly Asp
                645                 650                 655

Ser Leu Ser Ala Leu Ser Leu Ala Asn Leu Leu His Asp Val Phe Glu
            660                 665                 670

Val Glu Val Pro Val Arg Ile Ile Ile Gly Pro Thr Ala Ser Leu Ala
        675                 680                 685

Gly Ile Ala Lys His Ile Glu Ala Glu Arg Ala Gly Ala Ser Ala Pro
    690                 695                 700

Thr Ala Ala Ser Val His Gly Ala Gly Ala Thr Arg Ile Arg Ala Ser
705                 710                 715                 720

Glu Leu Thr Leu Glu Lys Phe Leu Pro Glu Asp Leu Ala Ala Ala
                725                 730                 735

Lys Gly Leu Pro Ala Ala Asp Gln Val Arg Thr Val Leu Leu Thr Gly
            740                 745                 750

Ala Asn Gly Trp Leu Gly Arg Phe Leu Ala Leu Glu Gln Leu Glu Arg
        755                 760                 765

Leu Ala Arg Ser Gly Gln Asp Gly Gly Lys Leu Ile Cys Leu Val Arg
    770                 775                 780

Gly Lys Asp Ala Ala Ala Arg Arg Ile Glu Glu Thr Leu Gly
785                 790                 795                 800

Thr Asp Pro Ala Leu Ala Arg Phe Ala Glu Leu Ala Glu Gly Arg
            805                 810                 815

Leu Glu Val Val Pro Gly Asp Val Gly Glu Pro Lys Phe Gly Leu Asp
        820                 825                 830

Asp Ala Ala Trp Asp Arg Leu Ala Glu Glu Val Asp Val Ile Val His
    835                 840                 845

Pro Ala Ala Leu Val Asn His Val Leu Pro Tyr His Gln Leu Phe Gly
850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
            885                 890                 895

Val Glu Pro Ser Ser Phe Glu Glu Asp Gly Asp Ile Arg Ala Val Val
        900                 905                 910

Pro Glu Arg Pro Leu Gly Asp Gly Tyr Ala Asn Gly Tyr Gly Asn Ser
    915                 920                 925

Lys Trp Ala Gly Glu Val Leu Leu Arg Glu Ala His Glu Leu Val Gly
930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
            965                 970                 975

Ser Leu Leu Ala Thr Gly Ile Ala Pro Lys Ser Phe Tyr Gln Gln Gly
        980                 985                 990

Ala Ala Gly Glu Arg Gln Arg Ala His Tyr Asp Gly Ile Pro Val Asp
    995                 1000                1005

Phe Thr Ala Glu Ala Ile Thr Thr Leu Gly Ala Glu Pro Ser Trp Phe
1010                1015                1020

Asp Gly Gly Ala Gly Phe Arg Ser Phe Asp Val Phe Asn Pro His His
1025                1030                1035                1040

Asp Gly Val Gly Leu Asp Glu Phe Val Asp Trp Leu Ile Glu Ala Gly
            1045                1050                1055
```

His Pro Ile Ser Arg Ile Asp Asp His Lys Glu Trp Phe Ala Arg Phe
              1060                1065                1070

Glu Thr Ala Val Arg Gly Leu Pro Glu Ala Gln Arg Gln His Ser Leu
        1075                1080                1085

Leu Pro Leu Leu Arg Ala Tyr Ser Phe Pro His Pro Val Asp Gly
    1090                1095                1100

Ser Val Tyr Pro Thr Gly Lys Phe Gln Gly Ala Val Lys Ala Gln
1105                1110                1115                1120

Val Gly Ser Asp His Asp Val Pro His Leu Gly Lys Ala Leu Ile Val
              1125                1130                1135

Lys Tyr Ala Asp Asp Leu Lys Ala Leu Gly Leu Leu
              1140                1145

<210> SEQ ID NO 5
<211> LENGTH: 1168
<212> TYPE: PRT
<213> ORGANISM: Mycobacterium smegmatis

<400> SEQUENCE: 5

Met Thr Ile Glu Thr Arg Glu Asp Arg Phe Asn Arg Arg Ile Asp His
 1               5                  10                  15

Leu Phe Glu Thr Asp Pro Gln Phe Ala Ala Ala Arg Pro Asp Glu Ala
                20                  25                  30

Ile Ser Ala Ala Ala Asp Pro Glu Leu Arg Leu Pro Ala Ala Val
             35                  40                  45

Lys Gln Ile Leu Ala Gly Tyr Ala Asp Arg Pro Ala Leu Gly Lys Arg
 50                  55                  60

Ala Val Glu Phe Val Thr Asp Glu Glu Gly Arg Thr Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
            100                 105                 110

Arg Val Ala Ile Leu Gly Phe Thr Ser Val Asp Tyr Thr Thr Ile Asp
        115                 120                 125

Ile Ala Leu Leu Glu Leu Gly Ala Val Ser Val Pro Leu Gln Thr Ser
130                 135                 140

Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
                165                 170                 175

Glu Ser Gly Pro Ala Pro Ser Arg Leu Val Val Phe Asp Tyr Ser His
            180                 185                 190

Glu Val Asp Asp Gln Arg Glu Ala Phe Glu Ala Ala Lys Gly Lys Leu
        195                 200                 205

Ala Gly Thr Gly Val Val Val Glu Thr Ile Thr Asp Ala Leu Asp Arg
    210                 215                 220

Gly Arg Ser Leu Ala Asp Ala Pro Leu Tyr Val Pro Asp Glu Ala Asp
225                 230                 235                 240

Pro Leu Thr Leu Leu Ile Tyr Thr Ser Gly Ser Thr Gly Thr Pro Lys
                245                 250                 255

Gly Ala Met Tyr Pro Glu Ser Lys Thr Ala Thr Met Trp Gln Ala Gly
            260                 265                 270

Ser Lys Ala Arg Trp Asp Glu Thr Leu Gly Val Met Pro Ser Ile Thr
        275                 280                 285

```
Leu Asn Phe Met Pro Met Ser His Val Met Gly Arg Gly Ile Leu Cys
        290                 295                 300

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
                325                 330                 335

Asn Phe Val Pro Arg Ile Trp Asp Met Leu Phe Gln Glu Tyr Gln Ser
            340                 345                 350

Arg Leu Asp Asn Arg Arg Ala Glu Gly Ser Glu Asp Arg Ala Glu Ala
        355                 360                 365

Ala Val Leu Glu Glu Val Arg Thr Gln Leu Leu Gly Gly Arg Phe Val
    370                 375                 380

Ser Ala Leu Thr Gly Ser Ala Pro Ile Ser Ala Glu Met Lys Ser Trp
385                 390                 395                 400

Val Glu Asp Leu Leu Asp Met His Leu Leu Glu Gly Tyr Gly Ser Thr
                405                 410                 415

Glu Ala Gly Ala Val Phe Ile Asp Gly Gln Ile Gln Arg Pro Pro Val
            420                 425                 430

Ile Asp Tyr Lys Leu Val Asp Val Pro Asp Leu Gly Tyr Phe Ala Thr
        435                 440                 445

Asp Arg Pro Tyr Pro Arg Gly Glu Leu Leu Val Lys Ser Glu Gln Met
    450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
                485                 490                 495

Asp His Leu Glu Tyr Leu Asp Arg Arg Asn Asn Val Leu Lys Leu Ser
            500                 505                 510

Gln Gly Glu Phe Val Thr Val Ser Lys Leu Glu Ala Val Phe Gly Asp
        515                 520                 525

Ser Pro Leu Val Arg Gln Ile Tyr Val Tyr Gly Asn Ser Ala Arg Ser
    530                 535                 540

Tyr Leu Leu Ala Val Val Val Pro Thr Glu Glu Ala Leu Ser Arg Trp
545                 550                 555                 560

Asp Gly Asp Glu Leu Lys Ser Arg Ile Ser Asp Ser Leu Gln Asp Ala
                565                 570                 575

Ala Arg Ala Ala Gly Leu Gln Ser Tyr Glu Ile Pro Arg Asp Phe Leu
            580                 585                 590

Val Glu Thr Thr Pro Phe Thr Leu Glu Asn Gly Leu Leu Thr Gly Ile
        595                 600                 605

Arg Lys Leu Ala Arg Pro Lys Leu Lys Ala His Tyr Gly Glu Arg Leu
    610                 615                 620

Glu Gln Leu Tyr Thr Asp Leu Ala Glu Gly Gln Ala Asn Glu Leu Arg
625                 630                 635                 640

Glu Leu Arg Arg Asn Gly Ala Asp Arg Pro Val Val Glu Thr Val Ser
                645                 650                 655

Arg Ala Ala Val Ala Leu Leu Gly Ala Ser Val Thr Asp Leu Arg Ser
            660                 665                 670

Asp Ala His Phe Thr Asp Leu Gly Gly Asp Ser Leu Ser Ala Leu Ser
        675                 680                 685

Phe Ser Asn Leu Leu His Glu Ile Phe Asp Val Asp Val Pro Val Gly
    690                 695                 700
```

```
Val Ile Val Ser Pro Ala Thr Asp Leu Ala Gly Val Ala Ala Tyr Ile
705                 710                 715                 720

Glu Gly Glu Leu Arg Gly Ser Lys Arg Pro Thr Tyr Ala Ser Val His
            725                 730                 735

Gly Arg Asp Ala Thr Glu Val Arg Ala Arg Asp Leu Ala Leu Gly Lys
            740                 745                 750

Phe Ile Asp Ala Lys Thr Leu Ser Ala Ala Pro Gly Leu Pro Arg Ser
            755                 760                 765

Gly Thr Glu Ile Arg Thr Val Leu Leu Thr Gly Ala Thr Gly Phe Leu
            770                 775                 780

Gly Arg Tyr Leu Ala Leu Glu Trp Leu Glu Arg Met Asp Leu Val Asp
785                 790                 795                 800

Gly Lys Val Ile Cys Leu Val Arg Ala Arg Ser Asp Asp Glu Ala Arg
                805                 810                 815

Ala Arg Leu Asp Ala Thr Phe Asp Thr Gly Asp Ala Thr Leu Leu Glu
            820                 825                 830

His Tyr Arg Ala Leu Ala Ala Asp His Leu Glu Val Ile Ala Gly Asp
    835                 840                 845

Lys Gly Glu Ala Asp Leu Gly Leu Asp His Asp Thr Trp Gln Arg Leu
850                 855                 860

Ala Asp Thr Val Asp Leu Ile Val Asp Pro Ala Ala Leu Val Asn His
865                 870                 875                 880

Val Leu Pro Tyr Ser Gln Met Phe Gly Pro Asn Ala Leu Gly Thr Ala
                885                 890                 895

Glu Leu Ile Arg Ile Ala Leu Thr Thr Thr Ile Lys Pro Tyr Val Tyr
            900                 905                 910

Val Ser Thr Ile Gly Val Gly Gln Gly Ile Ser Pro Glu Ala Phe Val
            915                 920                 925

Glu Asp Ala Asp Ile Arg Glu Ile Ser Ala Thr Arg Arg Val Asp Asp
            930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
                965                 970                 975

Cys Asp Met Ile Leu Ala Asp Thr Thr Tyr Ser Gly Gln Leu Asn Leu
            980                 985                 990

Pro Asp Met Phe Thr Arg Leu Met Leu Ser Leu Val Ala Thr Gly Ile
            995                 1000                1005

Ala Pro Gly Ser Phe Tyr Glu Leu Asp Ala Asp Gly Asn Arg Gln Arg
    1010                1015                1020

Ala His Tyr Asp Gly Leu Pro Val Glu Phe Ile Ala Glu Ala Ile Ser
1025                1030                1035                1040

Thr Ile Gly Ser Gln Val Thr Asp Gly Phe Glu Thr Phe His Val Met
                1045                1050                1055

Asn Pro Tyr Asp Asp Gly Ile Gly Leu Asp Glu Tyr Val Asp Trp Leu
            1060                1065                1070

Ile Glu Ala Gly Tyr Pro Val His Arg Val Asp Asp Tyr Ala Thr Trp
            1075                1080                1085

Leu Ser Arg Phe Glu Thr Ala Leu Arg Ala Leu Pro Glu Arg Gln Arg
            1090                1095                1100

Gln Ala Ser Leu Leu Pro Leu Leu His Asn Tyr Gln Gln Pro Ser Pro
1105                1110                1115                1120

Pro Val Cys Gly Ala Met Ala Pro Thr Asp Arg Phe Arg Ala Ala Val
```

```
                    1125              1130              1135
Gln Asp Ala Lys Ile Gly Pro Asp Lys Asp Ile Pro His Val Thr Ala
            1140              1145              1150

Asp Val Ile Val Lys Tyr Ile Ser Asn Leu Gln Met Leu Gly Leu Leu
            1155              1160              1165

<210> SEQ ID NO 6
<211> LENGTH: 1185
<212> TYPE: PRT
<213> ORGANISM: Mycobacterium massiliense

<400> SEQUENCE: 6

Met Thr Asn Glu Thr Asn Pro Gln Gln Glu Gln Leu Ser Arg Arg Ile
 1               5                  10                  15

Glu Ser Leu Arg Glu Ser Asp Pro Gln Phe Arg Ala Ala Gln Pro Asp
                20                  25                  30

Pro Ala Val Ala Glu Gln Val Leu Arg Pro Gly Leu His Leu Ser Glu
            35                  40                  45

Ala Ile Ala Ala Leu Met Thr Gly Tyr Ala Glu Arg Pro Ala Leu Gly
        50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Thr Tyr Gly Glu Leu Trp Ser
                85                  90                  95

Arg Thr Thr Ser Val Ala Ala Ala Trp His His Asp Ala Thr His Pro
                100                 105                 110

Val Lys Ala Gly Asp Leu Val Ala Thr Leu Gly Phe Thr Ser Ile Asp
            115                 120                 125

Tyr Thr Val Leu Asp Leu Ala Ile Met Ile Leu Gly Gly Val Ala Val
        130                 135                 140

Pro Leu Gln Thr Ser Ala Pro Ala Ser Gln Trp Thr Thr Ile Leu Ala
145                 150                 155                 160

Glu Ala Glu Pro Asn Thr Leu Ala Val Ser Ile Glu Leu Ile Gly Ala
                165                 170                 175

Ala Met Glu Ser Val Arg Ala Thr Pro Ser Ile Lys Gln Val Val Val
                180                 185                 190

Phe Asp Tyr Thr Pro Glu Val Asp Asp Gln Arg Glu Ala Phe Glu Ala
            195                 200                 205

Ala Ser Thr Gln Leu Ala Gly Thr Gly Ile Ala Leu Glu Thr Leu Asp
        210                 215                 220

Ala Val Ile Ala Arg Gly Ala Ala Leu Pro Ala Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met His Ser Glu Asn Ile Val Arg
                260                 265                 270

Arg Trp Trp Ile Arg Glu Asp Val Met Ala Gly Thr Glu Asn Leu Pro
            275                 280                 285

Met Ile Gly Leu Asn Phe Met Pro Met Ser His Ile Met Gly Arg Gly
        290                 295                 300

Thr Leu Thr Ser Thr Leu Ser Thr Gly Gly Thr Gly Tyr Phe Ala Ala
305                 310                 315                 320

Ser Ser Asp Met Ser Thr Leu Phe Glu Asp Met Glu Leu Ile Arg Pro
                325                 330                 335
```

```
Thr Ala Leu Ala Leu Val Pro Arg Val Cys Asp Met Val Phe Gln Arg
                340                 345                 350

Phe Gln Thr Glu Val Asp Arg Arg Leu Ala Ser Gly Asp Thr Ala Ser
            355                 360                 365

Ala Glu Ala Val Ala Ala Glu Val Lys Ala Asp Ile Arg Asp Asn Leu
370                 375                 380

Phe Gly Gly Arg Val Ser Ala Val Met Val Gly Ser Ala Pro Leu Ser
385                 390                 395                 400

Glu Glu Leu Gly Glu Phe Ile Glu Ser Cys Phe Glu Leu Asn Leu Thr
                405                 410                 415

Asp Gly Tyr Gly Ser Thr Glu Ala Gly Met Val Phe Arg Asp Gly Ile
            420                 425                 430

Val Gln Arg Pro Pro Val Ile Asp Tyr Lys Leu Val Asp Val Pro Glu
        435                 440                 445

Leu Gly Tyr Phe Ser Thr Asp Lys Pro His Pro Arg Gly Glu Leu Leu
    450                 455                 460

Leu Lys Thr Asp Gly Met Phe Leu Gly Tyr Tyr Lys Arg Pro Glu Val
465                 470                 475                 480

Thr Ala Ser Val Phe Asp Ala Asp Gly Phe Tyr Met Thr Gly Asp Ile
                485                 490                 495

Val Ala Glu Leu Ala His Asp Asn Ile Glu Ile Ile Asp Arg Arg Asn
            500                 505                 510

Asn Val Leu Lys Leu Ser Gln Gly Glu Phe Val Ala Val Ala Thr Leu
        515                 520                 525

Glu Ala Glu Tyr Ala Asn Ser Pro Val Val His Gln Ile Tyr Val Tyr
    530                 535                 540

Gly Ser Ser Glu Arg Ser Tyr Leu Leu Ala Val Val Val Pro Thr Pro
545                 550                 555                 560

Glu Ala Val Ala Ala Lys Gly Asp Ala Ala Leu Lys Thr Thr
                565                 570                 575

Ile Ala Asp Ser Leu Gln Asp Ile Ala Lys Glu Ile Gln Leu Gln Ser
                580                 585                 590

Tyr Glu Val Pro Arg Asp Phe Ile Ile Glu Pro Gln Pro Phe Thr Gln
            595                 600                 605

Gly Asn Gly Leu Leu Thr Gly Ile Ala Lys Leu Ala Arg Pro Asn Leu
        610                 615                 620

Lys Ala His Tyr Gly Pro Arg Leu Glu Gln Met Tyr Ala Glu Ile Ala
625                 630                 635                 640

Glu Gln Gln Ala Ala Glu Leu Arg Ala Leu His Gly Val Asp Pro Asp
                645                 650                 655

Lys Pro Ala Leu Glu Thr Val Leu Lys Ala Ala Gln Ala Leu Leu Gly
            660                 665                 670

Val Ser Ser Ala Glu Leu Ala Ala Asp Ala His Phe Thr Asp Leu Gly
        675                 680                 685

Gly Asp Ser Leu Ser Ala Leu Ser Phe Ser Asp Leu Leu Arg Asp Ile
    690                 695                 700

Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
                725                 730                 735

Thr Arg Pro Thr Ala Glu Thr Val His Gly Ala Gly His Thr Glu Ile
            740                 745                 750

Arg Ala Ala Asp Leu Thr Leu Asp Lys Phe Ile Asp Glu Ala Thr Leu
```

```
            755                 760                 765
    His Ala Ala Pro Ser Leu Pro Lys Ala Ala Gly Ile Pro His Thr Val
    770                 775                 780

Leu Leu Thr Gly Ser Asn Gly Tyr Leu Gly His Tyr Leu Ala Leu Glu
    785                 790                 795                 800

Trp Leu Glu Arg Leu Asp Lys Thr Asp Gly Lys Leu Ile Val Ile Val
                        805                 810                 815

Arg Gly Lys Asn Ala Glu Ala Ala Tyr Gly Arg Leu Glu Glu Ala Phe
                        820                 825                 830

Asp Thr Gly Asp Thr Glu Leu Leu Ala His Phe Arg Ser Leu Ala Asp
                        835                 840                 845

Lys His Leu Glu Val Leu Ala Gly Asp Ile Gly Asp Pro Asn Leu Gly
    850                 855                 860

Leu Asp Ala Asp Thr Trp Gln Arg Leu Ala Asp Thr Val Asp Val Ile
    865                 870                 875                 880

Val His Pro Ala Ala Leu Val Asn His Val Leu Pro Tyr Asn Gln Leu
                        885                 890                 895

Phe Gly Pro Asn Val Val Gly Thr Ala Glu Ile Ile Lys Leu Ala Ile
                        900                 905                 910

Thr Thr Lys Ile Lys Pro Val Thr Tyr Leu Ser Thr Val Ala Val Ala
                        915                 920                 925

Ala Tyr Val Asp Pro Thr Thr Phe Asp Glu Glu Ser Asp Ile Arg Leu
    930                 935                 940

Ile Ser Ala Val Arg Pro Ile Asp Asp Gly Tyr Ala Asn Gly Tyr Gly
    945                 950                 955                 960

Asn Ala Lys Trp Ala Gly Glu Val Leu Leu Arg Glu Ala His Asp Leu
                        965                 970                 975

Cys Gly Leu Pro Val Ala Val Phe Arg Ser Asp Met Ile Leu Ala His
                        980                 985                 990

Ser Arg Tyr Thr Gly Gln Leu Asn Val Pro Asp Gln Phe Thr Arg Leu
                        995                 1000                1005

Ile Leu Ser Leu Ile Ala Thr Gly Ile Ala Pro Gly Ser Phe Tyr Gln
    1010                1015                1020

Ala Gln Thr Thr Gly Glu Arg Pro Leu Ala His Tyr Asp Gly Leu Pro
    1025                1030                1035                1040

Gly Asp Phe Thr Ala Glu Ala Ile Thr Thr Leu Gly Thr Gln Val Pro
                        1045                1050                1055

Glu Gly Ser Glu Gly Phe Val Thr Tyr Asp Cys Val Asn Pro His Ala
                        1060                1065                1070

Asp Gly Ile Ser Leu Asp Asn Phe Val Asp Trp Leu Ile Glu Ala Gly
                        1075                1080                1085

Tyr Pro Ile Ala Arg Ile Asp Asn Tyr Thr Glu Trp Phe Thr Arg Phe
    1090                1095                1100

Asp Thr Ala Ile Arg Gly Leu Ser Glu Lys Gln Lys Gln His Ser Leu
    1105                1110                1115                1120

Leu Pro Leu Leu His Ala Phe Glu Gln Pro Ser Ala Ala Glu Asn His
                        1125                1130                1135

Gly Val Val Pro Ala Lys Arg Phe Gln His Ala Val Gln Ala Ala Gly
                        1140                1145                1150

Ile Gly Pro Val Gly Gln Asp Gly Thr Thr Asp Ile Pro His Leu Ser
                        1155                1160                1165

Arg Arg Leu Ile Val Lys Tyr Ala Lys Asp Leu Glu Gln Leu Gly Leu
                        1170                1175                1180
```

Leu
1185

<210> SEQ ID NO 7
<211> LENGTH: 1186
<212> TYPE: PRT
<213> ORGANISM: Segniliparus rotundus

<400> SEQUENCE: 7

Met Thr Gln Ser His Thr Gln Gly Pro Gln Ala Ser Ala Ala His Ser
 1               5                  10                  15

Arg Leu Ala Arg Arg Ala Ala Glu Leu Leu Ala Thr Asp Pro Gln Ala
            20                  25                  30

Ala Ala Thr Leu Pro Asp Pro Glu Val Val Arg Gln Ala Thr Arg Pro
        35                  40                  45

Gly Leu Arg Leu Ala Glu Arg Val Asp Ala Ile Leu Ser Gly Tyr Ala
    50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
        115                 120                 125

Ile Gly Phe Ile Ser Val Asp Tyr Val Ala Ile Asp Ile Ala Gly Val
    130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190

Ser Val Arg Arg Leu Leu Val Phe Asp Tyr Arg Ala Gly Ser Asp Glu
        195                 200                 205

Asp Arg Glu Ala Val Glu Ala Ala Lys Arg Lys Ile Ala Asp Ala Gly
    210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
            260                 265                 270

Gly Ala Met Tyr Pro Glu Arg Asn Val Ala His Phe Trp Gly Gly Val
        275                 280                 285

Trp Ala Ala Ala Phe Asp Glu Asp Ala Ala Pro Val Pro Ala Ile
    290                 295                 300

Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
                325                 330                 335

Asp Leu Ser Thr Leu Phe Glu Asp Leu Lys Leu Ala Arg Pro Thr Asn
            340                 345                 350

Leu Phe Leu Val Pro Arg Val Val Glu Met Leu Tyr Gln His Tyr Gln

```
                355                 360                 365
Ser Glu Leu Asp Arg Arg Gly Val Gln Asp Gly Thr Arg Glu Ala Glu
370                 375                 380

Ala Val Lys Asp Asp Leu Arg Thr Gly Leu Leu Gly Arg Ile Leu
385                 390                 395                 400

Thr Ala Gly Phe Gly Ser Ala Pro Leu Ser Ala Glu Leu Ala Gly Phe
                405                 410                 415

Ile Glu Ser Leu Leu Gln Ile His Leu Val Asp Gly Tyr Gly Ser Thr
            420                 425                 430

Glu Ala Gly Pro Val Trp Arg Asp Gly Tyr Leu Val Lys Pro Pro Val
        435                 440                 445

Thr Asp Tyr Lys Leu Ile Asp Val Pro Glu Leu Gly Tyr Phe Ser Thr
    450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                485                 490                 495

Glu Asp Gly Phe Tyr Leu Thr Gly Asp Val Val Ala Gln Ile Gly Pro
            500                 505                 510

Glu Gln Phe Ala Tyr Val Asp Arg Arg Lys Asn Val Leu Lys Leu Ser
        515                 520                 525

Gln Gly Glu Phe Val Thr Leu Ala Lys Leu Glu Ala Ala Tyr Ser Ser
    530                 535                 540

Ser Pro Leu Val Arg Gln Leu Phe Val Tyr Gly Ser Ser Glu Arg Ser
545                 550                 555                 560

Tyr Leu Leu Ala Val Ile Val Pro Thr Pro Asp Ala Leu Lys Lys Phe
                565                 570                 575

Gly Val Gly Glu Ala Ala Lys Ala Leu Gly Glu Ser Leu Gln Lys
            580                 585                 590

Ile Ala Arg Asp Glu Gly Leu Gln Ser Tyr Glu Val Pro Arg Asp Phe
        595                 600                 605

Ile Ile Glu Thr Asp Pro Phe Thr Val Glu Asn Gly Leu Leu Ser Asp
    610                 615                 620

Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
                645                 650                 655

Arg Asp Ile Arg Arg Gly Val Gln Gln Arg Pro Thr Leu Glu Thr Val
            660                 665                 670

Arg Arg Ala Ala Ala Met Leu Gly Ala Ser Ala Ala Glu Ile Lys
        675                 680                 685

Pro Asp Ala His Phe Thr Asp Leu Gly Gly Asp Ser Leu Ser Ala Leu
    690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
                725                 730                 735

Ile Asp Ala Gln Leu Ala Gly Gly Arg Ala Arg Pro Thr Phe Ala Thr
            740                 745                 750

Val His Gly Lys Gly Ser Thr Thr Ile Lys Ala Ser Asp Leu Thr Leu
        755                 760                 765

Asp Lys Phe Ile Asp Glu Gln Thr Leu Glu Ala Ala Lys His Leu Pro
    770                 775                 780
```

```
Lys Pro Ala Asp Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
            805                 810                 815

Ala Gly Gly Lys Leu Ile Thr Ile Val Arg Gly Lys Asp Ala Ala Gln
        820                 825                 830

Ala Lys Ala Arg Leu Asp Ala Ala Tyr Glu Ser Gly Asp Pro Lys Leu
    835                 840                 845

Ala Gly His Tyr Gln Asp Leu Ala Ala Thr Thr Leu Glu Val Leu Ala
850                 855                 860

Gly Asp Phe Ser Glu Pro Arg Leu Gly Leu Asp Glu Ala Thr Trp Asn
865                 870                 875                 880

Arg Leu Ala Asp Glu Val Asp Phe Ile Ser His Pro Gly Ala Leu Val
            885                 890                 895

Asn His Val Leu Pro Tyr Asn Gln Leu Phe Gly Pro Asn Val Ala Gly
        900                 905                 910

Val Ala Glu Ile Ile Lys Leu Ala Ile Thr Thr Arg Ile Lys Pro Val
    915                 920                 925

Thr Tyr Leu Ser Thr Val Ala Val Ala Ala Gly Val Glu Pro Ser Ala
930                 935                 940

Leu Asp Glu Asp Gly Asp Ile Arg Thr Val Ser Ala Glu Arg Ser Val
945                 950                 955                 960

Asp Glu Gly Tyr Ala Asn Gly Tyr Gly Asn Ser Lys Trp Gly Gly Glu
            965                 970                 975

Val Leu Leu Arg Glu Ala His Asp Arg Thr Gly Leu Pro Val Arg Val
        980                 985                 990

Phe Arg Ser Asp Met Ile Leu Ala His Gln Lys Tyr Thr Gly Gln Val
    995                 1000                1005

Asn Ala Thr Asp Gln Phe Thr Arg Leu Val Gln Ser Leu Leu Ala Thr
    1010                1015                1020

Gly Leu Ala Pro Lys Ser Phe Tyr Glu Leu Asp Ala Gln Gly Asn Arg
1025                1030                1035                1040

Gln Arg Ala His Tyr Asp Gly Ile Pro Val Asp Phe Thr Ala Glu Ser
            1045                1050                1055

Ile Thr Thr Leu Gly Gly Asp Gly Leu Glu Gly Tyr Arg Ser Tyr Asn
        1060                1065                1070

Val Phe Asn Pro His Arg Asp Gly Val Gly Leu Asp Glu Phe Val Asp
    1075                1080                1085

Trp Leu Ile Glu Ala Gly His Pro Ile Thr Arg Ile Asp Asp Tyr Asp
    1090                1095                1100

Gln Trp Leu Ser Arg Phe Glu Thr Ser Leu Arg Gly Leu Pro Glu Ser
1105                1110                1115                1120

Lys Arg Gln Ala Ser Val Leu Pro Leu Leu His Ala Phe Ala Arg Pro
            1125                1130                1135

Gly Pro Ala Val Asp Gly Ser Pro Phe Arg Asn Thr Val Phe Arg Thr
        1140                1145                1150

Asp Val Gln Lys Ala Lys Ile Gly Ala Glu His Asp Ile Pro His Leu
    1155                1160                1165

Gly Lys Ala Leu Val Leu Lys Tyr Ala Asp Asp Ile Lys Gln Leu Gly
    1170                1175                1180

Leu Leu
1185
```

```
<210> SEQ ID NO 8
<211> LENGTH: 382
<212> TYPE: PRT
<213> ORGANISM: Pseudomonas fluorescens

<400> SEQUENCE: 8

Met Gln Ile Gln Gly His Tyr Glu Leu Gln Phe Glu Ala Val Arg Glu
 1               5                   10                  15

Ala Phe Ala Ala Leu Phe Asp Asp Pro Gln Glu Arg Gly Ala Gly Leu
            20                  25                  30

Cys Ile Gln Ile Gly Gly Glu Thr Val Val Asp Leu Trp Ala Gly Thr
        35                  40                  45

Ala Asp Lys Asp Gly Thr Glu Ala Trp His Ser Asp Thr Ile Val Asn
 50                  55                  60

Leu Phe Ser Cys Thr Lys Thr Phe Thr Ala Val Thr Ala Leu Gln Leu
 65                  70                  75                  80

Val Ala Glu Gly Lys Leu Gln Leu Asp Ala Pro Val Ala Asn Tyr Trp
                85                  90                  95

Pro Glu Phe Ala Ala Ala Gly Lys Glu Ala Ile Thr Leu Arg Gln Leu
            100                 105                 110

Leu Cys His Gln Ala Gly Leu Pro Ala Ile Arg Glu Met Leu Pro Thr
        115                 120                 125

Glu Ala Leu Tyr Asp Trp Arg Leu Met Val Asp Thr Leu Ala Ala Glu
130                 135                 140

Ala Pro Trp Trp Thr Pro Gly Gln Gly His Gly Tyr Glu Ala Ile Thr
145                 150                 155                 160

Tyr Gly Trp Leu Val Gly Glu Leu Leu Arg Arg Ala Asp Gly Arg Gly
                165                 170                 175

Pro Gly Glu Ser Ile Val Ala Arg Val Ala Arg Pro Leu Gly Leu Asp
            180                 185                 190

Phe His Val Gly Leu Ala Asp Glu Glu Phe Tyr Arg Val Ala His Ile
        195                 200                 205

Ala Arg Ser Lys Gly Asn Met Gly Asp Glu Ala Ala Gln Arg Leu Leu
210                 215                 220

Gln Val Met Met Arg Glu Pro Thr Ala Met Thr Thr Arg Ala Phe Ala
225                 230                 235                 240

Asn Pro Pro Ser Ile Leu Thr Ser Thr Asn Lys Pro Glu Trp Arg Arg
                245                 250                 255

Met Gln Gln Pro Ala Ala Asn Gly His Gly Asn Ala Arg Ser Leu Ala
            260                 265                 270

Gly Phe Tyr Ser Gly Leu Leu Asp Gly Ser Leu Leu Glu Ala Asp Met
        275                 280                 285

Leu Glu Gln Leu Thr Arg Glu His Ser Ile Gly Pro Asp Lys Thr Leu
290                 295                 300

Leu Thr Gln Thr Arg Phe Gly Leu Gly Cys Met Leu Asp Gln Gln Pro
305                 310                 315                 320

Gln Leu Pro Asn Ala Thr Phe Gly Leu Gly Pro Arg Ala Phe Gly His
                325                 330                 335

Pro Arg Ser Ala Pro Val Val Trp Val Leu Pro Glu His Asp Val
            340                 345                 350

Ala Phe Gly Phe Val Thr Asn Thr Leu Gly Pro Tyr Val Leu Met Asp
        355                 360                 365

Pro Arg Ala Gln Lys Leu Val Gly Ile Leu Ala Gly Cys Leu
370                 375                 380
```

<210> SEQ ID NO 9
<211> LENGTH: 246
<212> TYPE: PRT
<213> ORGANISM: Lactobacillus brevis

<400> SEQUENCE: 9

Met Ala Ala Asn Glu Phe Ser Glu Thr His Arg Val Val Tyr Tyr Glu
1               5                   10                  15

Ala Asp Asp Thr Gly Gln Leu Thr Leu Ala Met Leu Ile Asn Leu Phe
            20                  25                  30

Val Leu Val Ser Glu Asp Gln Asn Asp Ala Leu Gly Leu Ser Thr Ala
        35                  40                  45

Phe Val Gln Ser His Gly Val Gly Trp Val Val Thr Gln Tyr His Leu
    50                  55                  60

His Ile Asp Glu Leu Pro Arg Thr Gly Ala Gln Val Thr Ile Lys Thr
65                  70                  75                  80

Arg Ala Thr Ala Tyr Asn Arg Tyr Phe Ala Tyr Arg Glu Tyr Trp Leu
                85                  90                  95

Leu Asp Asp Ala Gly Gln Val Leu Ala Tyr Gly Glu Gly Ile Trp Val
            100                 105                 110

Thr Met Ser Tyr Ala Thr Arg Lys Ile Thr Thr Ile Pro Ala Glu Val
        115                 120                 125

Met Ala Pro Tyr His Ser Glu Glu Gln Thr Arg Leu Pro Arg Leu Pro
    130                 135                 140

Arg Pro Asp His Phe Asp Glu Ala Val Asn Gln Thr Leu Lys Pro Tyr
145                 150                 155                 160

Thr Val Arg Tyr Phe Asp Ile Asp Gly Asn Gly His Val Asn Asn Ala
                165                 170                 175

His Tyr Phe Asp Trp Met Leu Asp Val Leu Pro Ala Thr Phe Leu Arg
            180                 185                 190

Ala His His Pro Thr Asp Val Lys Ile Arg Phe Glu Asn Glu Val Gln
        195                 200                 205

Tyr Gly His Gln Val Thr Ser Glu Leu Ser Gln Ala Ala Ala Leu Thr
    210                 215                 220

Thr Gln His Met Ile Lys Val Gly Asp Leu Thr Ala Val Lys Ala Thr
225                 230                 235                 240

Ile Gln Trp Asp Asn Arg
                245

<210> SEQ ID NO 10
<211> LENGTH: 261
<212> TYPE: PRT
<213> ORGANISM: Lactobacillus plantarum

<400> SEQUENCE: 10

Met Ala Thr Leu Gly Ala Asn Ala Ser Leu Tyr Ser Glu Gln His Arg
1               5                   10                  15

Ile Thr Tyr Tyr Glu Cys Asp Arg Thr Gly Arg Ala Thr Leu Thr Thr
            20                  25                  30

Leu Ile Asp Ile Ala Val Leu Ala Ser Glu Asp Gln Ser Asp Ala Leu
        35                  40                  45

Gly Leu Thr Thr Glu Met Val Gln Ser His Gly Val Gly Trp Val Val
    50                  55                  60

Thr Gln Tyr Ala Ile Asp Ile Thr Arg Met Pro Arg Gln Asp Glu Val
65                  70                  75                  80

```
Val Thr Ile Ala Val Arg Gly Ser Ala Tyr Asn Pro Tyr Phe Ala Tyr
                85                  90                  95

Arg Glu Phe Trp Ile Arg Asp Ala Asp Gly Gln Gln Leu Ala Tyr Ile
            100                 105                 110

Thr Ser Ile Trp Val Met Met Ser Gln Thr Thr Arg Arg Ile Val Lys
        115                 120                 125

Ile Leu Pro Glu Leu Val Ala Pro Tyr Gln Ser Glu Val Val Lys Arg
130                 135                 140

Ile Pro Arg Leu Pro Arg Pro Ile Ser Phe Glu Ala Thr Asp Thr Thr
145                 150                 155                 160

Ile Thr Lys Pro Tyr His Val Arg Phe Phe Asp Ile Asp Pro Asn Arg
                165                 170                 175

His Val Asn Asn Ala His Tyr Phe Asp Trp Leu Val Asp Thr Leu Pro
            180                 185                 190

Ala Thr Phe Leu Leu Gln His Asp Leu Val His Val Asp Val Arg Tyr
        195                 200                 205

Glu Asn Glu Val Lys Tyr Gly Gln Thr Val Thr Ala His Ala Asn Ile
210                 215                 220

Leu Pro Ser Glu Val Ala Asp Gln Val Thr Thr Ser His Leu Ile Glu
225                 230                 235                 240

Val Asp Asp Glu Lys Cys Cys Glu Val Thr Ile Gln Trp Arg Thr Leu
                245                 250                 255

Pro Glu Pro Ile Gln
                260

<210> SEQ ID NO 11
<211> LENGTH: 397
<212> TYPE: PRT
<213> ORGANISM: Treponema denticola

<400> SEQUENCE: 11

Met Ile Val Lys Pro Met Val Arg Asn Asn Ile Cys Leu Asn Ala His
1               5                   10                  15

Pro Gln Gly Cys Lys Lys Gly Val Glu Asp Gln Ile Glu Tyr Thr Lys
            20                  25                  30

Lys Arg Ile Thr Ala Glu Val Lys Ala Gly Ala Lys Ala Pro Lys Asn
        35                  40                  45

Val Leu Val Leu Gly Cys Ser Asn Gly Tyr Gly Leu Ala Ser Arg Ile
50                  55                  60

Thr Ala Ala Phe Gly Tyr Gly Ala Ala Thr Ile Gly Val Ser Phe Glu
65                  70                  75                  80

Lys Ala Gly Ser Glu Thr Lys Tyr Gly Thr Pro Gly Trp Tyr Asn Asn
                85                  90                  95

Leu Ala Phe Asp Glu Ala Ala Lys Arg Glu Gly Leu Tyr Ser Val Thr
            100                 105                 110

Ile Asp Gly Asp Ala Phe Ser Asp Glu Ile Lys Ala Gln Val Ile Glu
        115                 120                 125

Glu Ala Lys Lys Lys Gly Ile Lys Phe Asp Leu Ile Val Tyr Ser Leu
130                 135                 140

Ala Ser Pro Val Arg Thr Asp Pro Asp Thr Gly Ile Met His Lys Ser
145                 150                 155                 160

Val Leu Lys Pro Phe Gly Lys Thr Phe Thr Gly Lys Thr Val Asp Pro
                165                 170                 175

Phe Thr Gly Glu Leu Lys Glu Ile Ser Ala Glu Pro Ala Asn Asp Glu
```

```
                180                 185                 190
Glu Ala Ala Thr Val Lys Val Met Gly Gly Glu Asp Trp Glu Arg
            195                 200                 205

Trp Ile Lys Gln Leu Ser Lys Glu Gly Leu Leu Glu Glu Gly Cys Ile
        210                 215                 220

Thr Leu Ala Tyr Ser Tyr Ile Gly Pro Glu Ala Thr Gln Ala Leu Tyr
225                 230                 235                 240

Arg Lys Gly Thr Ile Gly Lys Ala Lys Glu His Leu Glu Ala Thr Ala
                245                 250                 255

His Arg Leu Asn Lys Glu Asn Pro Ser Ile Arg Ala Phe Val Ser Val
            260                 265                 270

Asn Lys Gly Leu Val Thr Arg Ala Ser Ala Val Ile Pro Val Ile Pro
        275                 280                 285

Leu Tyr Leu Ala Ser Leu Phe Lys Val Met Lys Glu Lys Gly Asn His
    290                 295                 300

Glu Gly Cys Ile Glu Gln Ile Thr Arg Leu Tyr Ala Glu Arg Leu Tyr
305                 310                 315                 320

Arg Lys Asp Gly Thr Ile Pro Val Asp Glu Glu Asn Arg Ile Arg Ile
                325                 330                 335

Asp Asp Trp Glu Leu Glu Asp Val Gln Lys Ala Val Ser Ala Leu
            340                 345                 350

Met Glu Lys Val Thr Gly Glu Asn Ala Glu Ser Leu Thr Asp Leu Ala
        355                 360                 365

Gly Tyr Arg His Asp Phe Leu Ala Ser Asn Gly Phe Asp Val Glu Gly
    370                 375                 380

Ile Asn Tyr Glu Ala Glu Val Glu Arg Phe Asp Arg Ile
385                 390                 395

<210> SEQ ID NO 12
<211> LENGTH: 539
<212> TYPE: PRT
<213> ORGANISM: Euglena gracilis

<400> SEQUENCE: 12

Met Ser Cys Pro Ala Ser Pro Ser Ala Ala Val Val Ser Ala Gly Ala
1               5                   10                  15

Leu Cys Leu Cys Val Ala Thr Val Leu Leu Ala Thr Gly Ser Asn Pro
            20                  25                  30

Thr Ala Leu Ser Thr Ala Ser Thr Arg Ser Pro Thr Ser Leu Val Arg
        35                  40                  45

Gly Val Asp Arg Gly Leu Met Arg Pro Thr Thr Ala Ala Leu Thr
    50                  55                  60

Thr Met Arg Glu Val Pro Gln Met Ala Glu Gly Phe Ser Gly Glu Ala
65                  70                  75                  80

Thr Ser Ala Trp Ala Ala Gly Pro Gln Trp Ala Pro Leu Val
                85                  90                  95

Ala Ala Ala Ser Ser Ala Leu Ala Leu Trp Trp Ala Ala Arg Arg
            100                 105                 110

Ser Val Arg Arg Pro Leu Ala Ala Leu Ala Glu Leu Pro Thr Ala Val
        115                 120                 125

Thr His Leu Ala Pro Pro Met Ala Met Phe Thr Thr Ala Lys Val
    130                 135                 140

Ile Gln Pro Lys Ile Arg Gly Phe Ile Cys Thr Thr Thr His Pro Ile
145                 150                 155                 160
```

Gly Cys Glu Lys Arg Val Gln Glu Glu Ile Ala Tyr Ala Arg Ala His
            165                 170                 175

Pro Pro Thr Ser Pro Gly Pro Lys Arg Val Leu Val Ile Gly Cys Ser
        180                 185                 190

Thr Gly Tyr Gly Leu Ser Thr Arg Ile Thr Ala Ala Phe Gly Tyr Gln
        195                 200                 205

Ala Ala Thr Leu Gly Val Phe Leu Ala Gly Pro Pro Thr Lys Gly Arg
    210                 215                 220

Pro Ala Ala Ala Gly Trp Tyr Asn Thr Val Ala Phe Glu Lys Ala Ala
225                 230                 235                 240

Leu Glu Ala Gly Leu Tyr Ala Arg Ser Leu Asn Gly Asp Ala Phe Asp
                245                 250                 255

Ser Thr Thr Lys Ala Arg Thr Val Glu Ala Ile Lys Arg Asp Leu Gly
                260                 265                 270

Thr Val Asp Leu Val Val Tyr Ser Ile Ala Ala Pro Lys Arg Thr Asp
            275                 280                 285

Pro Ala Thr Gly Val Leu His Lys Ala Cys Leu Lys Pro Ile Gly Ala
        290                 295                 300

Thr Tyr Thr Asn Arg Thr Val Asn Thr Asp Lys Ala Glu Val Thr Asp
305                 310                 315                 320

Val Ser Ile Glu Pro Ala Ser Pro Glu Glu Ile Ala Asp Thr Val Lys
                325                 330                 335

Val Met Gly Gly Glu Asp Trp Glu Leu Trp Ile Gln Ala Leu Ser Glu
            340                 345                 350

Ala Gly Val Leu Ala Glu Gly Ala Lys Thr Val Ala Tyr Ser Tyr Ile
        355                 360                 365

Gly Pro Glu Met Thr Trp Pro Val Tyr Trp Ser Gly Thr Ile Gly Glu
    370                 375                 380

Ala Lys Lys Asp Val Glu Lys Ala Ala Lys Arg Ile Thr Gln Gln Tyr
385                 390                 395                 400

Gly Cys Pro Ala Tyr Pro Val Val Ala Lys Ala Leu Val Thr Gln Ala
                405                 410                 415

Ser Ser Ala Ile Pro Val Val Pro Leu Tyr Ile Cys Leu Leu Tyr Arg
            420                 425                 430

Val Met Lys Glu Lys Gly Thr His Glu Gly Cys Ile Glu Gln Met Val
        435                 440                 445

Arg Leu Leu Thr Thr Lys Leu Tyr Pro Glu Asn Gly Ala Pro Ile Val
    450                 455                 460

Asp Glu Ala Gly Arg Val Arg Val Asp Asp Trp Glu Met Ala Glu Asp
465                 470                 475                 480

Val Gln Gln Ala Val Lys Asp Leu Trp Ser Gln Val Ser Thr Ala Asn
                485                 490                 495

Leu Lys Asp Ile Ser Asp Phe Ala Gly Tyr Gln Thr Glu Phe Leu Arg
            500                 505                 510

Leu Phe Gly Phe Gly Ile Asp Gly Val Asp Tyr Asp Gln Pro Val Asp
        515                 520                 525

Val Glu Ala Asp Leu Pro Ser Ala Ala Gln Gln
    530                 535

<210> SEQ ID NO 13
<211> LENGTH: 269
<212> TYPE: PRT
<213> ORGANISM: Bacillus cereus

<400> SEQUENCE: 13

```
Met Ile Asn Lys Thr Leu Leu Gln Lys Arg Phe Asn Gly Ala Ala Val
 1               5                  10                 15

Ser Tyr Asp Arg Tyr Ala Asn Val Gln Lys Lys Met Ala His Ser Leu
             20                  25                  30

Leu Ser Ile Leu Lys Glu Arg Tyr Ser Glu Thr Ala Ser Ile Arg Ile
             35                  40                  45

Leu Glu Leu Gly Cys Gly Thr Gly Tyr Val Thr Glu Gln Leu Ser Lys
 50                  55                  60

Leu Phe Pro Lys Ser His Ile Thr Ala Val Asp Phe Ala Glu Ser Met
 65                  70                  75                  80

Ile Ala Ile Ala Gln Thr Arg Gln Asn Val Lys Asn Val Thr Phe His
                 85                  90                  95

Cys Glu Asp Ile Glu Arg Leu Arg Leu Glu Glu Ser Tyr Asp Val Ile
             100                 105                 110

Ile Ser Asn Ala Thr Phe Gln Trp Leu Asn Asn Leu Gln Gln Val Leu
             115                 120                 125

Arg Asn Leu Phe Gln His Leu Ser Ile Asp Gly Ile Leu Leu Phe Ser
 130                 135                 140

Thr Phe Gly His Glu Thr Phe Gln Glu Leu His Ala Ser Phe Gln Arg
145                 150                 155                 160

Ala Lys Glu Glu Arg Asn Ile Lys Asn Glu Thr Ser Ile Gly Gln Arg
                 165                 170                 175

Phe Tyr Ser Lys Asp Gln Leu Leu His Ile Cys Lys Ile Glu Thr Gly
             180                 185                 190

Asp Val His Val Ser Glu Thr Cys Tyr Ile Glu Ser Phe Thr Glu Val
             195                 200                 205

Lys Glu Phe Leu His Ser Ile Arg Lys Val Gly Ala Thr Asn Ser Asn
 210                 215                 220

Glu Gly Ser Tyr Cys Gln Ser Pro Ser Leu Phe Arg Ala Met Leu Arg
225                 230                 235                 240

Ile Tyr Glu Arg Asp Phe Thr Gly Asn Glu Gly Ile Met Ala Thr Tyr
                 245                 250                 255

His Ala Leu Phe Ile His Ile Thr Lys Glu Gly Lys Arg
             260                 265

<210> SEQ ID NO 14
<211> LENGTH: 132
<212> TYPE: PRT
<213> ORGANISM: Escherichia coli

<400> SEQUENCE: 14

Met Ser Thr Thr His Asn Val Pro Gln Gly Asp Leu Val Leu Arg Thr
 1               5                  10                  15

Leu Ala Met Pro Ala Asp Thr Asn Ala Asn Gly Asp Ile Phe Gly Gly
             20                  25                  30

Trp Leu Met Ser Gln Met Asp Ile Gly Gly Ala Ile Leu Ala Lys Glu
             35                  40                  45

Ile Ala His Gly Arg Val Val Thr Val Arg Val Glu Gly Met Thr Phe
 50                  55                  60

Leu Arg Pro Val Ala Val Gly Asp Val Val Cys Cys Tyr Ala Arg Cys
 65                  70                  75                  80

Val Gln Lys Gly Thr Thr Ser Val Ser Ile Asn Ile Glu Val Trp Val
                 85                  90                  95

Lys Lys Val Ala Ser Glu Pro Ile Gly Gln Arg Tyr Lys Ala Thr Glu
```

Ala Leu Phe Lys Tyr Val Ala Val Asp Pro Glu Gly Lys Pro Arg Ala
    115                 120                 125

Leu Pro Val Glu
    130

<210> SEQ ID NO 15
<211> LENGTH: 286
<212> TYPE: PRT
<213> ORGANISM: Escherichia coli

<400> SEQUENCE: 15

Met Ser Gln Ala Leu Lys Asn Leu Leu Thr Leu Leu Asn Leu Glu Lys
 1               5                  10                  15

Ile Glu Glu Gly Leu Phe Arg Gly Gln Ser Glu Asp Leu Gly Leu Arg
             20                  25                  30

Gln Val Phe Gly Gly Gln Val Gly Gln Ala Leu Tyr Ala Ala Lys
         35                  40                  45

Glu Thr Val Pro Glu Glu Arg Leu Val His Ser Phe His Ser Tyr Phe
     50                  55                  60

Leu Arg Pro Gly Asp Ser Lys Lys Pro Ile Ile Tyr Asp Val Glu Thr
 65                  70                  75                  80

Leu Arg Asp Gly Asn Ser Phe Ser Ala Arg Arg Val Ala Ala Ile Gln
                 85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285

<210> SEQ ID NO 16
<211> LENGTH: 224
<212> TYPE: PRT
<213> ORGANISM: Bacillus subtilis

<400> SEQUENCE: 16

Met Lys Ile Tyr Gly Ile Tyr Met Asp Arg Pro Leu Ser Gln Glu Glu

```
             1               5                  10                  15
           Asn Glu Arg Phe Met Ser Phe Ile Ser Pro Glu Lys Arg Glu Lys Cys
                              20                  25                  30

Arg Arg Phe Tyr His Lys Glu Asp Ala His Arg Thr Leu Leu Gly Asp
                   35                  40                  45

Val Leu Val Arg Ser Val Ile Ser Arg Gln Tyr Gln Leu Asp Lys Ser
               50                  55                  60

Asp Ile Arg Phe Ser Thr Gln Glu Tyr Gly Lys Pro Cys Ile Pro Asp
           65                  70                  75                  80

Leu Pro Asp Ala His Phe Asn Ile Ser His Ser Gly Arg Trp Val Ile
                               85                  90                  95

Cys Ala Phe Asp Ser Gln Pro Ile Gly Ile Asp Ile Glu Lys Thr Lys
                              100                 105                 110

Pro Ile Ser Leu Glu Ile Ala Lys Arg Phe Phe Ser Lys Thr Glu Tyr
                          115                 120                 125

Ser Asp Leu Leu Ala Lys Asp Lys Asp Glu Gln Thr Asp Tyr Phe Tyr
                       130                 135                 140

His Leu Trp Ser Met Lys Glu Ser Phe Ile Lys Gln Glu Gly Lys Gly
           145                 150                 155                 160

Leu Ser Leu Pro Leu Asp Ser Phe Ser Val Arg Leu His Gln Asp Gly
                               165                 170                 175

Gln Val Ser Ile Glu Leu Pro Asp Ser His Ser Pro Cys Tyr Ile Lys
                           180                 185                 190

Thr Tyr Glu Val Asp Pro Gly Tyr Lys Met Ala Val Cys Ala Ala His
                       195                 200                 205

Pro Asp Phe Pro Glu Asp Ile Thr Met Val Ser Tyr Glu Glu Leu Leu
                   210                 215                 220

<210> SEQ ID NO 17
<211> LENGTH: 222
<212> TYPE: PRT
<213> ORGANISM: Nocardia sp. NRRL 5646

<400> SEQUENCE: 17

Met Ile Glu Thr Ile Leu Pro Ala Gly Val Glu Ser Ala Glu Leu Leu
           1               5                  10                  15

Glu Tyr Pro Glu Asp Leu Lys Ala His Pro Ala Glu Glu His Leu Ile
                              20                  25                  30

Ala Lys Ser Val Glu Lys Arg Arg Asp Phe Ile Gly Ala Arg His
                   35                  40                  45

Cys Ala Arg Leu Ala Leu Ala Glu Leu Gly Glu Pro Val Ala Ile
               50                  55                  60

Gly Lys Gly Glu Arg Gly Ala Pro Ile Trp Pro Arg Gly Val Val Gly
           65                  70                  75                  80

Ser Leu Thr His Cys Asp Gly Tyr Arg Ala Ala Val Ala His Lys
                               85                  90                  95

Met Arg Phe Arg Ser Ile Gly Ile Asp Ala Glu Pro His Ala Thr Leu
                              100                 105                 110

Pro Glu Gly Val Leu Asp Ser Val Ser Leu Pro Pro Glu Arg Glu Trp
                          115                 120                 125

Leu Lys Thr Thr Asp Ser Ala Leu His Leu Asp Arg Leu Leu Phe Cys
                       130                 135                 140

Ala Lys Glu Ala Thr Tyr Lys Ala Trp Trp Pro Leu Thr Ala Arg Trp
           145                 150                 155                 160
```

```
Leu Gly Phe Glu Glu Ala His Ile Thr Phe Glu Ile Glu Asp Gly Ser
            165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
            195                 200                 205

Leu Ile Ala Asp Gly Phe Ile Leu Thr Ala Ile Ala Tyr Ala
            210                 215             220
```